US011071856B2

United States Patent
Melman

(10) Patent No.: US 11,071,856 B2
(45) Date of Patent: Jul. 27, 2021

(54) ADVANCED ELECTRODE ARRAY LOCATION EVALUATION

(71) Applicant: Cochlear Limited, Macquarie University (AU)

(72) Inventor: Ryan Orin Melman, Macquarie University (AU)

(73) Assignee: Cochlear Limited, Macquarie University (AU)

(*) Notice: Subject to any disclaimer, the term of this patent is extended or adjusted under 35 U.S.C. 154(b) by 218 days.

(21) Appl. No.: 15/936,282

(22) Filed: Mar. 26, 2018

(65) Prior Publication Data
US 2018/0280687 A1     Oct. 4, 2018

Related U.S. Application Data

(60) Provisional application No. 62/647,896, filed on Mar. 26, 2018, provisional application No. 62/642,566, (Continued)

(51) Int. Cl.
*A61N 1/36* (2006.01)
*A61N 1/05* (2006.01)
(Continued)

(52) U.S. Cl.
CPC .......... *A61N 1/0541* (2013.01); *A61N 1/08* (2013.01); *A61N 1/36038* (2017.08); *A61N 1/36039* (2017.08); *H04R 25/70* (2013.01)

(58) Field of Classification Search
CPC .............. A61N 1/3603; A61N 1/36038; A61N 1/36039
See application file for complete search history.

(56) References Cited

U.S. PATENT DOCUMENTS

| 4,532,930 A | 8/1985 | Crosby et al. |
| 5,626,629 A | 5/1997 | Faltys et al. |

(Continued)

FOREIGN PATENT DOCUMENTS

| EP | 1754509 A1 | 2/2007 |
| KR | 20080015212 A | 2/2008 |

(Continued)

OTHER PUBLICATIONS

International Search Report and Written Opinion for PCT/IB2018/052015, dated Jul. 13, 2018.

(Continued)

*Primary Examiner* — Allen Porter
(74) *Attorney, Agent, or Firm* — Pilloff Passino & Cosenza LLP; Martin J. Cosenza

(57) ABSTRACT

A method, including sequentially activating a plurality of respective electrode pairs of an implanted cochlear implant, at least one of the electrodes of the respective electrode pairs being a respective electrode of an electrode array implanted in a cochlea, thereby generating respective localized electric fields, concurrently respectively measuring, for the plurality of activated respective electrode pairs, an electrical characteristic between the respective electrodes of the respective electrode pairs resulting from the respective localized electric fields, thereby obtaining a measurement set, determining, from the measurement set, a distance between the electrode array and a wall of the cochlea.

24 Claims, 61 Drawing Sheets

Related U.S. Application Data filed on Mar. 13, 2018, provisional application No. 62/633,054, filed on Feb. 20, 2018, provisional application No. 62/559,782, filed on Sep. 18, 2017, provisional application No. 62/476,295, filed on Mar. 24, 2017.

(51) Int. Cl.
*A61N 1/08* (2006.01)
*H04R 25/00* (2006.01)

(56) References Cited

U.S. PATENT DOCUMENTS

| | | | |
|---|---|---|---|
| 5,674,264 | A | 10/1997 | Carter et al. |
| 6,751,505 | B1 | 6/2004 | Van Den Honert et al. |
| 7,206,640 | B1 | 4/2007 | Overstreet |
| 7,684,856 | B2 | 3/2010 | Virtanen |
| 8,014,853 | B2 | 9/2011 | Kraus et al. |
| 8,073,354 | B2 | 12/2011 | Yamada |
| 8,532,781 | B1 | 9/2013 | Vanpoucke |
| 9,173,585 | B2 | 11/2015 | Tsampazis et al. |
| 9,320,887 | B2 | 4/2016 | Kals |
| 2005/0101878 | A1 | 5/2005 | Daly et al. |
| 2007/0270949 | A1 | 11/2007 | Paolini et al. |
| 2009/0023976 | A1 | 10/2009 | Cho et al. |
| 2009/0248110 | A1 | 10/2009 | Choi et al. |
| 2010/0114288 | A1 | 5/2010 | Haller et al. |
| 2011/0087085 | A1 | 4/2011 | Tsampazis et al. |
| 2011/0196245 | A1 | 8/2011 | Poupko et al. |
| 2012/0071957 | A1 | 3/2012 | Carter |
| 2012/0191161 | A1 | 7/2012 | van Dijk |
| 2012/0316454 | A1* | 12/2012 | Carter ............. A61B 5/053 600/547 |
| 2013/0085362 | A1 | 4/2013 | Choi et al. |
| 2013/0172718 | A1 | 7/2013 | Choi et al. |
| 2015/0012059 | A1 | 1/2015 | Kim et al. |
| 2015/0112408 | A1* | 4/2015 | Kais ............. A61N 1/0541 607/57 |
| 2015/0258337 | A1 | 9/2015 | Long et al. |
| 2015/0289787 | A1 | 10/2015 | Buchman et al. |
| 2015/0314122 | A1 | 11/2015 | Kabot et al. |
| 2015/0320550 | A1 | 11/2015 | Downng et al. |
| 2016/0015291 | A1 | 1/2016 | Tsampazis et al. |
| 2016/0059014 | A1 | 3/2016 | Johnston et al. |
| 2016/0059015 | A1 | 3/2016 | Risi et al. |
| 2016/0228704 | A1 | 8/2016 | McLaughlin et al. |
| 2016/0367195 | A1 | 12/2016 | Park et al. |
| 2017/0340883 | A1 | 11/2017 | Johnston et al. |
| 2018/0056058 | A1 | 3/2018 | Heasman et al. |
| 2018/0140829 | A1 | 5/2018 | Ramos de Miguel, Sr. et al. |

FOREIGN PATENT DOCUMENTS

| | | | |
|---|---|---|---|
| KR | 100859979 | B1 | 9/2008 |
| KR | 20130089549 | A | 8/2013 |
| KR | 20160149878 | A | 12/2016 |
| WO | 02082982 | A1 | 10/2002 |
| WO | 2009026625 | A1 | 3/2009 |
| WO | 2016205872 | A1 | 12/2016 |
| WO | 2017182682 | A1 | 10/2017 |
| WO | 2018173010 | A1 | 9/2018 |
| WO | 2019162837 | A1 | 8/2019 |
| WO | 2019175764 | A1 | 9/2019 |
| WO | 2019186373 | A1 | 10/2019 |

OTHER PUBLICATIONS

Vanpoucke, et al. "Identification of the Impedance Model of an Imlanted Cochlear Prosthesis From Intracochlear Potential Measurements." IEEE Transactions on Biomedical Engineering, Dec. 2004, pp. 2174-2183, vol. 51, No. 12.

Filiep J. Vanpoucke et al., "Assessing the Placement of a Cochlear Electrode Array by Multidimensional Scaling," IEEE Transactions on Biomedical Engineering, Feb. 2012, pp. 307-310, vol. 59, No. 2.

Lucas H. M. Mens, "Advances in Cochlear Implant Telemetry: Evoked Neural Responses, Electrical Field Imaging, and Technical Integrity," Trends in Amplification, Sep. 2007, pp. 143-159, vol. 11, No. 3.

Rhett Herman, "An introduction to electrical resistivity in geophysics," Am. J. Phys., Sep. 2001, pp. 943-952, vol., 69, No. 9.

R. Clement et al., "Comparison of three arrays in time-lapse ERT: Simulation of a leachate injection experiment," ArcheoSciences, Oct. 2009, 33 (suppl.).

DR. M.H.Loke, "Electrical imaging surveys for environmental and engineering studies a practical guide to 2-D and 3-D surveys," Aug. 1999.

A. Roy et al., "Depth of Investigation in Direct Current Methods," Geophysics, Oct. 1971, pp. 343-959, vol. 36, No. 5.

R.D. Barker, "Depth of investigation of collinear symmetrical four-electrode arrays," Geophysics, Aug. 1989, pp. 1,031-1,037, vol. 54, No. 8.

International Search Report and Written Opinion for PCT/ES2017/000049, dated Aug. 4, 2017.

Wilko Grolman et al., "Spread of Excitation Measurements for the Detection of Electrode Array Foldovers: A Prospective Study Comparing 3-Dimensional Rotational X-ray and Intraoperative Spread of Excitation Measurements," Otology & Neurotology, Jan. 1, 2009, pp. 27-33, vol. 30.

Octavio Garaycochea et al., "Intra-operative radiological diagnosis of a tip roll-over electrode array displacement using fluoroscopy, when electrophysiological testing is normal: the importance of both techniques in cochlear implant surgery," Brazilian Journal of Otorhinolaryngology, Jun. 2017.

Luke Campbell et al., "Intraoperative Real-time Cochlear Response Telemetry Predicts Hearing Preservation in Cochlear Implantation," Otology & Neurotology, Apr. 2016.

S. Abdul et al., "The use of electrical impedance spectroscopy in the detection of cervical intraepithelial neoplasia," Int J Gynecol Cancer, Sep. 2006, pp. 1823-1832, vol. 16.

Chin-Tuan Tan et al., "Real-time measurement of electrode impedance during intracochlear electrode insertion," Laryngoscope, Apr. 2013, vol. 123, No. 4.

Phillip Tran, "Investigation of cochlear implant stimulation using a finite element model," Mar. 2015, University of Sydney PhD thesis.

Justin C Williams et al., "Complex impedance spectroscopy for monitoring tissue responses to inserted neural Implants," Journal of Neural Engineering, Nov. 27, 2007, pp. 410-423, vol. 4.

Marcus Yip et al., "Energy-efficient waveform for electrical stimulation of the cochlear nerve," Scientific Reports, Oct. 19, 2017, vol. 7.

Jason Pile et al., "Characterization of Friction and Speed Effects and Methods for Detection of Cochlear Implant Electrode Tip Foldover," 2013 IEEE International Conference on Robotics and Automation (ICRA), May 2013, pp. 4409-4414.

Alan G. Micco et al., "Electrical Resistivity Measurements in the Mammalian Cochlea After Neural Degeneration," Laryngoscope, Aug. 2006, pp. 1334-141, vol. 116.

International Search Report and Written Opinion for PCT/IB2019/051345, dated Jul. 18, 2019.

Phillip Tran et al., "Development of Heather for Cochlear Implant Stimulation Using a New Modeling Workflow," IEEE Transactions on Biomedical Engineering, Oct. 2014.

International Search Report and Written Opinion for PCT/IB2019/051992, dated Jul. 9, 2019.

International Search Report and Written Opinion for PCT/IB2019/052414, dated Aug. 2, 2019.

H. Smeds et al., "Endolymphatic hydrops is prevalent in the first weeks following cochlear implantation," Hearing Research, May 2015, pp. 48-57, vol. 327.

Jan Kiefer et al., "Representation of acoustic signals in the human cochlea in presence of a cochlear implant electrode," Hearing Research, Sep. 2006, p. 36-46, vol. 221.

Kyeung A. Ryu et al., "Intracochlear Bleeding Enhances Cochlear Fibrosis and Ossification: An Animal Study," PLoS One, Aug. 2015.

(56) References Cited

OTHER PUBLICATIONS

Alicia M. Quesnel et al., "Delayed loss of hearing after hearing preservation cochlear implantation: human temporal bone pathology and implications for etiology," Hearing Research, Mar. 2016, pp. 225-234, vol. 333.

Extended European Search Report for European Patent Application No. 18 770 349.1, dated Dec. 14, 2020.

* cited by examiner

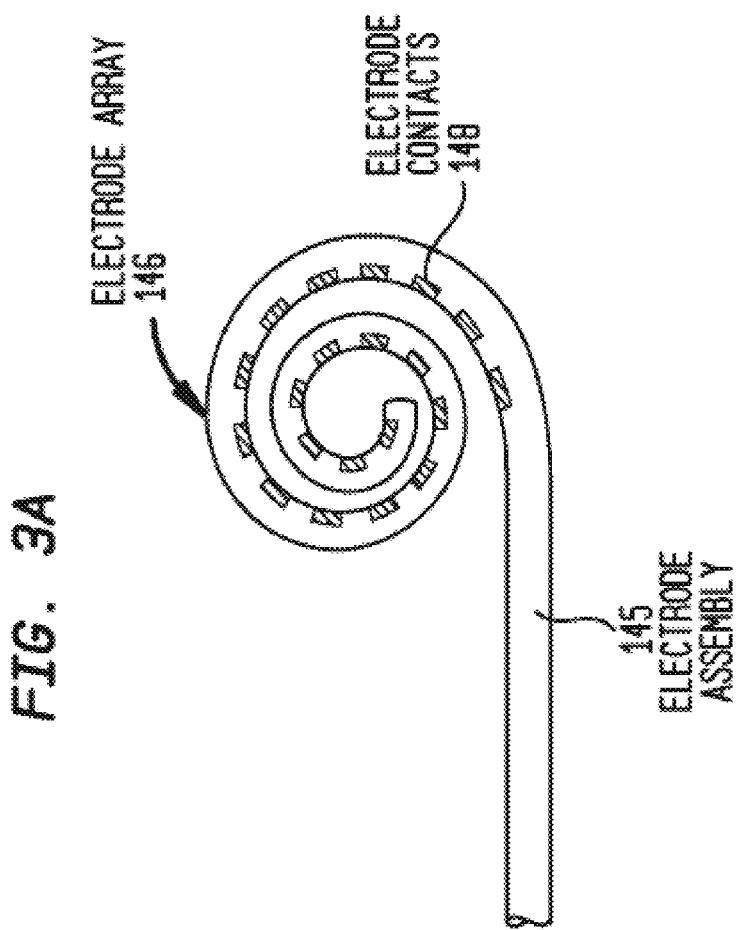

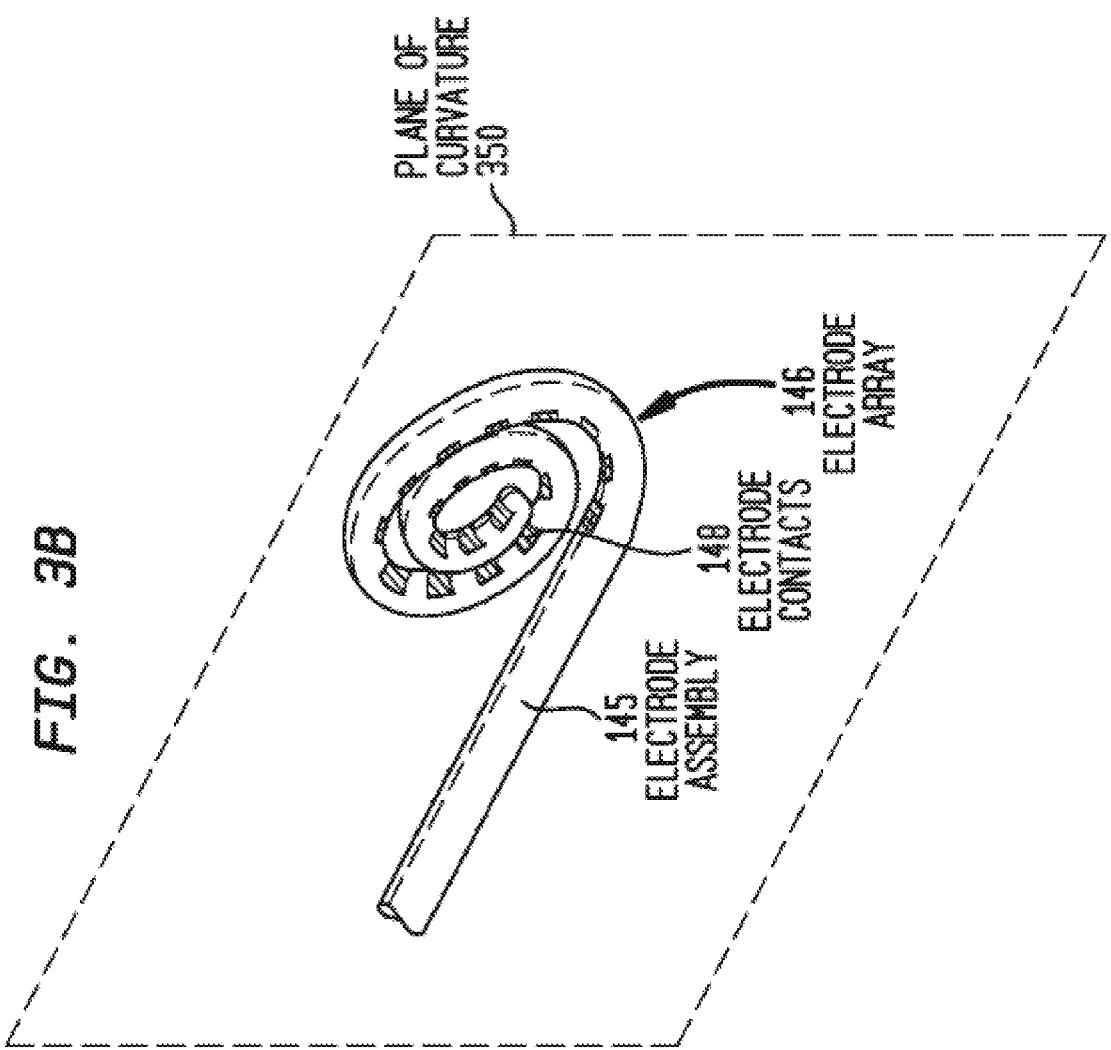

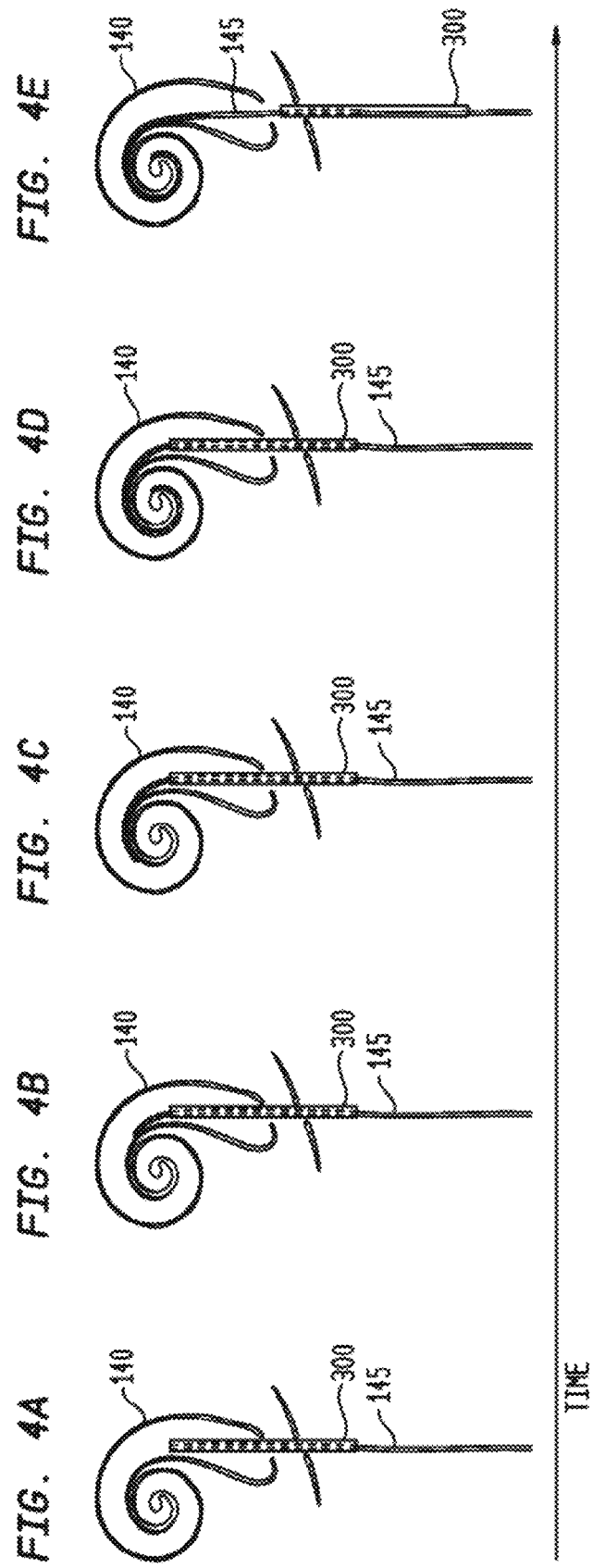

ELECTRODE ASSEMBLY 145
LONGITUDINAL AXIS 501
ELECTRODE CONTACT 148

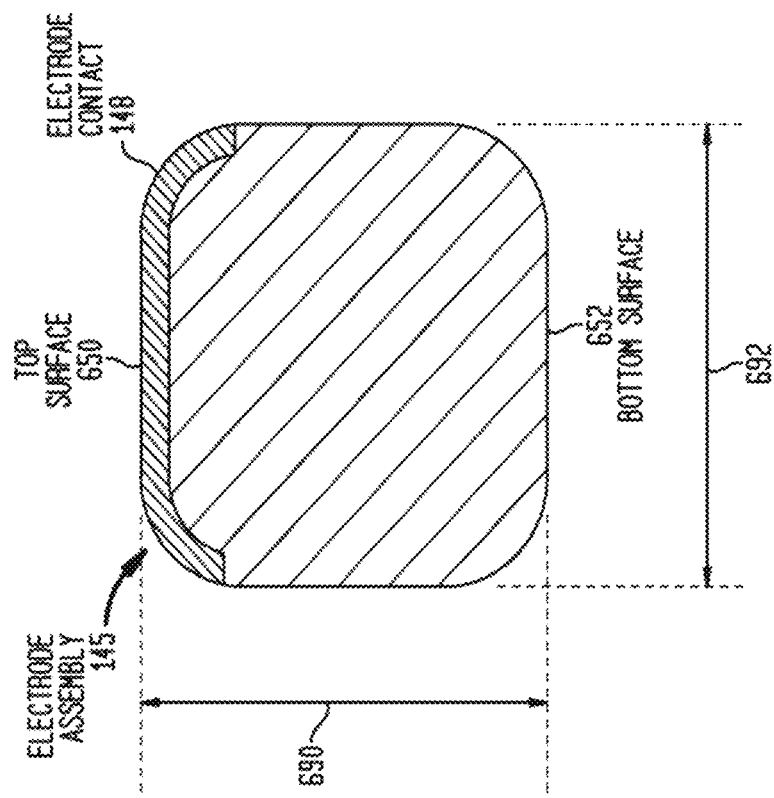

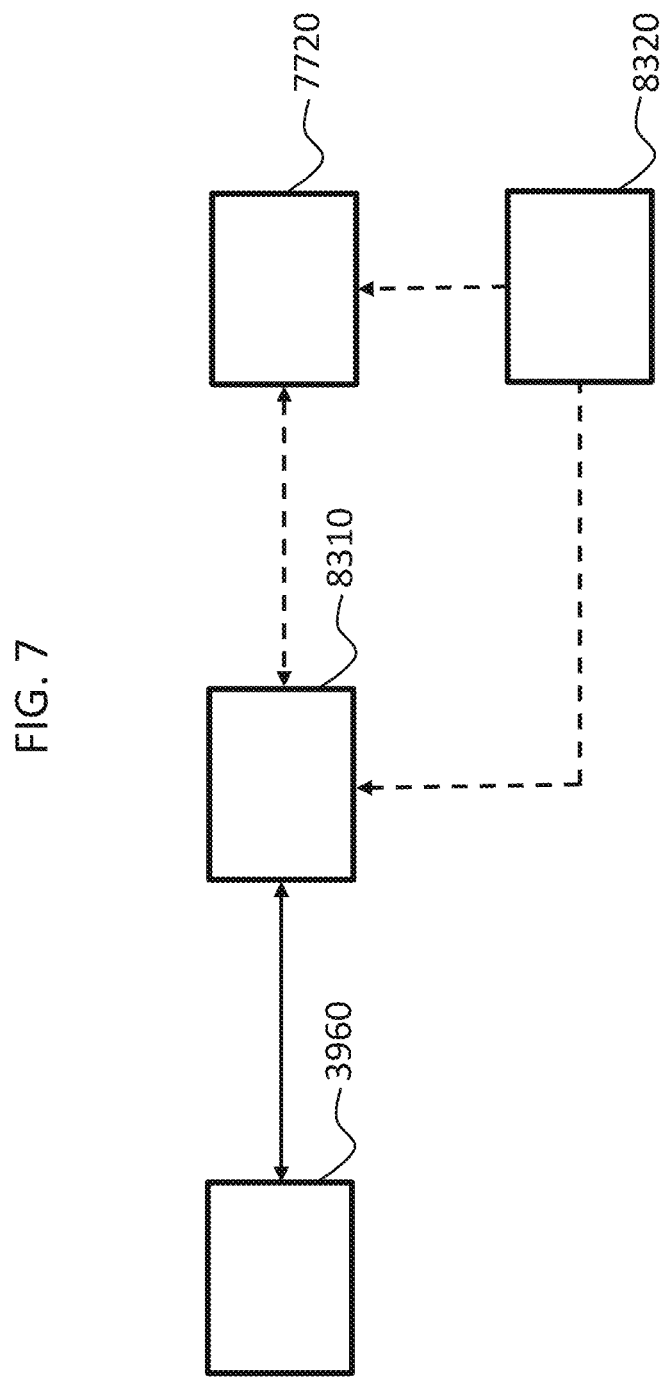

Tangent Law: The electrical current is bent at a boundary

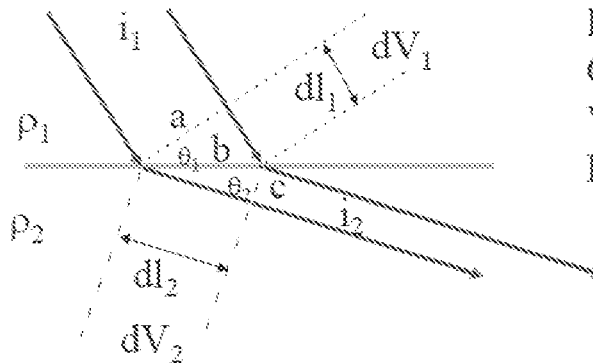

Relations:
Current: $i_1 = i_2$
Voltage: $dV_1 = dV_2$
Resistivity: $\rho_1 > \rho_2$ $$\boxed{\frac{\rho_2}{\rho_1} = \frac{\tan\theta_1}{\tan\theta_2}}$$

If $\rho_2 < \rho_1$ then the current lines will be refracted away from the normal
If $\rho_2 > \rho_1$ then the current lines will be refracted closer to the normal

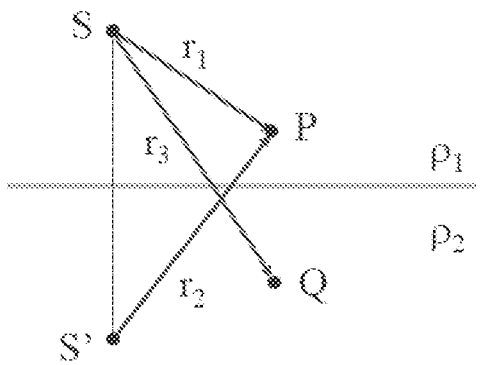

Voltages at points P and Q:

$$\boxed{V_P = \frac{I\rho_1}{4\pi}\left(\frac{1}{r_1} + \frac{k}{r_2}\right)}$$

$$\boxed{V_Q = \frac{I\rho_2}{4\pi}\left(\frac{1+k}{r_3}\right)}$$

where $k = \dfrac{\rho_2 - \rho_1}{\rho_2 + \rho_1}$

Boundary Conditions

1. $i_z = 0\big|_{z=0}$ — No current at surface
2. $V_1 = V_2$ at $z = z_{interface}$ — Voltage is continuous
3. $\dfrac{1}{\rho_1}\dfrac{\partial V_1}{\partial z} = \dfrac{1}{\rho_2}\dfrac{\partial V_2}{\partial z}$ at $z = z_{interface}$ — Normal current density is continuous
4. $V = \dfrac{i\rho_1}{2\pi(r^2 + z^2)^{\frac{1}{2}}}$ at $r = 0, z = 0$ — Particular solution

ADVANCED ELECTRODE ARRAY LOCATION EVALUATION

CROSS REFERENCE TO RELATED APPLICATIONS

This Application is a Continuation-in-Part of the following applications, and incorporates by reference and claims priority to all the subject matter therein in their entirety.
   U.S. Provisional Application No. 62/476,295, filed Mar. 24, 2017, entitled ADVANCED ELECTRODE ARRAY LOCATION EVALUATION;
   U.S. Provisional Application No. 62/559,782, filed Sep. 18, 2017, entitled ADVANCED ELECTRODE ARRAY INSERTION WITH CONDITIONING;
   U.S. patent application Ser. No. 15/707,197, filed Sep. 18, 2017, entitled ADVANCED ELECTRODE ARRAY INSERTION WITH CONDITIONING;
   U.S. Provisional Application No. 62/633,054, filed Feb. 20, 2018, entitled ADVANCED ELECTRODE DATA ANALYSIS;
   U.S. Provisional Application No. 62/642,566, filed Mar. 13, 2018, entitled ELECTRICAL FIELD USAGE IN COCHLEAS; and
   U.S. Provisional Application No. 62/647,896, filed Mar. 26, 2018, entitled ELECTRICAL TECHNIQUES FOR BIOMARKER DETECTION IN A COCHLEA.

BACKGROUND mon Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

It is noted that in at least some instances, there is utilitarian value to fitting a hearing prosthesis to a particular recipient. In some examples of some fitting regimes, there are methods which entail a clinician or some other professional presenting sounds to a recipient of the hearing prosthesis such that the hearing prosthesis evokes a hearing percept. Information can be obtained from the recipient regarding the character of the resulting hearing percept. Based on this information, the clinician can adjust or otherwise establish settings of the hearing prosthesis such that the hearing prosthesis operates according to these settings during normal use.

It is also noted that the electrode array of the cochlear implant generally shows utilitarian results if it is inserted in a cochlea.

SUMMARY

In accordance with an exemplary embodiment, there is a method, comprising sequentially activating a plurality of respective electrode pairs of an implanted cochlear implant, at least one of the electrodes of the respective electrode pairs being a respective electrode of an electrode array implanted in a cochlea, thereby generating respective localized electric fields concurrently respectively measuring, for the plurality of activated respective electrode pairs, an electrical characteristic between the respective electrodes of the respective electrode pairs resulting from the respective localized electric fields, thereby obtaining a measurement set and determining, from the measurement set, a distance between the electrode array and a wall of the cochlea.

In accordance with another embodiment, there is a method, comprising obtaining first data by operating a first set of electrodes as a source and sink in and/or on a mammal while operating a second set of electrodes as recorder electrodes in and/or on a mammal thereby obtaining first electrical data from the second set of electrodes, obtaining second data by operating a third set of electrodes as a source and sink in and/or on the mammal, the third set being different than the first set, while operating the second set of electrodes as recorder electrodes in and/or on a mammal and thereby obtaining second electrical data from the second set of electrodes, evaluating data by evaluating the first electrical data and the second electrical data, and determining spatial positioning data based on the evaluation of the data.

In accordance with another embodiment, there is a method, comprising executing vertical electrical sounding utilizing electrodes of an electrode array of a cochlear implant located in a cochlea and determining a positional feature of the electrode array based on the vertical electrical sounding.

In accordance with another embodiment, there is a method, comprising energizing an electrode implanted in a recipient, the electrode being part of an assembly located in and/or on a recipient receiving data from one or more recording electrodes located in and/or on a recipient; and determining spatial position data of the assembly based on the received data.

In accordance with another embodiment, there is a method, comprising energizing an electrode implanted in a recipient, the electrode being part of an assembly located in and/or on a recipient, receiving data from one or more recording electrodes located in and/or on a recipient; and determining spatial position data of the assembly based on the received data.

BRIEF DESCRIPTION OF THE DRAWINGS

Embodiments are described below with reference to the attached drawings, in which:

FIGS. 3A and 3B are side and perspective views of an electrode assembly extended out of an embodiment of an insertion sheath of the insertion guide illustrated in FIG. 2;

FIGS. 4A-4E are simplified side views depicting the position and orientation of a cochlear implant electrode assembly insertion guide tube relative to the cochlea at each of a series of successive moments during an exemplary implantation of the electrode assembly into the cochlea;

FIG. 6 is a cross-sectional view of a conventional electrode assembly;

FIG. 7 depicts an exemplary functional diagram of an exemplary embodiment;

FIG. 54 presents a chart of conceptual data;

FIG. 57 presents some schematics and some details associated with a theory of operation of an embodiment;

DETAILED DESCRIPTION

Figure 1:
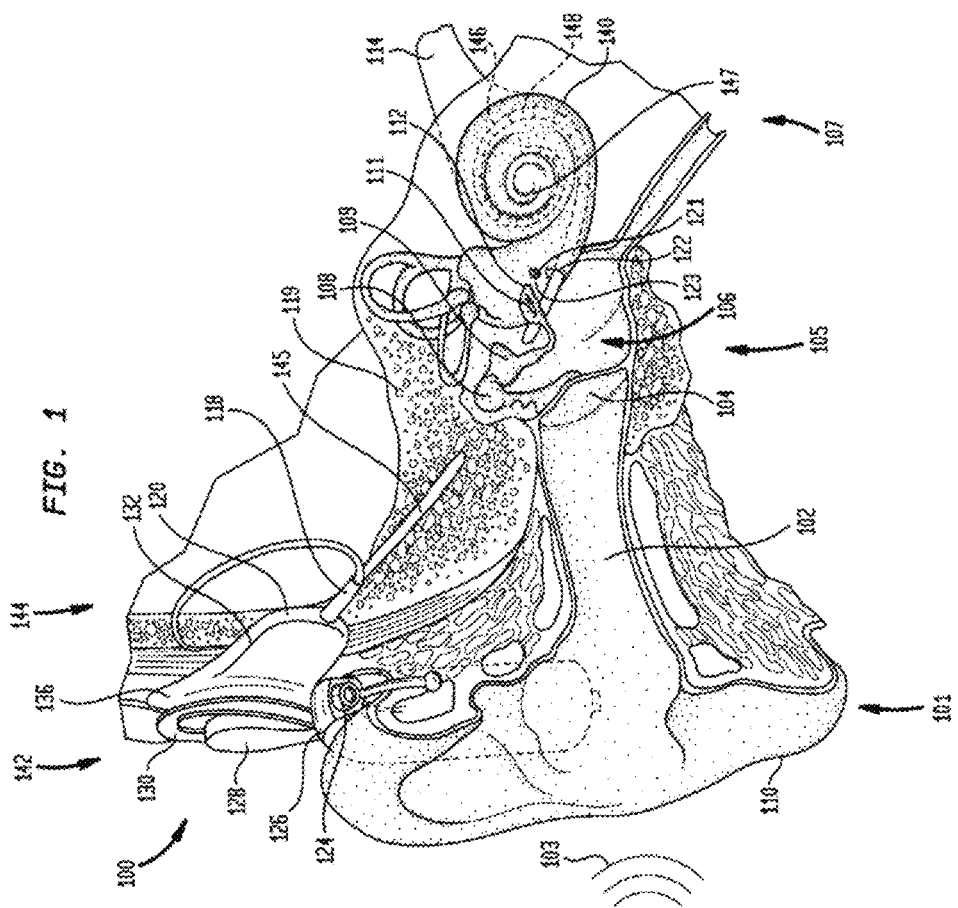
FIG. 1 is a perspective view of an exemplary hearing prosthesis in which at least some of the teachings detailed herein are applicable.

FIG. 1 is a perspective view of an exemplary cochlear implant 100 implanted in a recipient having an outer ear 101, a middle ear 105, and an inner ear 107. In a fully functional ear, outer ear 101 comprises an auricle 110 and an ear canal 102. Acoustic pressure or sound waves 103 are collected by auricle 110 and channeled into and through ear canal 102. Disposed across the distal end of ear canal 102 is a tympanic membrane 104 that vibrates in response to sound waves 103. This vibration is coupled to oval window or fenestra ovalis 112 through the three bones of the middle ear 105, collectively referred to as the ossicles 106, and comprising the malleus 108, the incus 109, and the stapes 111. Ossicles 106 filter and amplify the vibrations delivered by tympanic membrane 104, causing oval window 112 to articulate, or vibrate. This vibration sets up waves of fluid motion of the perilymph within cochlea 140. Such fluid motion, in turn, activates hair cells (not shown) inside the cochlea which in turn causes nerve impulses to be generated which are transferred through spiral ganglion cells (not shown) and auditory nerve 114 to the brain (also not shown) where they are perceived as sound.

The exemplary cochlear implant illustrated in FIG. 1 is a partially implanted stimulating medical device. Specifically, cochlear implant 100 comprises external components 142 attached to the body of the recipient, and internal or implantable components 144 implanted in the recipient. External components 142 typically comprise one or more sound input elements for detecting sound, such as microphone 124, a sound processor (not shown), and a power source (not shown). Collectively, these components are housed in a behind-the-ear (BTE) device 126 in the example depicted in FIG. 1. External components 142 also include a transmitter unit 128 comprising an external coil 130 of a transcutaneous energy transfer (TET) system. Sound processor 126 processes the output of microphone 124 and generates encoded stimulation data signals which are provided to external coil 130.

Internal components 144 comprise an internal receiver unit 132 including a coil 136 of the TET system, a stimulator unit 120, and an elongate stimulating lead assembly 118. Internal receiver unit 132 and stimulator unit 120 are hermetically sealed within a biocompatible housing commonly referred to as a stimulator/receiver unit. Internal coil 136 of receiver unit 132 receives power and stimulation data from external coil 130. Stimulating lead assembly 118 has a proximal end connected to stimulator unit 120, and extends through mastoid bone 119. Lead assembly 118 has a distal region, referred to as electrode assembly 145, a portion of which is implanted in cochlea 140.

Electrode assembly 145 can be inserted into cochlea 140 via a cochleostomy 122, or through round window 121, oval window 112, promontory 123, or an opening in an apical turn 147 of cochlea 140. Integrated in electrode assembly 145 is an array 146 of longitudinally-aligned and distally extending electrode contacts 148 for stimulating the cochlea by delivering electrical, optical, or some other form of energy. Stimulator unit 120 generates stimulation signals each of which is delivered by a specific electrode contact 148 to cochlea 140, thereby stimulating auditory nerve 114.

Figure 2:
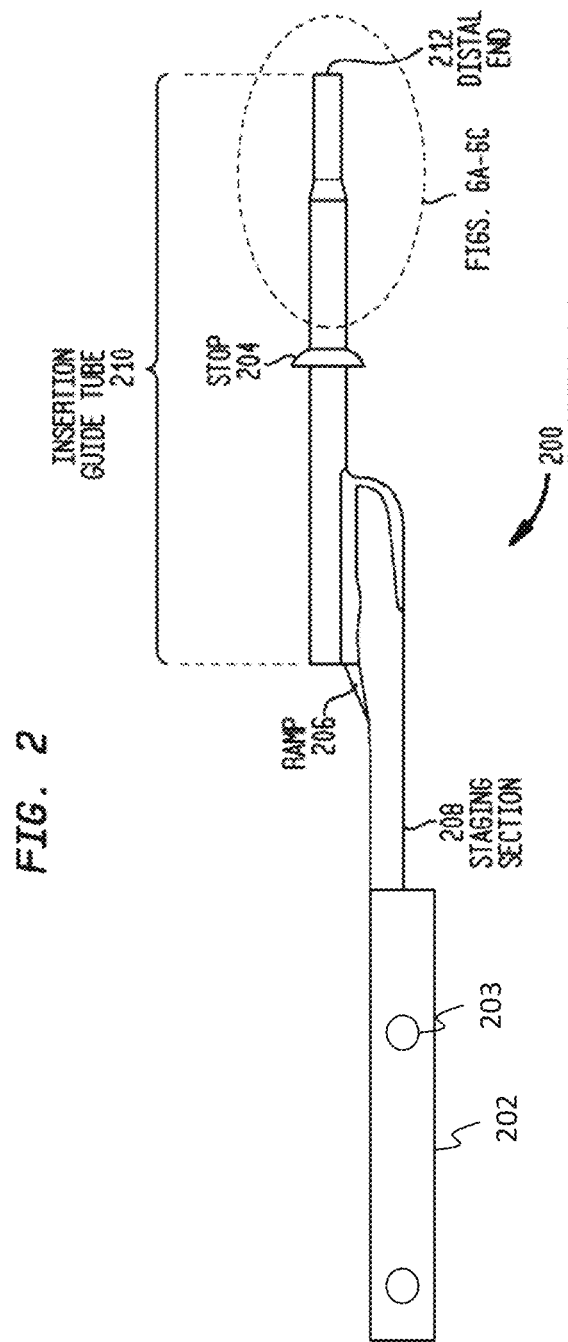
FIG. 2 is a side view of an embodiment of an insertion guide for implanting a cochlear implant electrode assembly such as the electrode assembly illustrated in FIG. 1.

Electrode assembly 145 may be inserted into cochlea 140 with the use of an insertion guide. FIG. 2 is a side view of an embodiment of an insertion guide for implanting an elongate electrode assembly generally represented by electrode assembly 145 into a mammalian cochlea, represented by cochlea 140. The illustrative insertion guide, referred to herein as insertion guide 200, includes an elongate insertion guide tube 210 configured to be inserted into cochlea 140 and having a distal end 212 from which an electrode assembly is deployed. Insertion guide tube 210 has a radially-extending stop 204 that may be utilized to determine or otherwise control the depth to which insertion guide tube 210 is inserted into cochlea 140.

Insertion guide tube 210 is mounted on a distal region of an elongate staging section 208 on which the electrode assembly is positioned prior to implantation. A robotic arm adapter 202 is mounted to a proximal end of staging section 208 to facilitate attachment of the guide to a robot, which adapter includes through holes 203 through which bolts can be passed so as to bolt the guide 200 to a robotic arm, as will be detailed below. During use, electrode assembly 145 is advanced from staging section 208 to insertion guide tube 210 via ramp 206. After insertion guide tube 210 is inserted to the appropriate depth in cochlea 140, electrode assembly 145 is advanced through the guide tube to exit distal end 212 as described further below.

FIGS. 3A and 3B are side and perspective views, respectively, of representative electrode assembly 145, which electrode array is utilized, in some embodiments, to execute some of the method actions detailed herein vis-à-vis source and/or sink and/or recorder electrodes. As noted, electrode assembly 145 comprises an electrode array 146 of electrode contacts 148. Electrode assembly 145 is configured to place electrode contacts 148 in close proximity to the ganglion cells in the modiolus. Such an electrode assembly, commonly referred to as a perimodiolar electrode assembly, is manufactured in a curved configuration as depicted in FIGS. 3A and 3B. When free of the restraint of a stylet or insertion guide tube, electrode assembly 145 takes on a curved configuration due to it being manufactured with a bias to curve, so that it is able to conform to the curved interior of cochlea 140. As shown in FIG. 3B, when not in cochlea 140, electrode assembly 145 generally resides in a plane 350 as it returns to its curved configuration. That said, it is noted that embodiments of the insertion guides detailed herein and/or variations thereof can be applicable to a so-called straight electrode array, which electrode array does not curl after being free of a stylet or insertion guide tube etc., but instead remains straight FIGS. 4A-4E are a series of side-views showing consecutive exemplary events that occur in an exemplary implantation of electrode assembly 145 into cochlea 140. Initially, electrode assembly 145 and insertion guide tube 310 are assembled. For example, electrode assembly 145 is inserted (slidingly or otherwise) into a lumen of insertion guide tube 300. The combined arrangement is then inserted to a predetermined depth into cochlea 140, as illustrated in FIG. 4A. Typically, such an introduction to cochlea 140 is achieved via cochleostomy 122 (FIG. 1) or through round window 121 or oval window 112. In the exemplary implantation shown in FIG. 4A, the combined arrangement of electrode assembly 145 and insertion guide tube 300 is inserted to approximately the first turn of cochlea 140.

As shown in FIG. 4A, the combined arrangement of insertion guide tube 300 and electrode assembly 145 is substantially straight. This is due in part to the rigidity of insertion guide tube 300 relative to the bias force applied to the interior wall of the guide tube by pre-curved electrode assembly 145. This prevents insertion guide tube 300 from bending or curving in response to forces applied by electrode assembly 145, thus enabling the electrode assembly to be held straight, as will be detailed below.

As noted, electrode assembly 145 is biased to curl and will do so in the absence of forces applied thereto to maintain the straightness. That is, electrode assembly 145 has a memory that causes it to adopt a curved configuration in the absence of external forces. As a result, when electrode assembly 145 is retained in a straight orientation in guide tube 300, the guide tube prevents the electrode assembly from returning to its pre-curved configuration. This induces stress in electrode assembly 145. Pre-curved electrode assembly 145 will tend to twist in insertion guide tube 300 to reduce the induced stress. In the embodiment configured to be implanted in scala tympani of the cochlea, electrode assembly 145 is pre-curved to have a radius of curvature that approximates the curvature of medial side of the scala tympani of the cochlea. Such embodiments of the electrode assembly are referred to as a perimodiolar electrode assembly, and this position within cochlea 140 is commonly referred to as the perimodiolar position. In some embodiments, placing electrode contacts in the perimodiolar position provides utility with respect to the specificity of electrical stimulation, and can reduce the requisite current levels thereby reducing power consumption.

As shown in FIGS. 4B-4D, electrode assembly 145 may be continually advanced through insertion guide tube 300 while the insertion sheath is maintained in a substantially stationary position. This causes the distal end of electrode assembly 145 to extend from the distal end of insertion guide tube 300. As it does so, the illustrative embodiment of electrode assembly 145 bends or curves to attain a perimodiolar position, as shown in FIGS. 4B-4D, owing to its bias (memory) to curve. Once electrode assembly 145 is located at the desired depth in the scala tympani, insertion guide tube 300 is removed from cochlea 140 while electrode assembly 145 is maintained in a stationary position. This is illustrated in FIG. 4E.

Conventional insertion guide tubes typically have a lumen dimensioned to allow the entire tapered electrode assembly to travel through the guide tube. Because the guide tube is able to receive the relatively larger proximal region of the electrode assembly, there will be a gap between the relatively smaller distal region of the electrode assembly and the guide tube lumen wall. Such a gap allows the distal region of the electrode assembly to curve slightly until the assembly can no longer curve due to the lumen wall.

Returning to FIGS. 3A-3B, perimodiolar electrode assembly 145 is pre-curved in a direction that results in electrode contacts 148 being located on the interior of the curved assembly, as this causes the electrode contacts to face the modiolus when the electrode assembly is implanted in or adjacent to cochlea 140. Insertion guide tube 500 retains electrode assembly 145 in a substantially straight configuration, thereby preventing the assembly from taking on the configuration shown in FIG. 3B. The inability of electrode assembly 145 to curve to accommodate the bias force induces stress in the assembly. Pre-curved electrode assembly 145 will tend to twist while exiting insertion guide tube 510 to reduce this stress. With the distal end of the electrode assembly curved to abut the lumen wall, the assembly twists proximally.

Figure 5A:
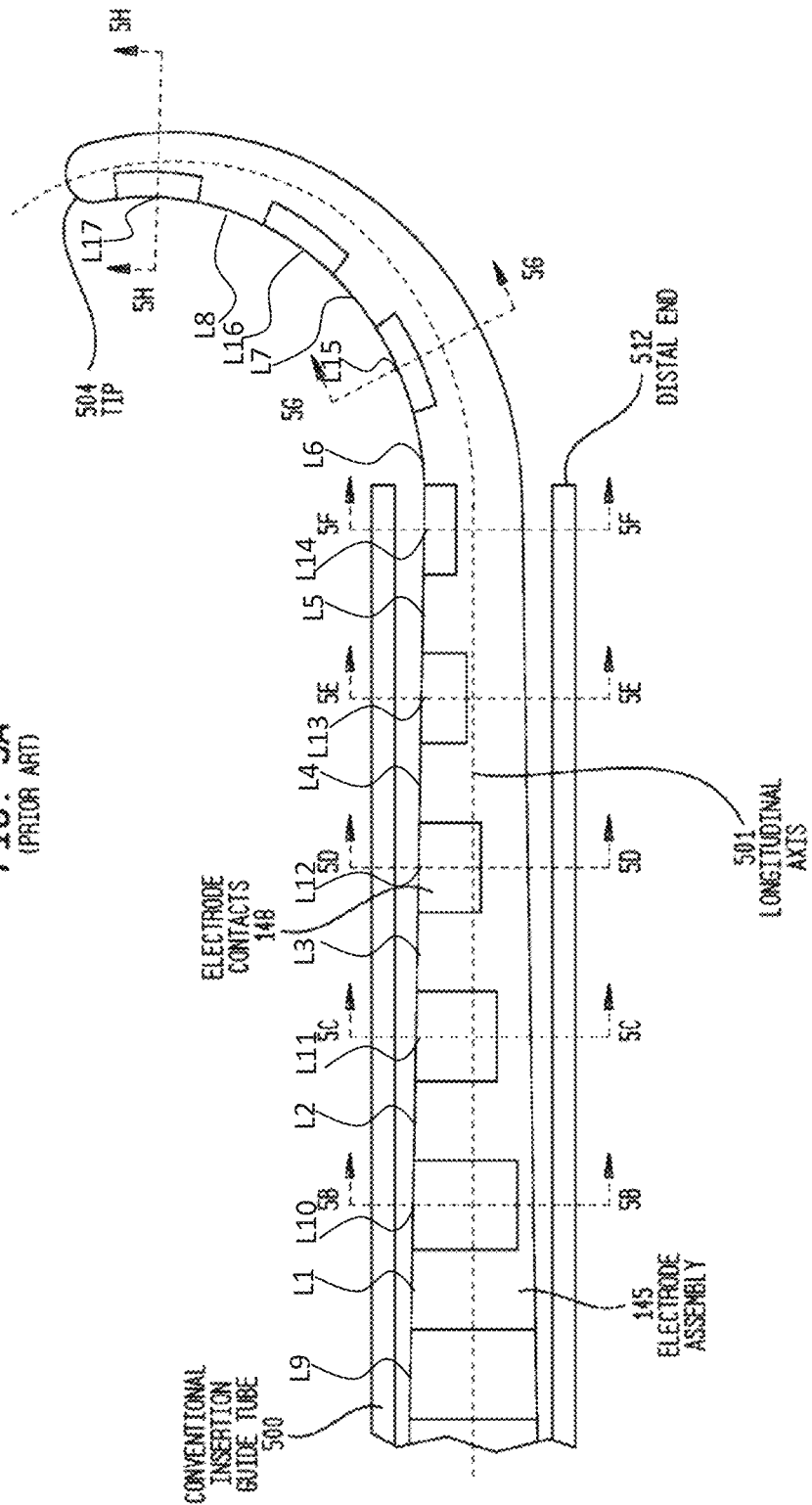
FIG. 5A is a side view of a perimodiolar electrode assembly partially extended out of a conventional insertion guide tube showing how the assembly may twist while in the guide tube.
Figure 5E:
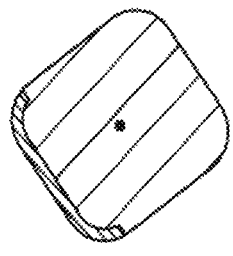
FIGS. 5B-5I are cross-sectional views of the electrode assembly illustrated in FIG. 5A.
Figure 5D:
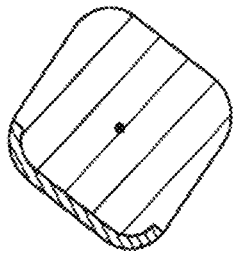
Figure 5C:
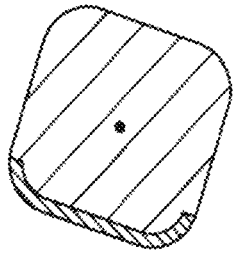
Figure 5B:
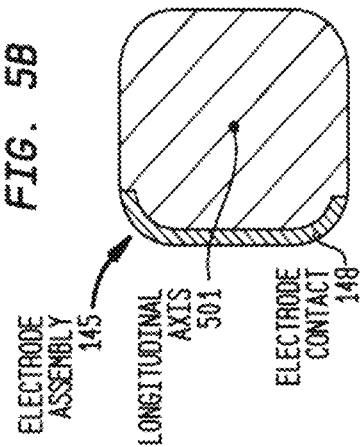
Figure 5I:
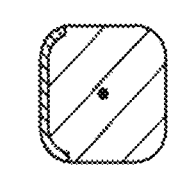
Figure 5H:
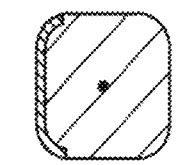
Figure 5G:
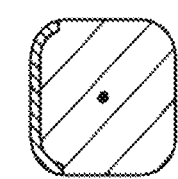
Figure 5F:
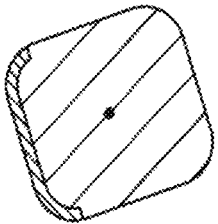

This is illustrated in FIGS. 5A-5I. FIG. 5A is a side view of perimodiolar electrode assembly 145 partially extended out of a conventional insertion guide tube 500, showing how the assembly may twist while in the guide tube. FIGS. 5B-5F are cross-sectional views taken through respective sections 5B-5B, 5C-5C, 5D-5D, 5E-5E, and 5F-5F of electrode assembly 145 in FIG. 5A.

As shown in FIGS. 5A-5F, the portion of electrode assembly 145 in insertion guide tube 510 is twisted about its longitudinal axis, resulting in electrode contacts 148 in the twisted region to have a different radial position relative to insertion guide tube 510. As shown in FIGS. 5A and 5G-I, as electrode assembly 145 exists insertion guide tube 500, the assembly is free to curve in accordance with its bias force. However, the orientation of electrode contacts in the deployed region of the assembly is adversely affected by the twisted region of the assembly remaining in guide tube 510.

Accordingly, the insertion guide can have an insertion guide tube that maintains a perimodiolar or other pre-curved electrode assembly in a substantially straight configuration while preventing the electrode assembly from twisting in response to stresses induced by the bias force which urges the assembly to return to its pre-curved configuration. This generally ensures that when the electrode assembly is deployed from the distal end of the insertion guide tube, the electrode assembly and insertion guide tube have a known relative orientation.

As shown in FIG. 6, electrode assembly 145 has a rectangular cross-sectional shape, with the surface formed in part by the surface of the electrode contact, referred to herein as top surface 650, and the opposing surface, referred to herein as bottom surface 652, are substantially planar. To be clear, it is noted that the electrode assembly/electrode array shown in the figures is but an exemplary embodiment, and in other embodiments, a round, oval, etc., shaped electrode array, straight or curved, can be used.

More particularly, as will now be detailed, in some exemplary embodiments, the electrode array is utilized to obtain data regarding electrode array position within the cochlea, such as by way of example only and not by way of limitation, position information indicating relative location to the modiolus wall. FIG. 7 depicts an exemplary system for utilizing the cochlear implant to obtain such information. Presented in functional terms, there is a test unit 3960 in signal communication with unit 8310, which in turn is in signal communication, optionally with a unit 7720 and a unit 8320, the details of which will be described below.

Figure 8:
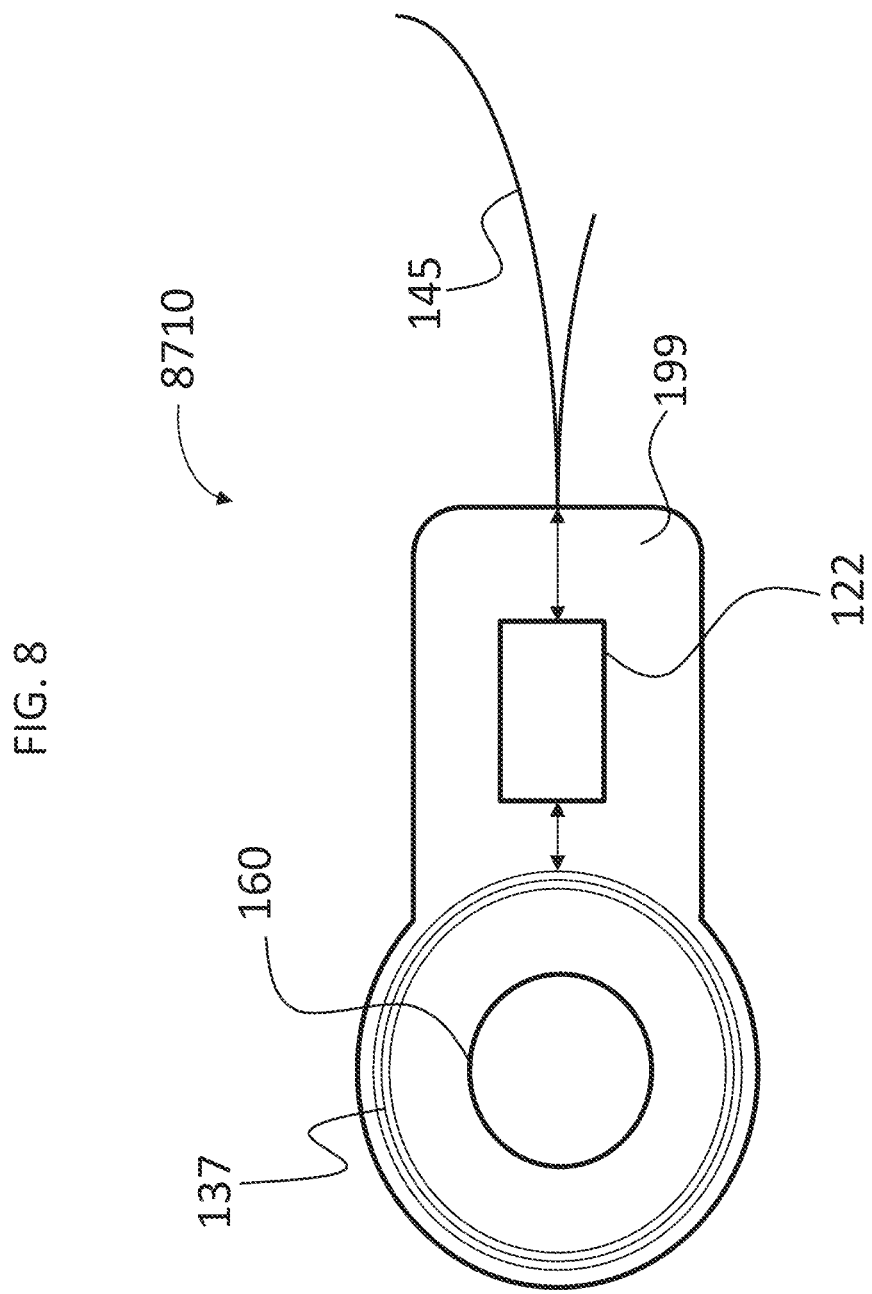
FIG. 8 depicts an exemplary implantable component of a cochlear implant according to an exemplary embodiment.

Unit 3960 can correspond to an implantable component of a cochlear implant, as seen in FIG. 8. More specifically, FIG. 8 depicts an exemplary high-level diagram of a receiver/stimulator 8710 of a cochlear implant, looking downward. As can be seen, the receiver/stimulator 8710 includes a magnet 160 that is surrounded by a coil 137 that is in two-way communication (although in other embodiments, the communication is one-way) with a stimulator unit 122, which in turn is in communication with the electrode array 145. Receiver/stimulator 8710 further includes a cochlear stimulator unit 122, in signal communication with the coil 137. The coil 137 and the stimulator unit 122 are encased in silicon as represented by element 199. In an exemplary embodiment, receiver/stimulator 8710 is utilized as test unit 3960, and is used to acquire information about electrode array position.

Figure 9:
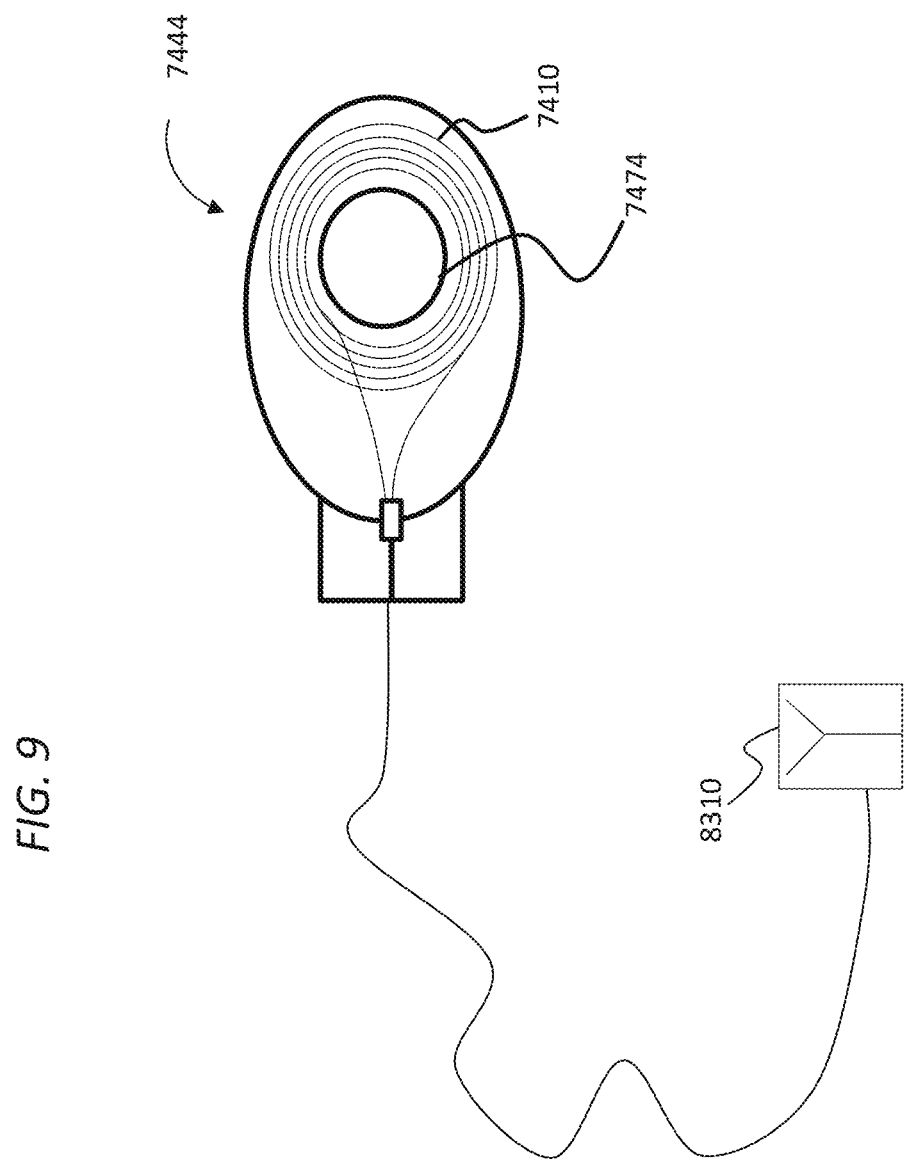
FIG. 9 depicts a component that places the cochlear implant of FIG. 8 into signal communication with another component.

FIG. 9 depicts an exemplary RS (receiver/stimulator) interface 7444 which is presented by way of concept. An inductance coil 7410 is configured to establish a magnetic inductance field so as to communicate with the corresponding coil of the receiver-stimulator of the cochlear implant. Interface 7444 includes a magnet 7474 so as to hold the inductance coil 7410 against the coil of the receiver/stimulator of the cochlear implant in a manner analogous to how the external component of the cochlear implant is held against the implanted component, and how the coils of those respective components are aligned with one another. As can be seen, an electrical lead extends from the coil 7410 to control unit 8310, representing signal communication between interface 7444, and control unit 8310.

Figure 10:
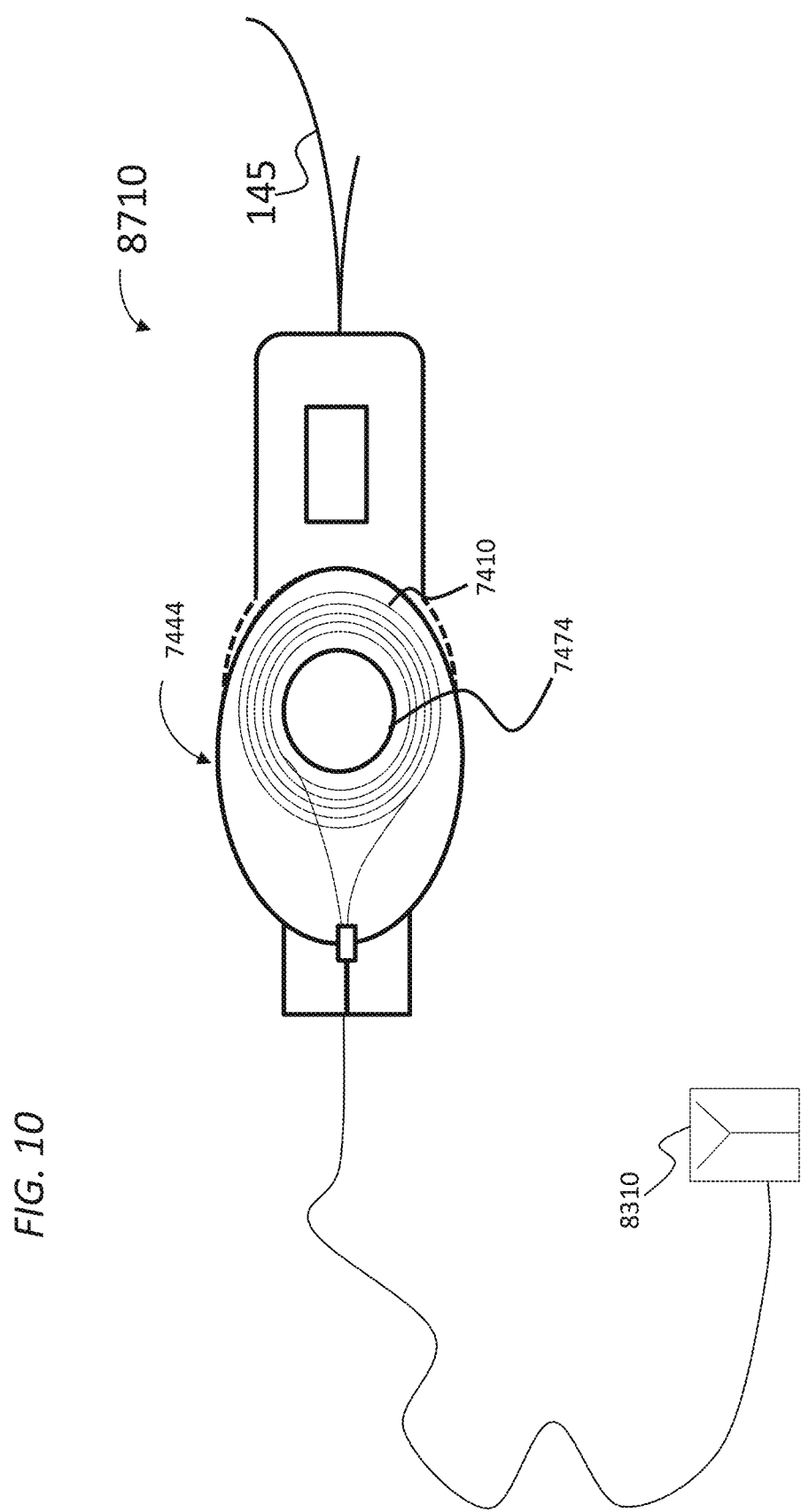
FIG. 10 depicts the cochlear implant of FIG. 8 in signal communication with a communication device that enables communication between the cochlear implant and a control unit according to an exemplary embodiment.
Figure 11:
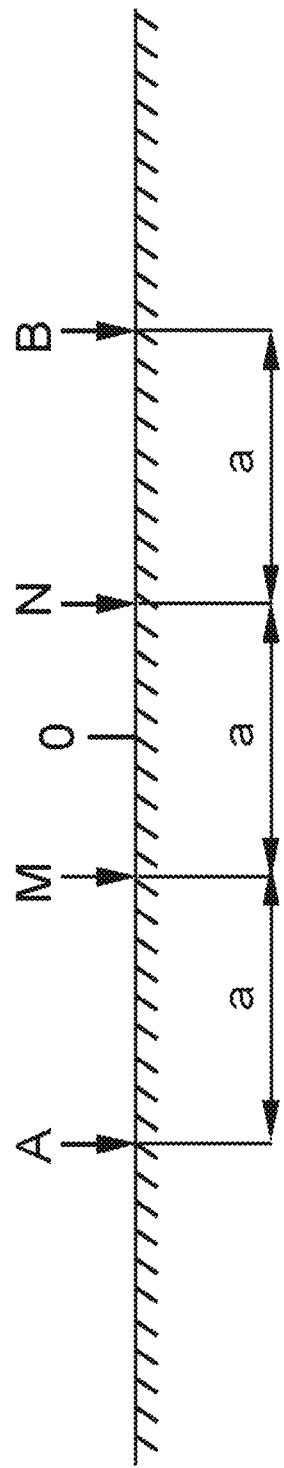
FIGS. 11-14 depict some exemplary arrangements of source and sink and recorder electrodes in a functional manner for conceptual purposes.
Figure 12:
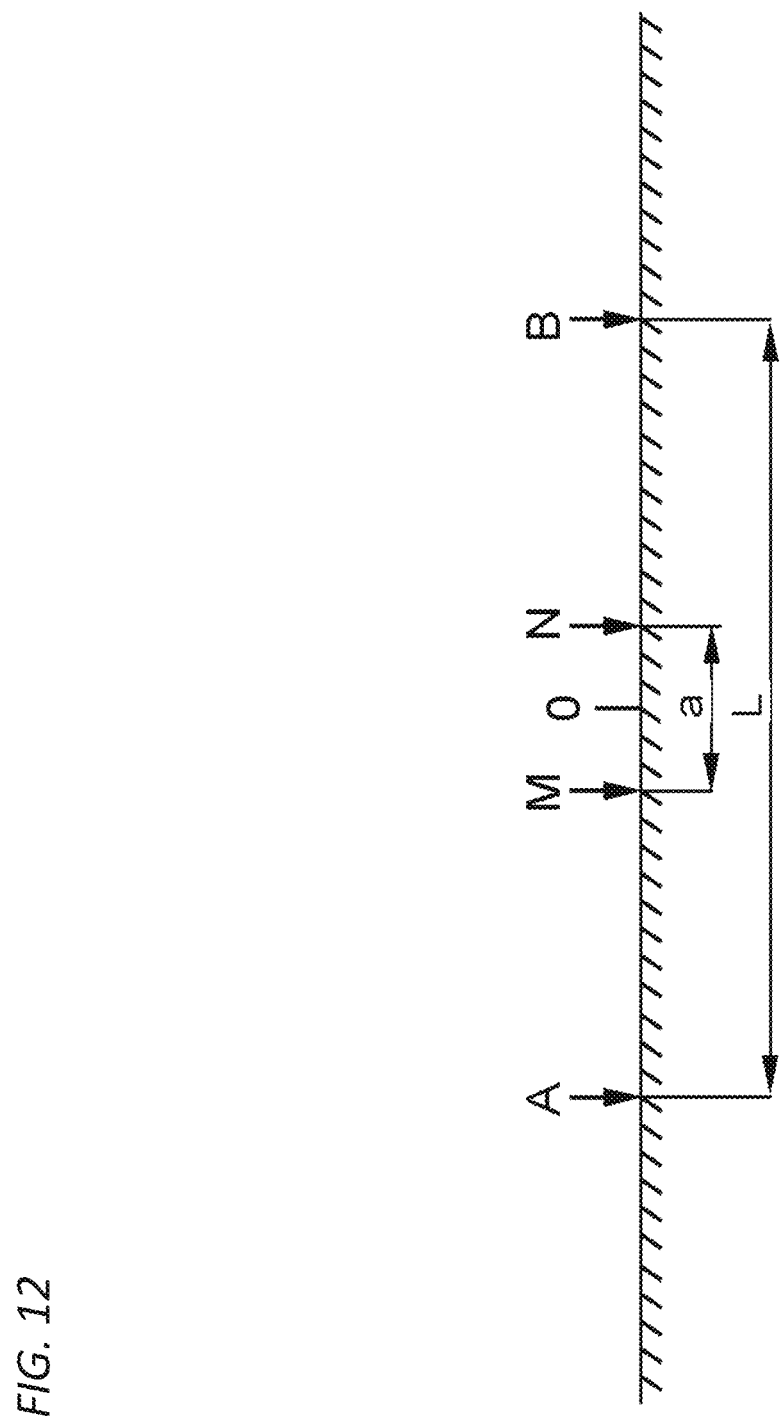
Figure 13:
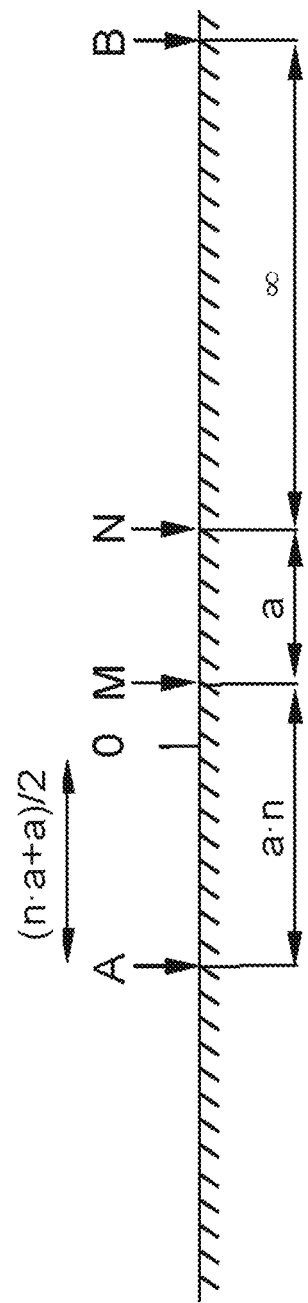
Figure 14:
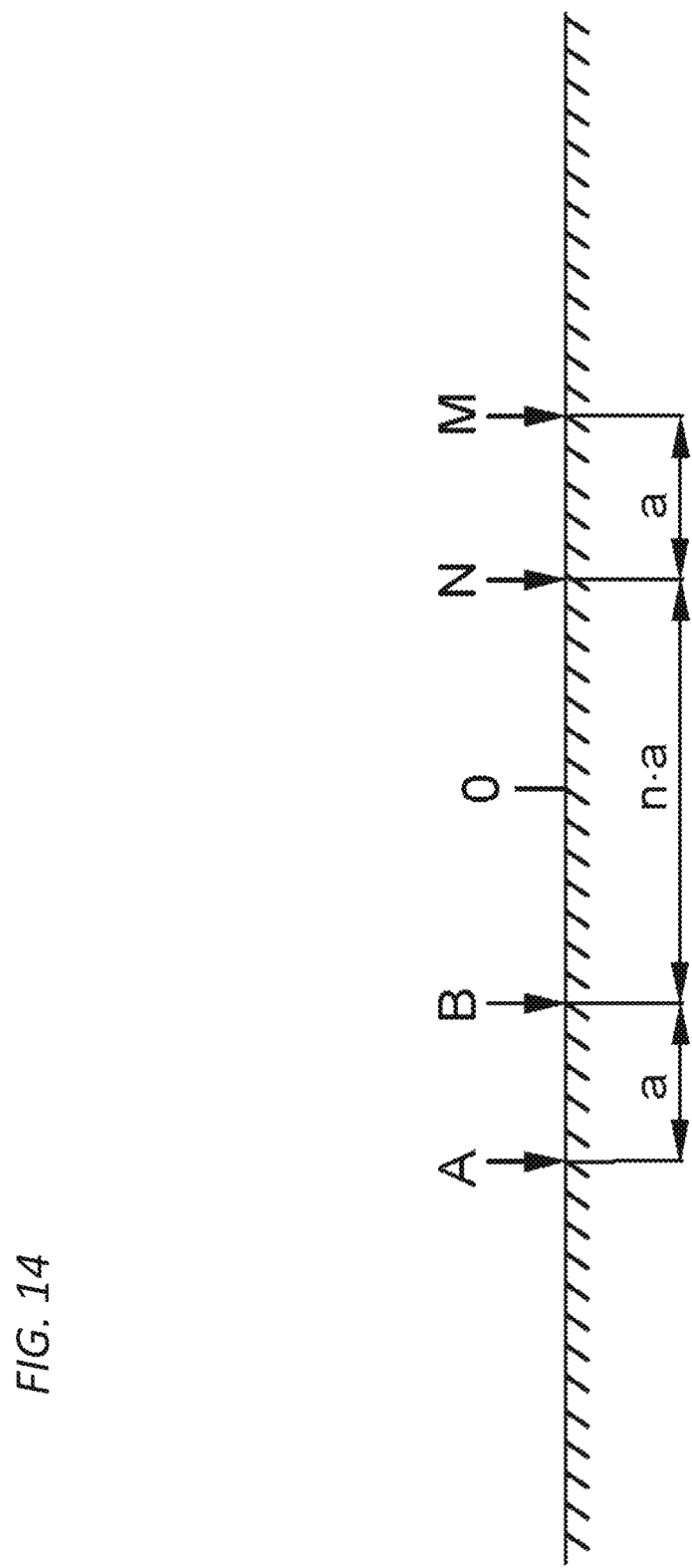

FIG. 10 depicts an exemplary embodiment of the receiver/stimulator 8710 in signal communication with the control unit 8310 via electrical lead that extends from the interface device 7444 having coil 7410 about a magnet 7474 as can be seen. The interface device 7444 communicates via an inductance field with the inductance coil of the receiver/stimulator 8710 so that the data acquired by the implantable component 8710 (receiver/stimulator) can be transferred to the control unit 8310.

Note also that in at least some alternate exemplary embodiments, control unit 8310 can communicate with the so-called "hard ball" reference electrode of the implantable component of the cochlear implant so as to enable communication of data from the receiver/stimulator 8710 to control unit 8310 and/or vice versa.

It is noted that in the embodiment of FIG. 10, control unit 8310 is in signal communication with the various other components as detailed herein, which components are not depicted in FIG. 10 for purposes of clarity.

Also functionally depicted in FIG. 7 is the optional embodiment where an electrode array insertion robotic system/actuator system 7720 and an input device 8320 is included in the system. In an exemplary embodiment, the input device 8320 could be a trigger of a hand held device that controls the actuator system 7720 and can stop and/or start insertion of the electrode array. In an exemplary embodiment, the input device 8320 could be a trigger on the tool 8200.

Control unit 8310 can be a signal processor or the like or a personal computer or the like or a mainframe computer or the like etc., that is configured to receive signals from the test unit 3960 and analyze those signals to evaluate an insertion status of the electrode array. More particularly, the control unit 8310 can be configured with software the like to analyze the signals from test unit 3960 in real time and/or in near real time as the electrode array is being advanced into the cochlea by actuator assembly 7720 (if present, and if not present, while the array is being inserted/advanced by hand). The control unit 8310 analyzes the input from test unit 3960 as the electrode array advanced by the actuator assembly 7720 and evaluates the input to determine if there exists an undesirable insertion status of the electrode array and/or evaluates the input to determine if the input indicates that a scenario could occur or otherwise there exists data in the input that indicates that a scenario is more likely to occur relative to other instances where the insertion status of the electrode array will become undesirable if the electrode array is continued to be advanced into the cochlea, all other things remaining the same (e.g., insertion angle/trajectory, etc., which can be automatically changed as well—more on this below). In an exemplary embodiment, upon such a determination, control unit 8310 could halt the advancement of the array into the cochlea by stopping the actuator(s) of actuator assembly 7720 and/or could slow the actuator(s) so as to slow rate of advancement of the electrode array into the cochlea and/or could reverse the actuator(s) so as to reverse or otherwise retract the electrode array within the cochlea (either partially or fully). Alternatively, in embodiments where actuator assembly 7720 is not present, control unit 8310 could provide an indication to the surgeon or the like to halt and/or slow the insertion, etc. In at least some exemplary embodiments, control unit 8310 can be configured to override the input from input unit 8320 input by the surgeon or the user. Control unit 8310 can be programmed to execute one or more or all of the teachings detailed herein.

Some exemplary embodiments utilize the receiver/stimulator 8710 as a test unit 3910 that enables vertical electrical sounding techniques or resistivity tomography techniques to be executed in the cochlear to determine spatial relationships (or other information—this is by way of example and not by limitation) between the electrode array and the structure of the cochlea or other structures of the recipient. In an exemplary embodiment, the receiver/stimulator 8710 is utilized to execute one or more or all of the method actions detailed below, alone or in combination with an external component of a cochlear implant, and/or with the interface 7444, which can be used after the receiver/stimulator 8710 is fully implanted in the recipient and the incision to implant such has been closed (e.g., days, weeks, months or years after the initial implantation surgery). The interface 7444 can be used to control the receiver/stimulator to execute at least some of the method actions detailed herein (while in some other embodiments, the receiver/stimulator can execute such in an autonomous or semi-autonomous manner, without being in communication with an external component) and/or can be used to obtain data from the receiver/stimulator after execution of such method actions.

More specifically, because the electrode array includes a plurality of electrodes (in some embodiments, 22 electrodes), many if not all of which can be individually used as sources and/or sinks and many if not all of which can be utilized as "read" electrodes, the techniques of vertical electrical sounding and resistivity tomography can be applied utilizing a cochlear electrode array. Briefly, while the standard technology utilizes the placement and subsequent movement of source and sink electrodes and measurement electrodes at the surface of the earth to obtain information, where the relative movement is recorded so that the process can be executed, here, the different electrodes are utilized to replicate the movement feature of the vertical electrical sounding/resistivity tomography techniques.

Without being bound by theory, vertical electrical sounding (VES) is a geophysical method for investigation of a geological medium. The method is based on the estimation of the electrical conductivity or resistivity of the medium. The estimation is performed based on the measurement of voltage/electrical field induced by the distant grounded electrodes (current electrodes). FIGS. 11-14 depict some exemplary configurations of possible measurement setups. The electrodes A and B are current electrodes which are connected to a current source; N and M are potential electrodes (measurement electrodes) which are used for the voltage measurements. As source, the direct current or low frequency alternating current is used. It is noted that ture direct current sometimes can have deleterious effects on tissue, and thus in some other embodiments, instead of using direct current, embodiments approximate direct current by measuring after transient effects of a current pulse (or other AC waveform) have subsided. The interpretation of the measurements can be performed based on the apparent resistivity values. The depth of investigation can depend on the distance between the current electrodes. In some embodiments, a location of the recording pair with respect to the current electrodes can also influence the depth of investigation. For example, such can relate to a current path created by the dipole. The current can form an "arc" between the two dipoles (source/sink electrodes) with the maximum current penetration mid way between the source/sink electrodes. In some embodiments, if the measurement electrodes are adjacent one of the source/sink electrodes then the current penetration depth is less than the maximum. In order to obtain the apparent resistivity as the function of depth, the measurements for each position are performed with several different distances between current electrodes. The apparent resistivity is calculated as $$\rho_k = k \frac{U_{MN}}{I_{AB}}$$

here, k is a geometric factor, $U_{MN}$ is voltage between electrodes M and N, $I_{AB}$ is current in the line AB. The geometric factor is defined by $$k = \frac{2\pi}{\frac{1}{r_{AM}} - \frac{1}{r_{BM}} - \frac{1}{r_{AN}} + \frac{1}{r_{BN}}}$$

here r is the distance between electrodes.

It is noted that in some embodiments, the numerator for the geometric factor is $4\pi$, as the equations above are for a hemisphere (i.e. the air acts as an insulation on one side of the array for geophysical applications).

The equation here is for a hemisphere (i.e. the air acts as an insulation on one side of the array for geophysical applications). In some embodiments, interpretation of gathered data is performed based on the dependency $\rho_k(AB/2)$. The application of large electrode arrays allows for reconstructing complex 3D structure of geological media (such as that which results from electrical resistivity tomography). However, the interpretation of such measurement is rather difficult. In this case, advanced interpretation techniques based on numerical methods can be applied.

Some embodiments utilize the basic idea is that voltage equals the charge divided the value that equals 4 times pie times the square of the distance from the source times the resistance (or impedance). Conversely, the electric fields differential of the voltage gradient drops off at a rate of 1 over the distance cubed (as opposed to the voltage fall-off at a rate of 1 over the distance squared). (It is briefly noted that the term resistance is sometimes used herein with respect to impedance and visa-versa. Any disclosure of a resistance/resistance related feature corresponds to a disclosure of an impedance/impedance related feature, and visa-versa, providing that the art enables such.)

It is noted that some embodiments detailed herein modify or otherwise adapt the VES for geological exploration to that which can be utilized for a cochlea. For example, adapting the VES teachings in the art of geological exploration to take into account that there is no air layer that prevents the current from traveling in a spherical manner (as opposed to a hemispherical manner vis-à-vis application in geological exploration). Thus, any disclosure herein for VES or the like includes a disclosure where such is modified to take into account the environment of a cochlea with (or without) perilymph therein.

Figure 15:
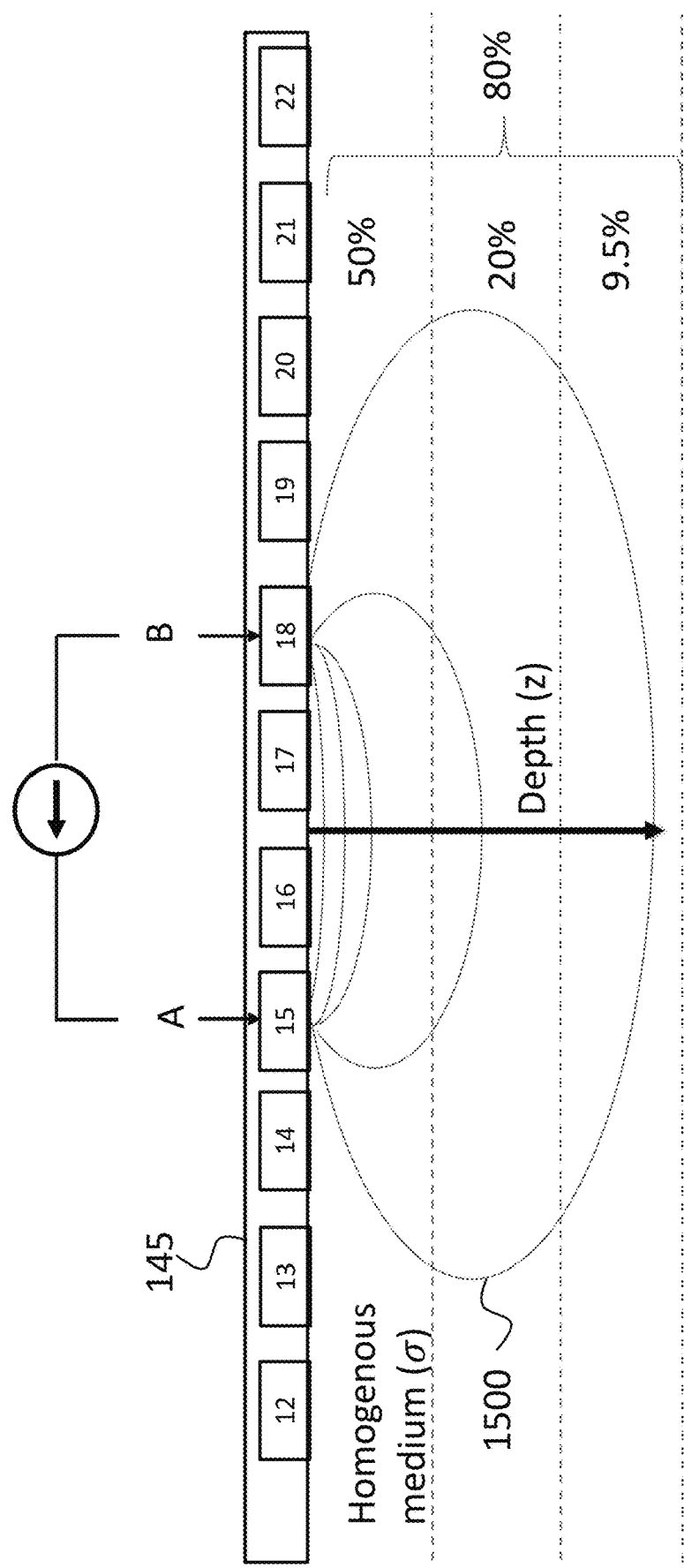
FIGS. 15-23 conceptually depict current spread in some embodiments, which current spread forms the foundation in some embodiments for the methods detailed herein.

Generally applying the above techniques to an electrode array in a cochlea, FIG. 15 functionally depicts an electrode array 145 in a cochlea, with current flow lines 1500 emanating from electrode 15 as a source A and traveling to electrode 18 as a sink B (or vice versa). (It is noted that the region above the electrode can be considered, in some embodiments, to be infinite in impedance for the demonstrated current spreads.) FIG. 15 functionally represents that the deepest current flows occur halfway between the stimulating electrode pair (electrodes 15 and 18). The amount of current flowing at depth Z reduces with the cube of the depth (where r in the above equations has been replaced by the variable Z). With respect to a unitized value based on the distance between the electrodes, the depths of the three layers depicted in FIG. 15 each correspond to one half the electrode spacing. As can be seen, 50% of the current is located in the first layer, which corresponds to the layer having a distance of half the distance between the electrodes, 20% of the current exist in the second layer, and then about 9.5% of the current exists in the third layer. (The layers are equally spaced.) The teachings herein and the calculations treat the electrodes as points for simplicity. But in other embodiments, such need not be the case. In some embodiments, one can integrate over the surface area of the electrode, to increase accuracy, and then calculate the charge distribution generated by the shape. Additionally, charge emerges from the perimeter of a conductor at high frequencies (because, in some instances, these measurements are taken 10's of μS after engaging the current source, we are measuring a high frequency response). Due to symmetry, and for simplicity the centerline to centerline can be utilitarian for a distributed conductor.

Figure 16:
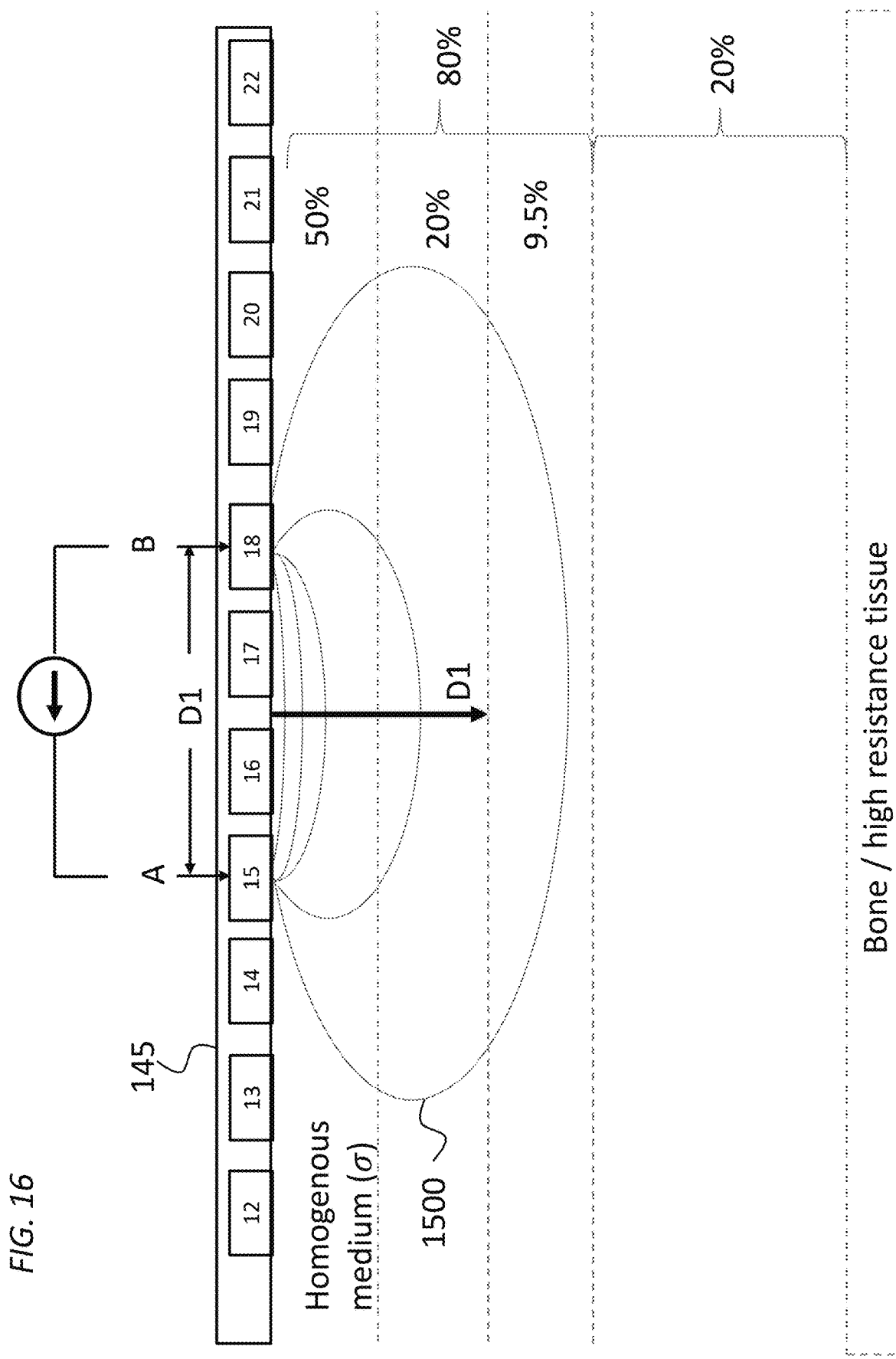

FIG. 15 depicts the electrode array 145 located in perilymph of the cochlea in general isolation from other tissue, where the impedance to electrical conduction of the perilymph is relatively low relative to other tissue of the recipient, such as for example bone. FIG. 16 depicts the electrode array 145 in perilymph, except also relative to the bony tissue of the modiolus wall, or other high-resistance tissue (high resistance relative to the perilymph)/high-impedance tissue. (It is noted that the bottom layers in which the remaining 20 or so percent of the current exists have been lumped into a single layer for convenience. In reality, there will be a plurality of layers between the third layer and the bone/high resistance tissue/high impedance tissue, each layer corresponding to a layer having a thickness of half the distance between the source and sink electrodes). FIG. 16 depicts the distance D1 which is the distance from the electrode array to the bottom of the second layer, which distance D1 corresponds to the distance between the source and the sink electrodes, which corresponds to the fact that each layer has been defined as a layer having a thickness of half of the distance D1.

The idea with FIG. 16 is that the further the electrode array 145 in general, and the source and sink electrodes in particular (and/or recording electrodes in particular) are away from the modiolus wall or other high resistive tissue, the lower the impedance to current between the source and sink electrodes. That is, because there will be more perilymph for the bulk of the electrical current to flow through relative to that which would be the case if the electrode array 145 was closer to the modiolus wall/tissue of higher resistivity relative to the perilymph, the impedance will be lower. Accordingly, FIG. 16 depicts the electrode array 145 a distance from the bone/high resistance tissue (e.g. modiolus wall) a distance where basically none of the electrical current between electrodes 15 and 18 will travel through the bone. Thus, the impedance to electrical current in the homogeneous medium (perilymph) is relatively low, and the effective impedance between the source and the sink electrodes, as determined by for example, the recording electrodes 16 and 17, will be relatively low, indicating that the bone/high resistance tissue is relatively far away from the electrodes.

For purposes of discussion, the resistivity of current flow between the source and the sink will be conceptually unitized as 1 for the arrangement of FIG. 16.

Figure 17:
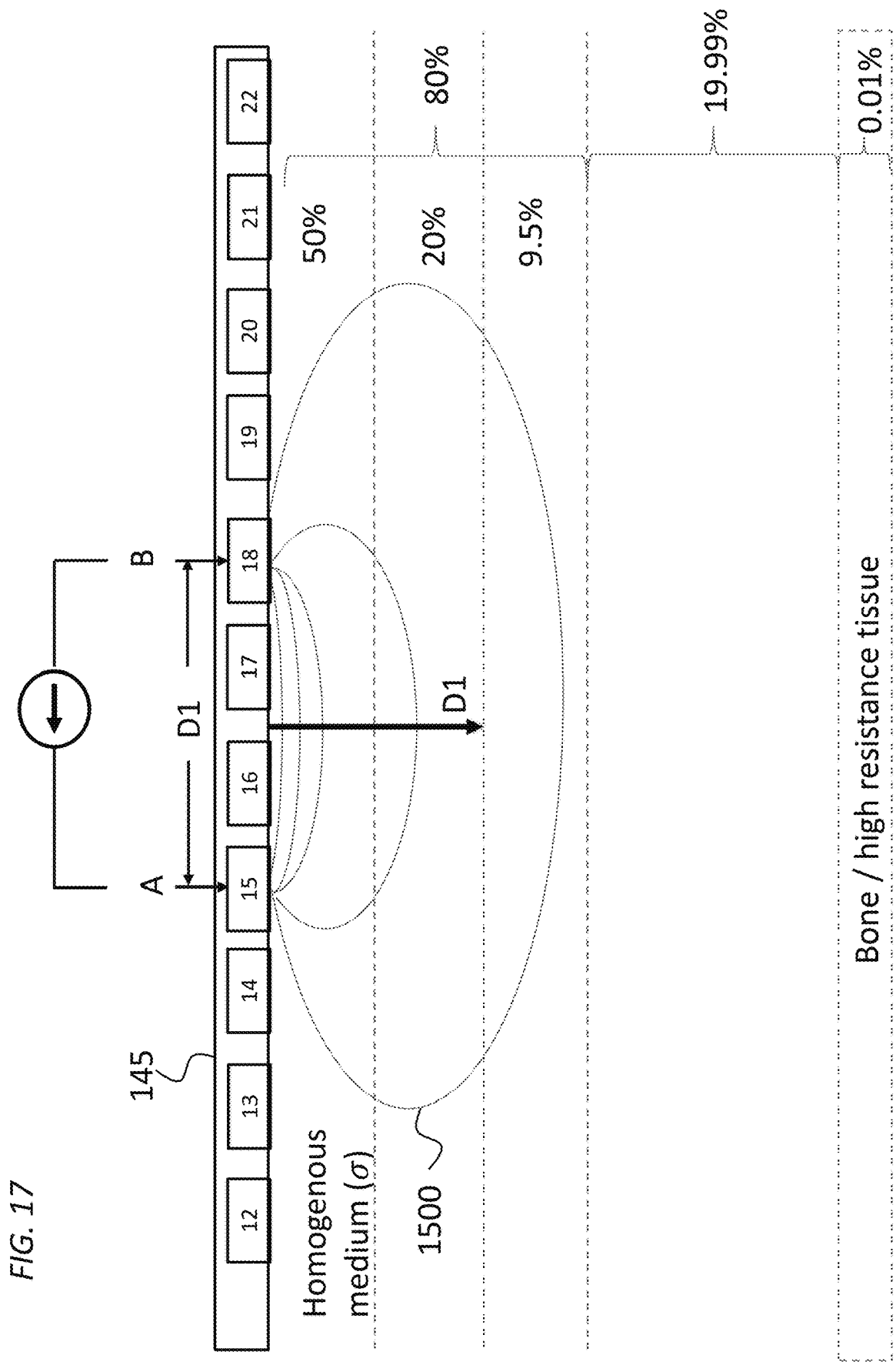

FIG. 17 schematically depicts a scenario where the electrode array 145 is located closer to the modiolus wall/the tissue of high resistivity relative to that which is the case in FIG. 16. Basically, the tissue of high resistivity is located within an area in which a recognizable percentage of the charge flows. Here, about 0.01% of the charge flows through the tissue of higher resistivity. This is a relatively minor amount. However, this changes the resistivity of the current flow between the source and sink electrodes. For purposes of discussion, the resistivity of current flow between the source and sink will be conceptually unitized as 1.1 for the arrangement of FIG. 17. In this regard, by measuring the resistivity or other electrical features of the electrode array in this arrangement, a determination can be made that the tissue of higher resistivity (e.g., modiolus wall) is closer than that which is the case for the scenario of FIG. 16.

Figure 18:
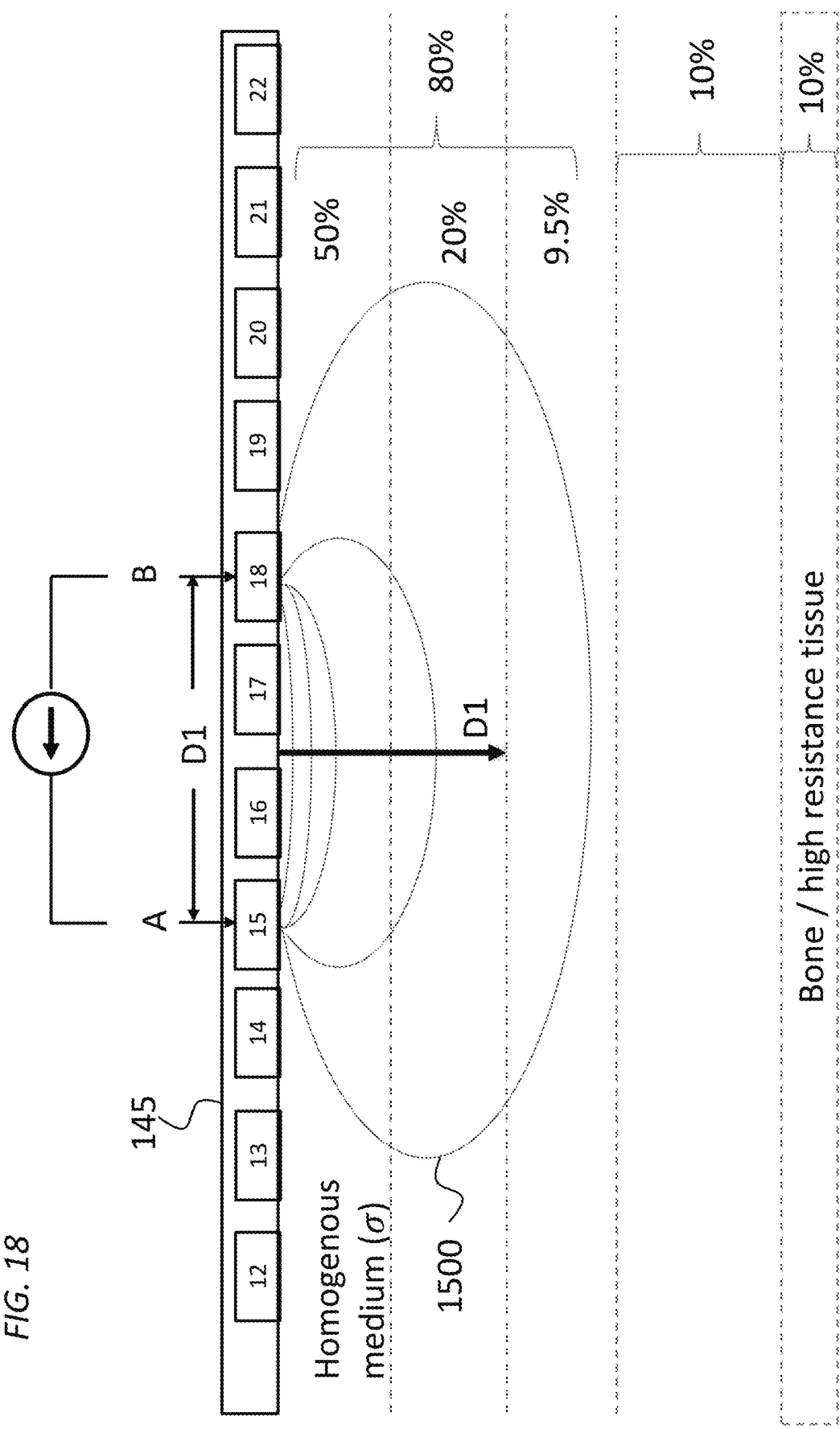

FIG. 18 schematically depicts a scenario where the electrode array 145 is located closer to the modiolus wall/the tissue of high resistivity relative to that which is the case in FIG. 17. Basically, the tissue of high resistivity is located within an area in which a recognizable percentage of the charge flows. Here, about 10% of the charge flows through the tissue of higher resistivity. This changes the resistivity of the current flow between the source and sink electrodes. For purposes of discussion, the resistivity of current flow between the source and sink will be conceptually unitized as 10 for the arrangement of FIG. 18. In this regard, by measuring the resistivity or other electrical features of the electrode array in this arrangement, a determination can be made that the tissue of higher resistivity (e.g., modiolus wall) is closer than that which is the case for the scenario of FIG. 17.

Figure 19:
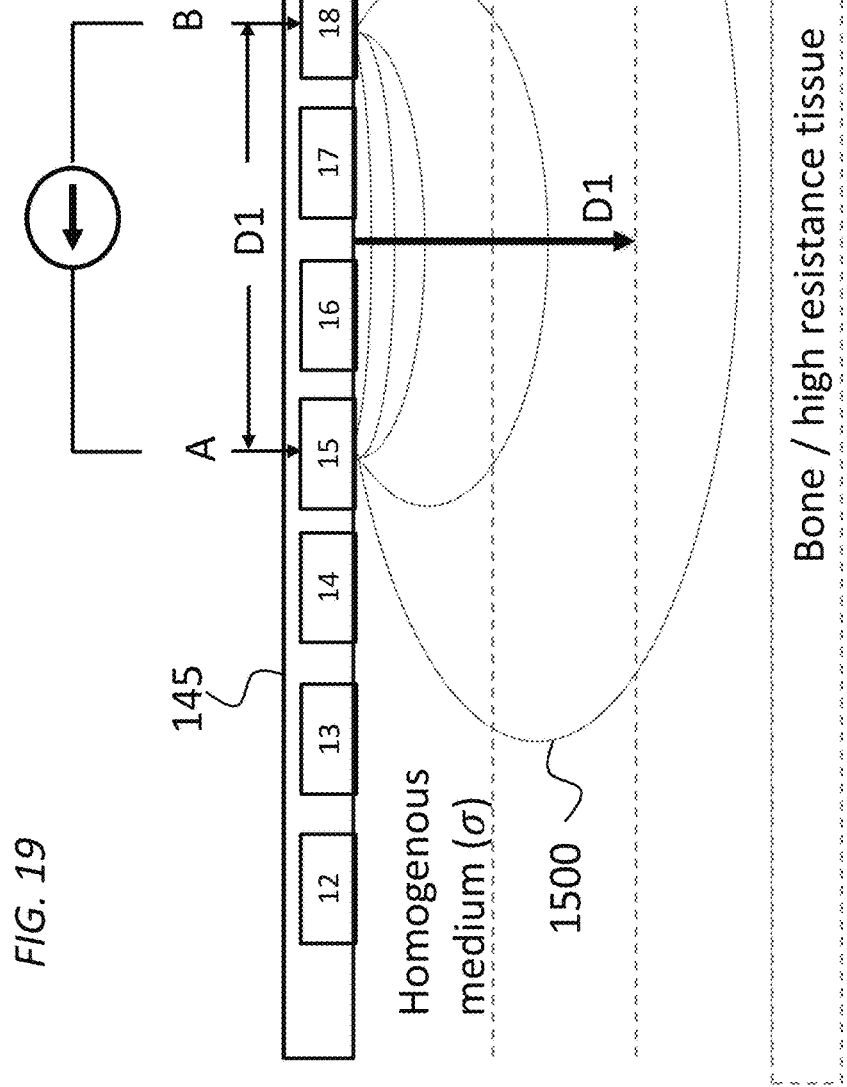

FIG. 19 schematically depicts an scenario where the electrode array 145 is located closer to the modiolus wall/the tissue of high resistivity relative to that which is the case in FIG. 18. Basically, the tissue of high resistivity is located within an area in which a recognizable percentage of the charge flows. Here, about 20.5% of the charge flows through the tissue of higher resistivity. This changes the resistivity of the current flow between the source and sink electrodes. For purposes of discussion, the resistivity of current flow between the source and sink will be conceptually unitized as 50 for the arrangement of FIG. 19. In this regard, by measuring the resistivity or other electrical features of the electrode array in this arrangement, a determination can be made that the tissue of higher resistivity (e.g., modiolus wall) is closer than that which is the case for the scenario of FIG. 18.

Figure 20:
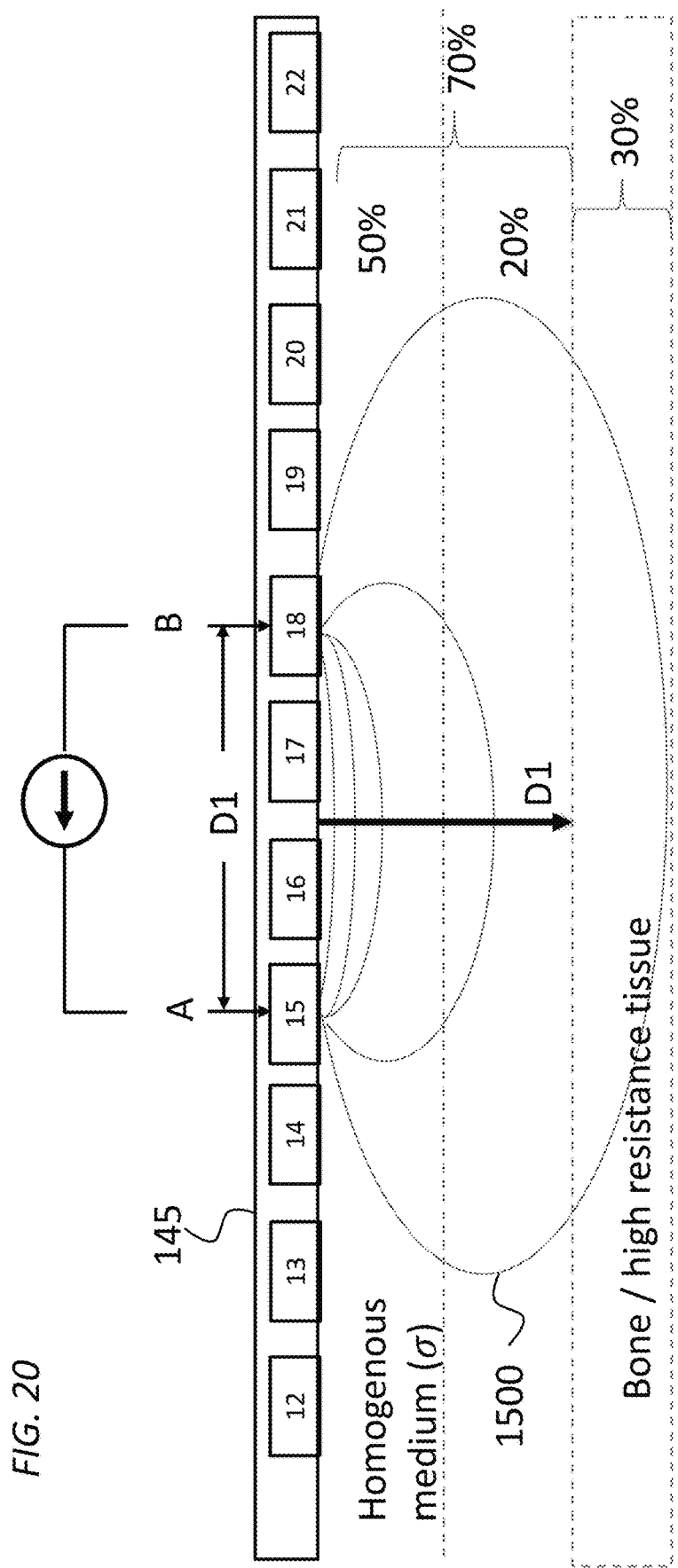

FIG. 20 schematically depicts a scenario where the electrode array 145 is located closer to the modiolus wall/the tissue of high resistivity relative to that which is the case in FIG. 19. Here, it is located at the distance D1 (the distance that equals the distance between the source and sink electrodes). Basically, the tissue of high resistivity is located within an area in which a recognizable percentage of the charge flows. Here, about 30% of the charge flows through the tissue of higher resistivity. This changes the resistivity of the current flow between the source and sink electrodes. For purposes of discussion, the resistivity of current flow between the source and sink will be conceptually unitized as 150 for the arrangement of FIG. 20. In this regard, by measuring the resistivity or other electrical features of the electrode array in this arrangement, a determination can be made that the tissue of higher resistivity (e.g., modiolus wall) is closer than that which is the case for the scenario of FIG. 18.

Figure 21:
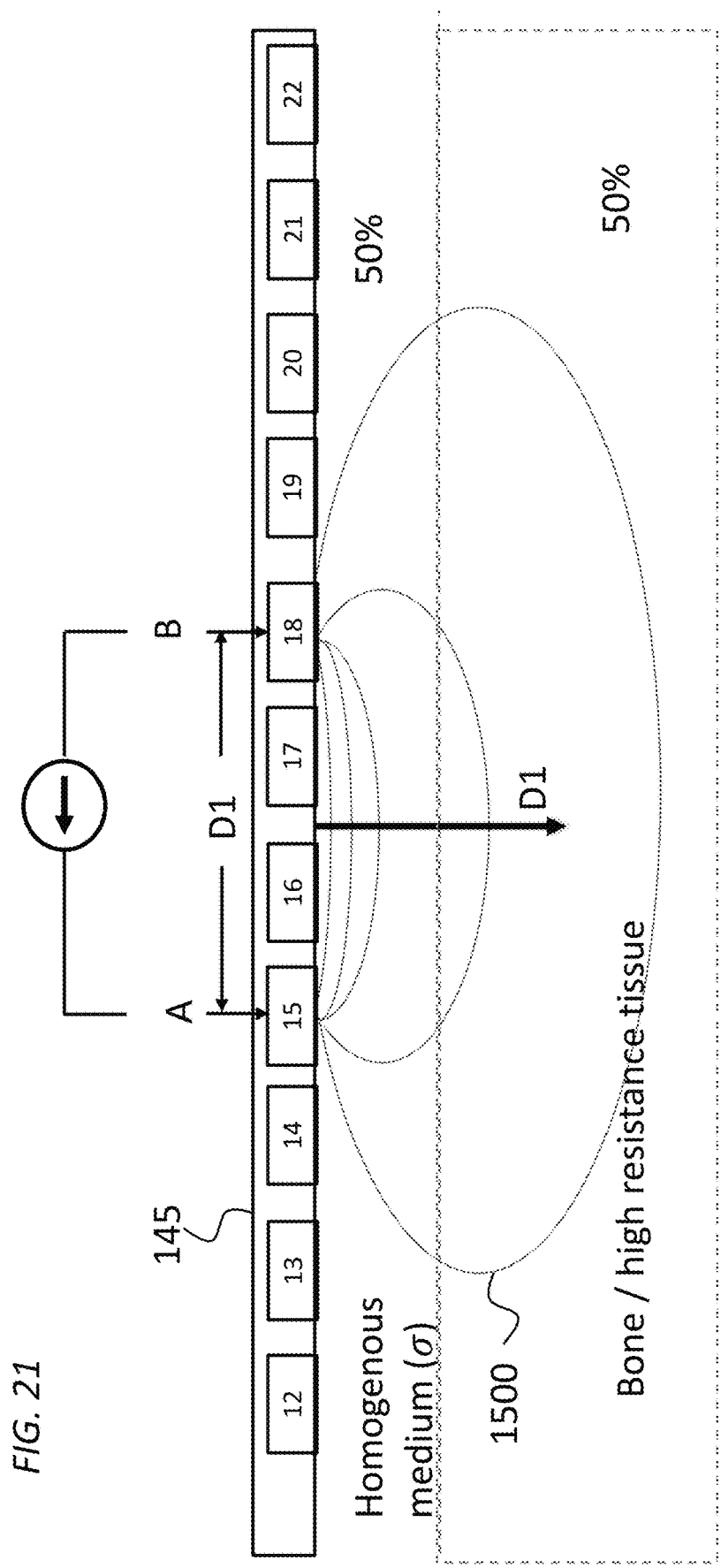

FIG. 21 schematically depicts a scenario where the electrode array 145 is located closer to the modiolus wall/the tissue of high resistivity relative to that which is the case in FIG. 20. Here, the wall is located at half the distance D1 (the distance that equals the distance between the source and sink electrodes). Basically, the tissue of high resistivity is located within an area in which a recognizable percentage of the charge flows. Here, about 50% of the charge flows through the tissue of higher resistivity. This changes the resistivity of the current flow between the source and sink electrodes. For purposes of discussion, the resistivity of current flow between the source and sink will be conceptually unitized as 700 for the arrangement of FIG. 21. In this regard, by measuring the resistivity or other electrical features of the electrode array in this arrangement, a determination can be made that the tissue of higher resistivity (e.g., modiolus wall) is closer than that which is the case for the scenario of FIG. 20.

Figure 22:
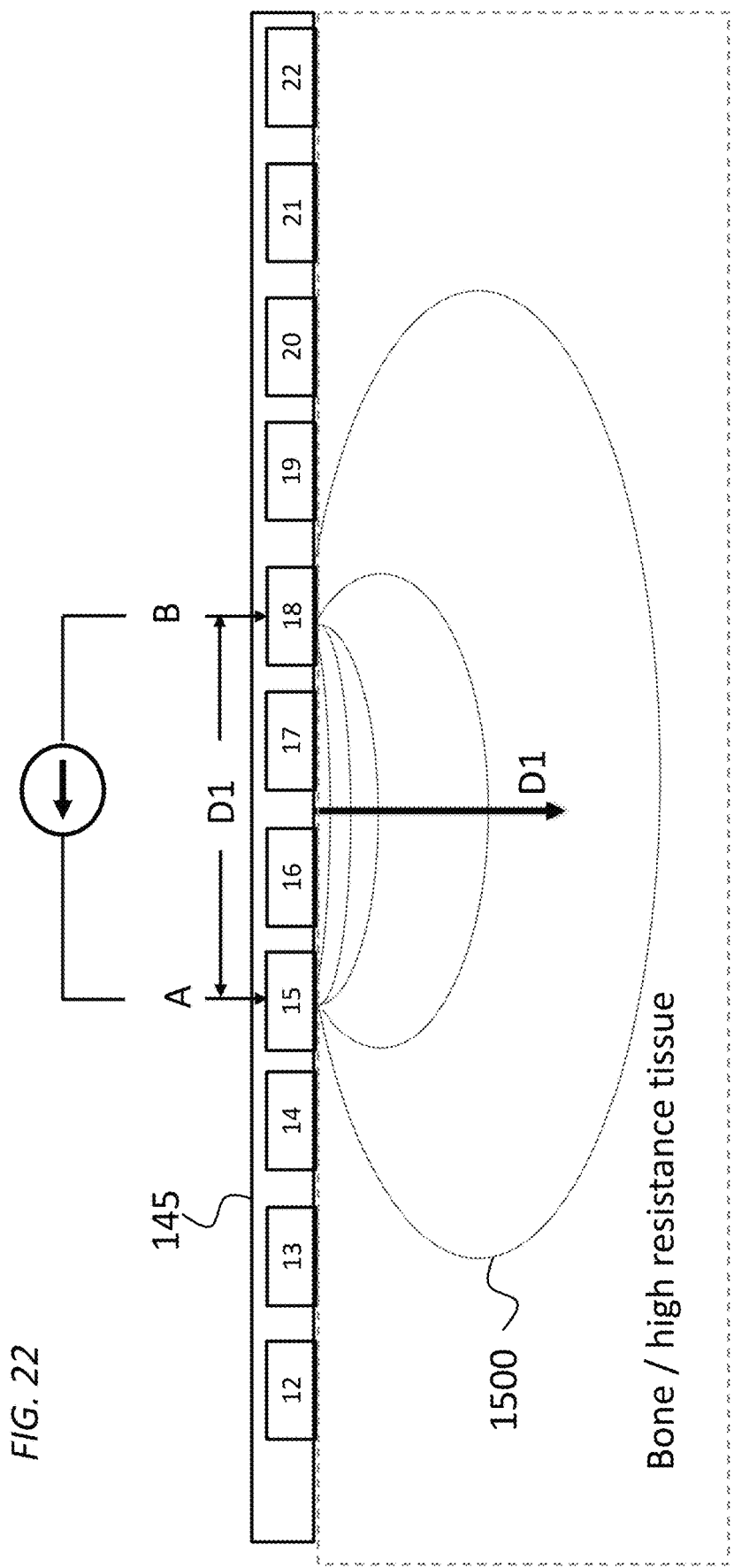

FIG. 22 schematically depicts a scenario where the electrode array 145 is located closer to the modiolus wall/the tissue of high resistivity relative to that which is the case in FIG. 21. Here, the wall is located essentially right against the electrodes. Basically, the tissue of high resistivity is located within an area in which a recognizable percentage of the charge flows. Here, almost all of the charge flows through the tissue of higher resistivity. This changes the resistivity of the current flow between the source and sink electrodes. For purposes of discussion, the resistivity of current flow between the source and sink will be conceptually unitized as 3000 for the arrangement of FIG. 22. In this regard, by measuring the resistivity or other electrical features of the electrode array in this arrangement, a determination can be made that the tissue of higher resistivity (e.g., modiolus wall) is closer than that which is the case for the scenario of FIG. 21.

In an exemplary embodiment, because the spacing of the source and sink electrodes is known, by measuring the resistivity (or impedance, or any pertinent electrical property) utilizing one or more of the electrodes of the electrode array or other components of a system that can enable the teachings detailed herein, a distance from the electrode array to the modiolus wall (or other tissue of interest) can be determined.

Figure 23:
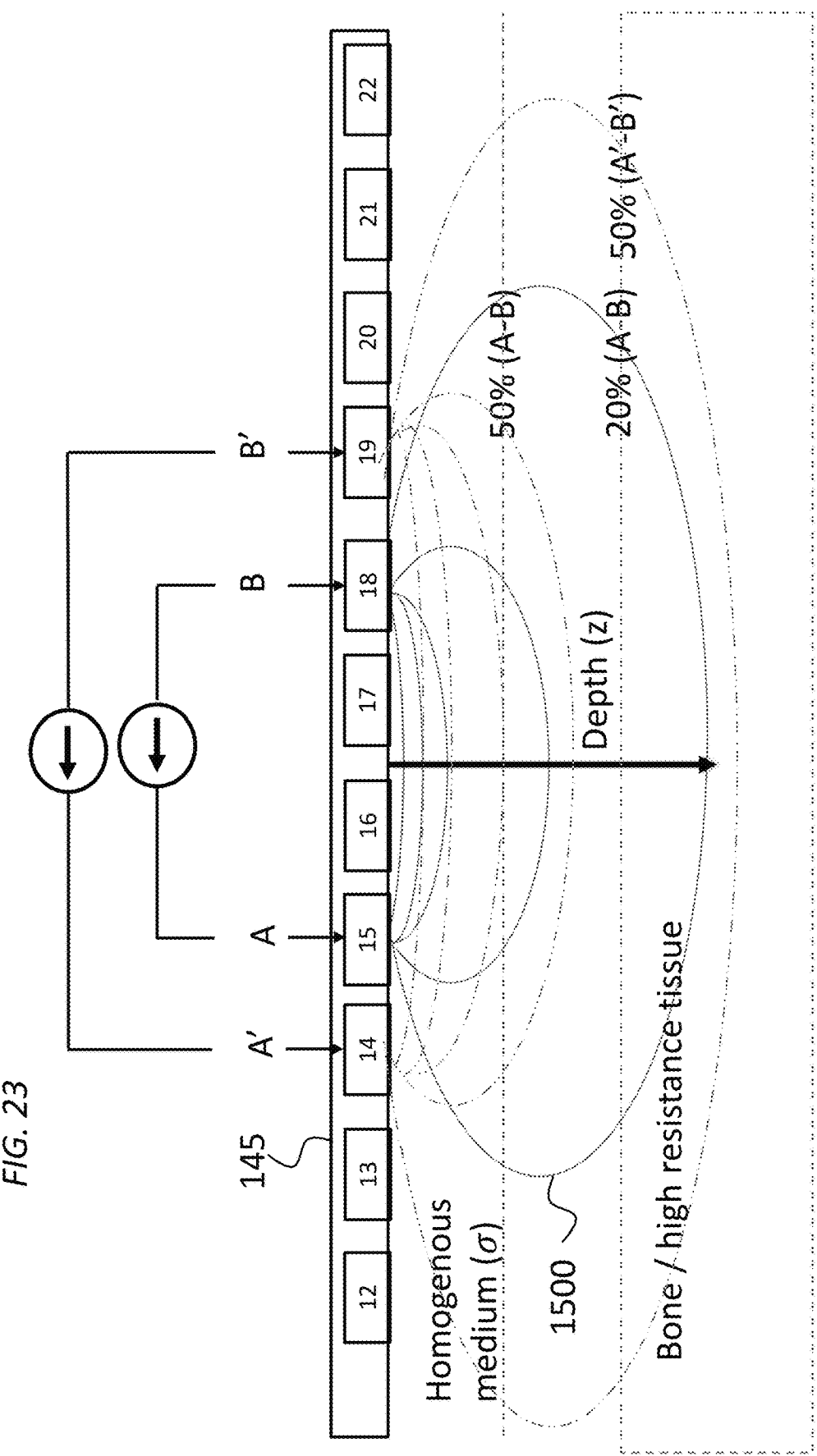

Note that spacing between the source and sink electrodes changes the depth of penetration vis-à-vis the percentage of current that travels through a given layer. As noted above, D1 is a value that is based on the distance between the source and sink electrodes. Increase D1, and the distance of the layers changes. This is depicted in FIG. 23, where the percentage values of the current flow in a given layer are presented, corresponding to spacing A-B (electrodes 15 and 18), and the percentage values the current flow corresponding to spacing A'-B' (electrodes 14 and 19) are also presented. As can be seen, the depth from the electrode array that 50% of the current flows therein becomes larger with the increased electrode spacing. Accordingly, in a scenario where, for example, the relatively high resistivity tissue is located at the level where 50% of the current flow for electrodes A' and B' (corresponding to the location where 70% of the current flows for electrodes A and B) the effective total impedance for A' and B' could be unitized as 350 (as opposed to the unitized resistivity of 150 for electrodes A and B—the arrangement of FIG. 20). Accordingly, by varying the distance of the source and sink electrodes, the different resulting effective resistivities (or other measured electrical phenomenon) will provide information regarding the distance from the electrode array to the tissue of relatively higher resistivity (e.g., bone of the modiolus wall).

Figure 24:
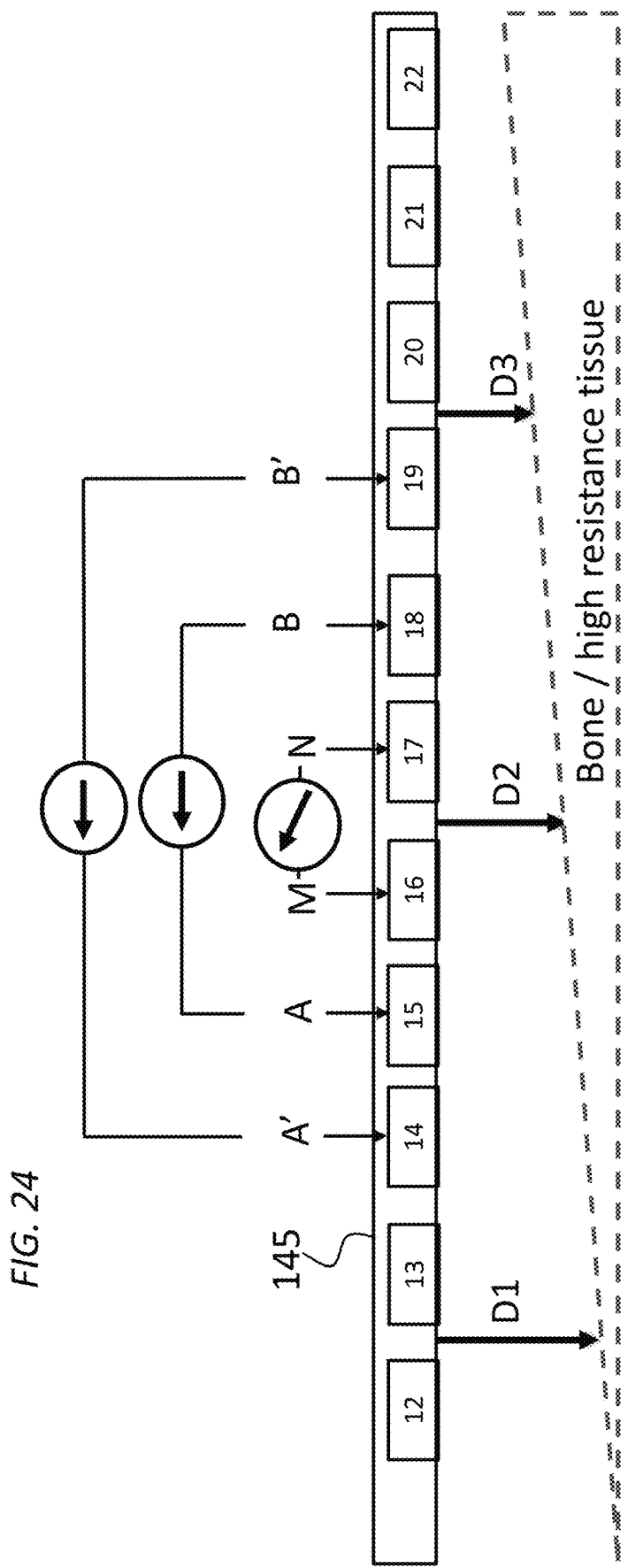
FIG. 24 depicts in a conceptual manner distances of an electrode from a tissue of interest.

FIG. 24 depicts an exemplary scenario of an electrode array 145 spaced away from the modiolus wall (bone) but at distances that are different with respect to location along the length of the electrode array. More specifically, three exemplary heights are presented, with D1 being larger than D2, and D2 being larger than D3. The distances are indicated at the location equidistant between the source and sink electrodes (the electrodes are labeled for D2—the same would be the case for D1 and D3). In an exemplary embodiment, electrode 15 and electrode 18 are utilized as the source and sink, respectively, and electrode 16 and electrode 17 (M and N) are utilized as the measurement electrodes. The resistivity/impedance at electrodes 16 and 17 is measured for a given charge applied to electrodes 15 and 17. Next (or before), electrode 14 and electrode 19 are utilized as the source and sink, respectively, and electrodes 16 and 17 are utilized as the measurement electrodes. That said, electrodes 15 and 18 can be utilized as the measurement electrodes. The resistivity/impedance at electrodes 16 and 17 (or 15 and 18) is measured for a given charge applied to electrodes 14 and 18. Based on these measurements, the distance D2 can be determined. (Additional measurements can be utilized, by, for example, further spacing the source and sink electrodes, etc.) This process can be duplicated to determine D1 and D3 as well.

It is noted that in some embodiments, electrode B (or A) can be further than those detailed. Indeed, in some exemplary embodiments, electrode B (or A) can be the ball electrode/the extra cochlear electrode).

It is noted that the depth of median current flow can be asymmetrical. This can be determined by separation of electrodes from the stimulating polar electrodes. Electrical sensitivity can be dependent on inhomogeneities between the measurement electrodes, as well as the source electrode and one or both of the measurement electrodes (or the sink electrode and one or both of the measurement electrodes). In some exemplary embodiments, two recording measurements are taken, one with A left of the measurement electrodes and one with A right of the reader electrodes, and the results are combined to compensate for asymmetry.

Figure 25:
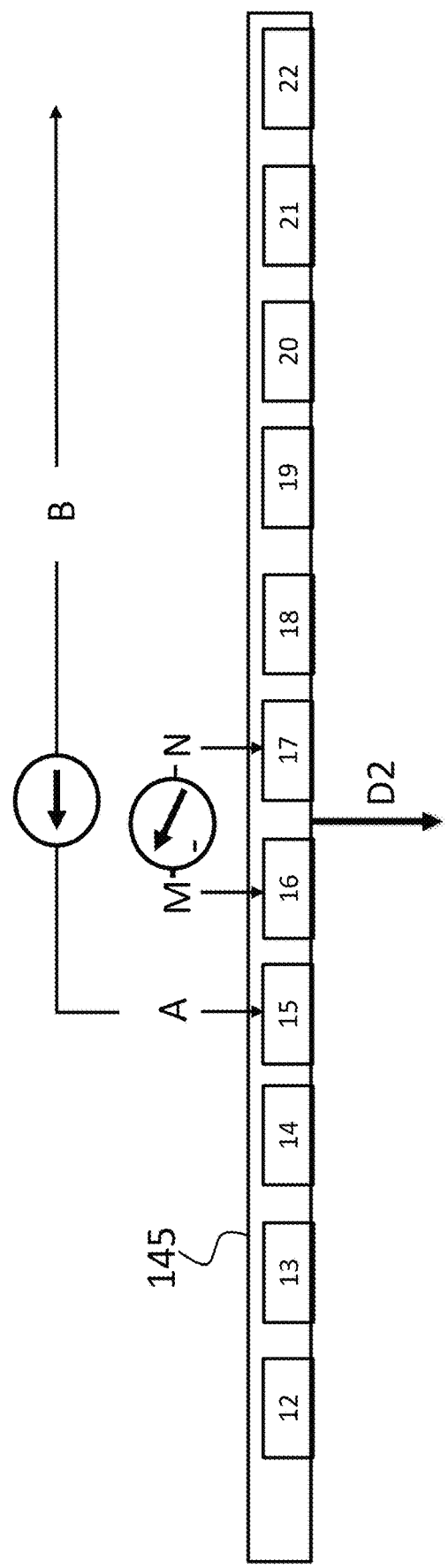
FIGS. 25-33 conceptually depict data obtention according to an exemplary method.

FIG. 25 conceptually illustrates an exemplary scenario where one of the source/sink electrodes (electrode B) is sufficiently far that effects of asymmetry or the like can be neglected. Here, the voltages can be calculated using the equations presented in FIG. 25, and reproduced below:

$$V_{MN} = V_M - V_N$$
$$= \frac{I}{4\pi\sigma}\left[\frac{1}{|AM|} - \frac{1}{|AN|}\right]$$
$$= \frac{I}{\sigma}k$$

$$k = \frac{1}{4\pi}\left[\frac{1}{|AM|} - \frac{1}{|AN|}\right]$$
$$= \frac{1}{4\pi an(n+1)}$$

Assuming dipole spacing
|MN|=a
|AM|=na

In some exemplary embodiments, a rule of thumb is applied where the separation |AM|<20×|AB| for errors to be less than 5%. K is effectively the correction factor for the voltage spread with distance, and is determined by the geometric arrangement of electrodes.

In view of the above, it can be seen that in some exemplary embodiments, because the location of the investigation is known, and because the depth of the investigation is approximately known, one can build depth projection based on current.

Figure 26:
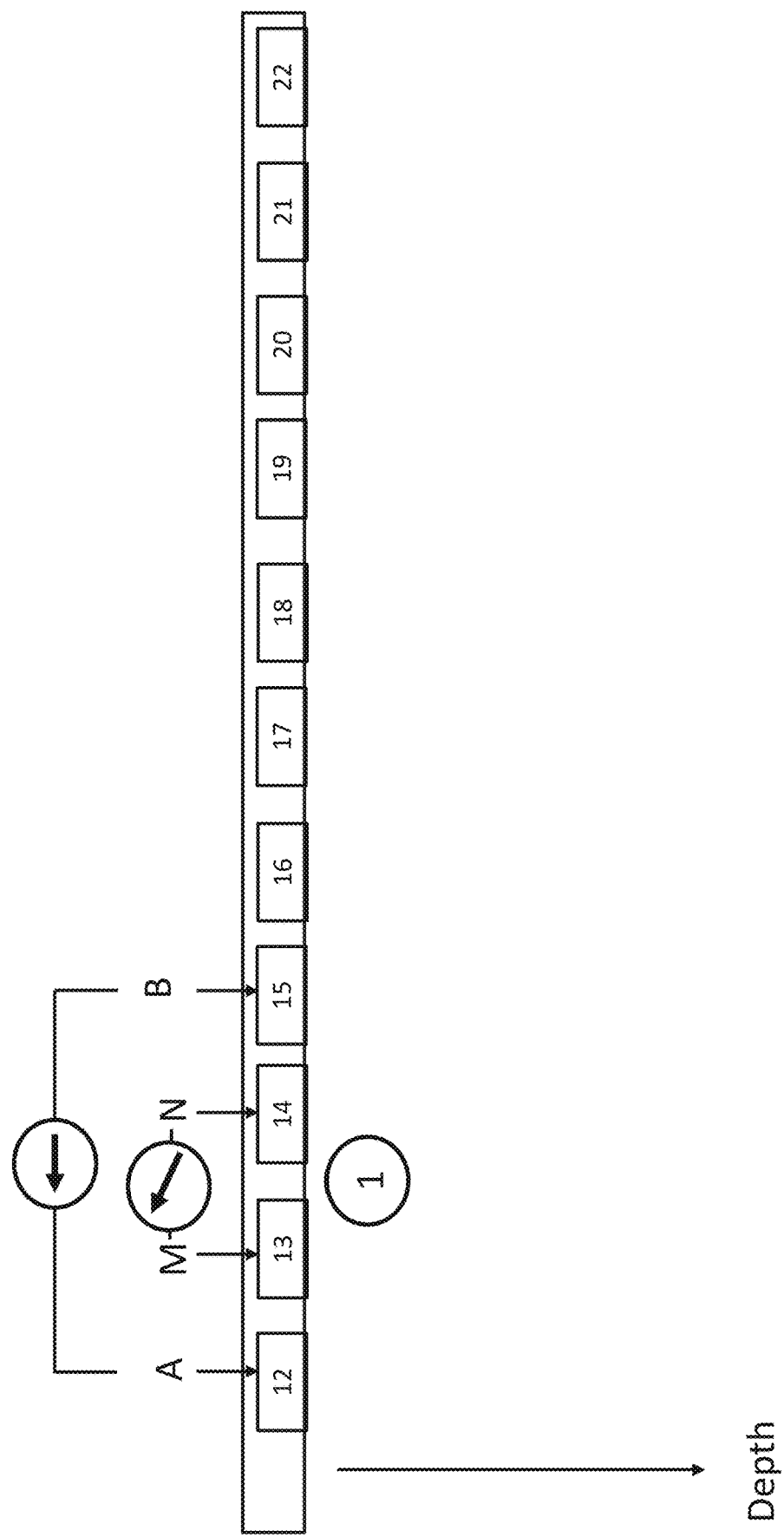
Figure 27:
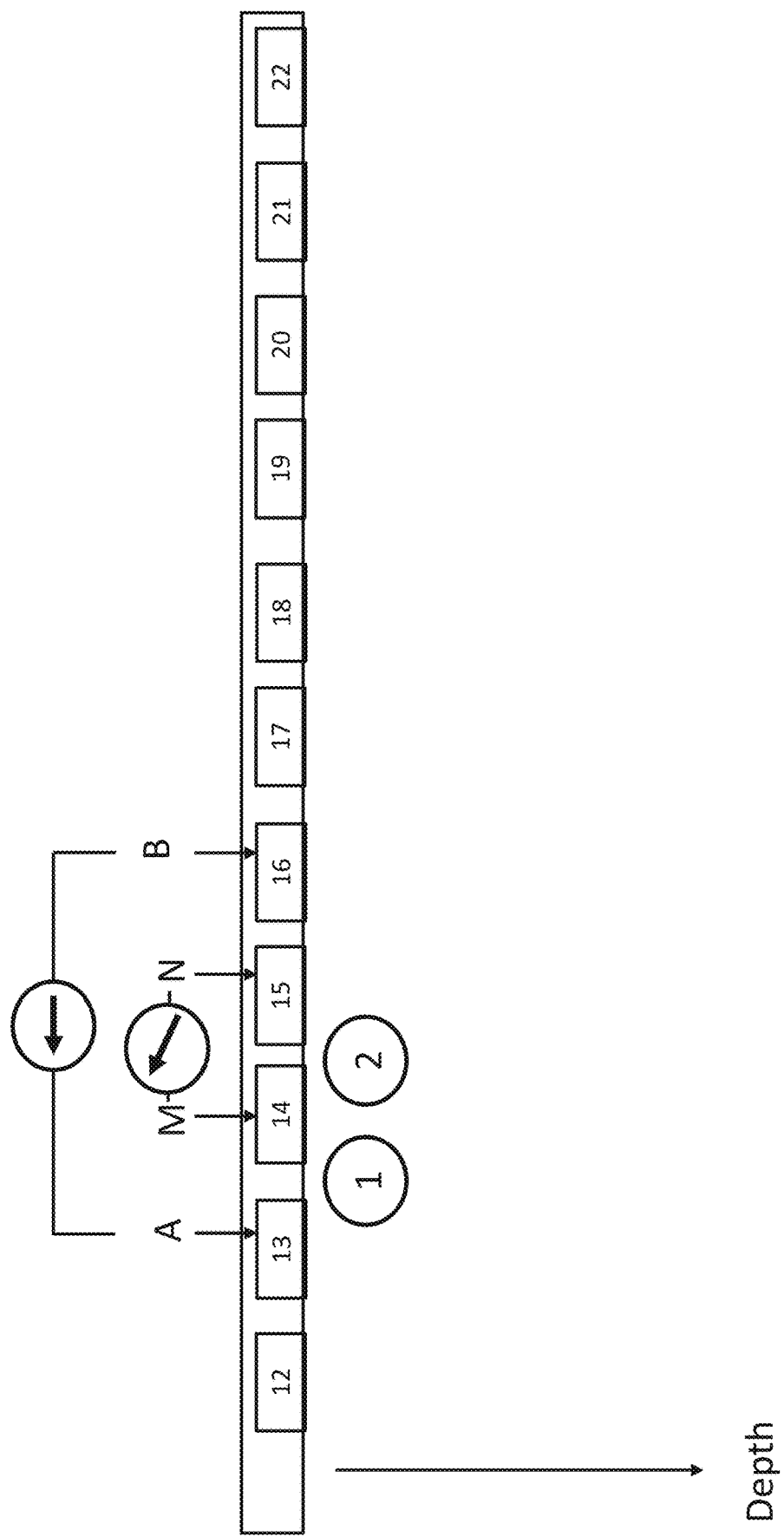
Figure 28:
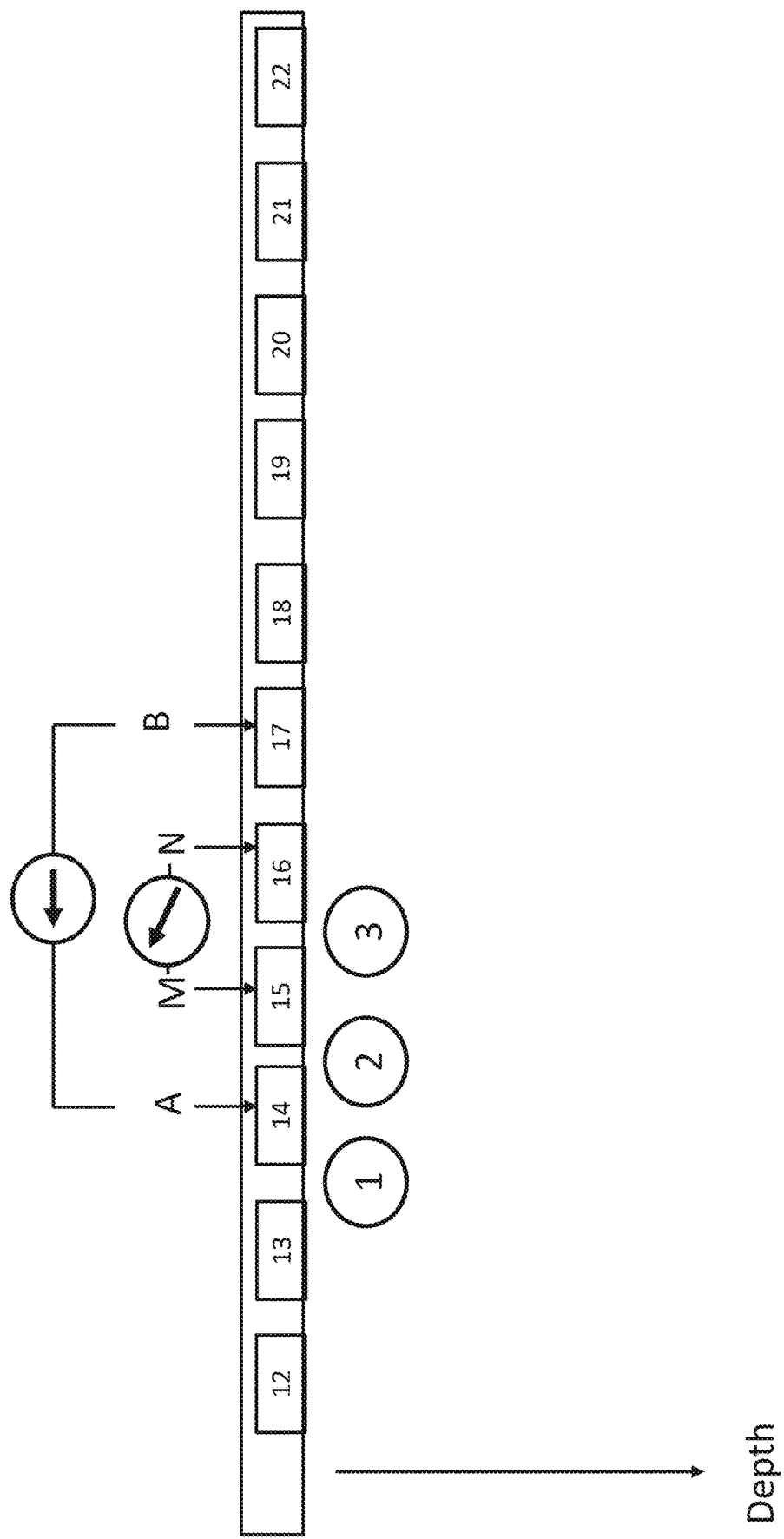

FIGS. 26-32 conceptually illustrate an exemplary embodiment where the electrodes of the electrode array are utilized as source and sink electrodes and as recorder electrodes. FIG. 26 depicts an exemplary embodiment where electrodes 12 and 15 are utilized as the source and sink electrodes, and electrodes 13 and 14 are utilized as the measurement electrodes. This results in data 1 being developed, which data is correlated to a generic depth of current travel (where, as noted above, the further the source and sink, the further the depth of current travel). In an exemplary embodiment, data 1 corresponds to the voltage between electrodes 13 and 14. FIG. 27 depicts an exemplary embodiment where electrodes 13 and 16 are utilized as the source and sink electrodes, and electrodes 14 and 15 are utilized as the measurement electrodes. This results in data 2 being developed, which data is correlated to the generic depth. In an exemplary embodiment, data 2 corresponds to the voltage between electrodes 14 and 15. FIG. 28 depicts an exemplary embodiment where electrodes 14 and 17 are utilized as the source and sink electrodes, and electrodes 15 and 16 are utilized as the measurement electrodes. This results in data 3 being developed, which data is correlated to the generic depth. In an exemplary embodiment, data 3 corresponds to the voltage between electrodes 15 and 16.

Figure 29:
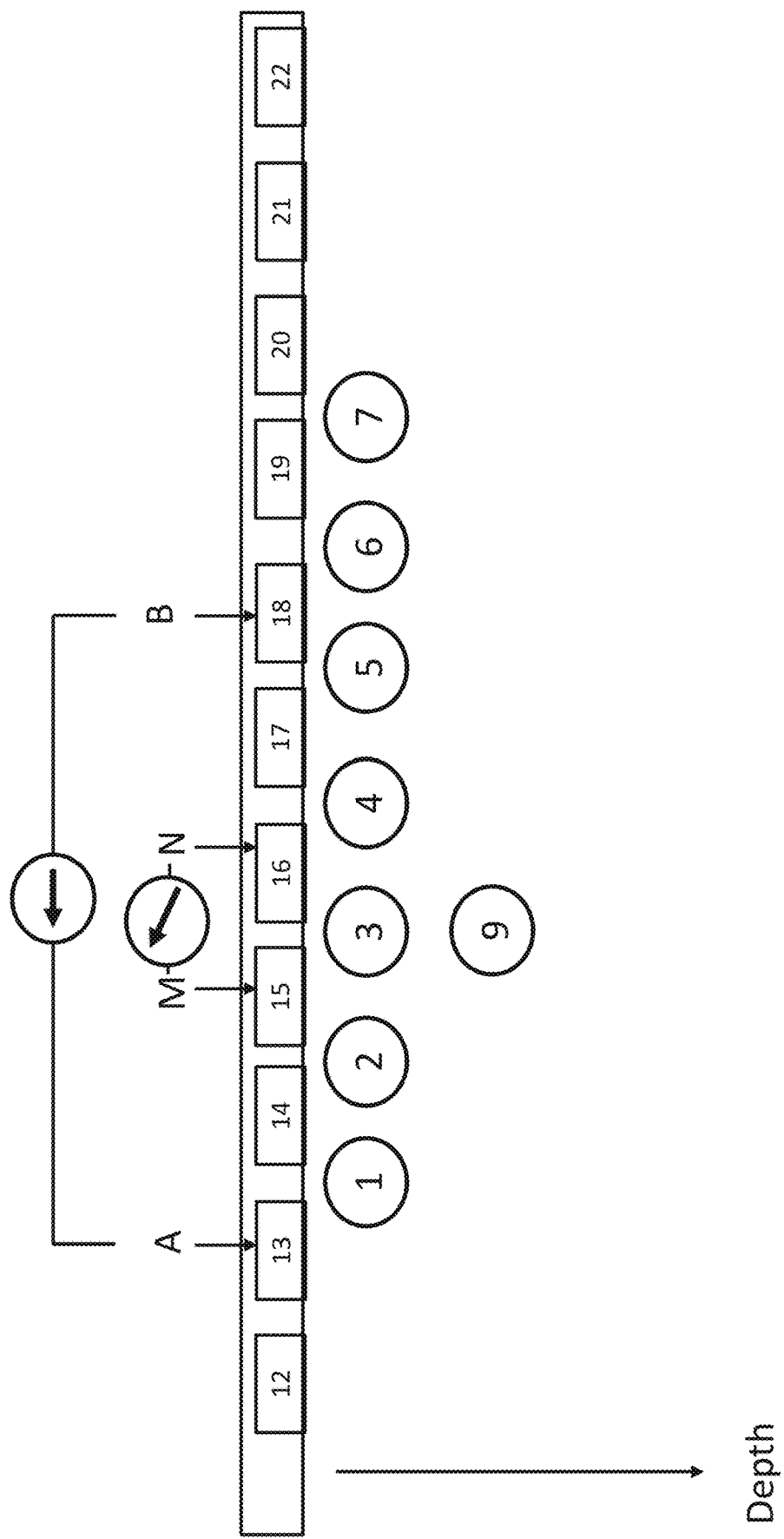

The source and sink and recorder electrodes are moved for some or all of the electrodes of the electrode array. FIG. 29 conceptually represents data 1 to 7 developed utilizing electrode pairs that are spaced apart from one another by two electrodes (the measurement electrodes), where alignment for the given data corresponds to the halfway point between the source and sink electrodes utilized to develop the data (e.g., for data 7, electrodes 18 and 21 were the source and sink electrodes, and electrodes 19 and 20 were the measurement electrodes). Additional data points or fewer data points can be developed depending on the embodiment.

Figure 30:
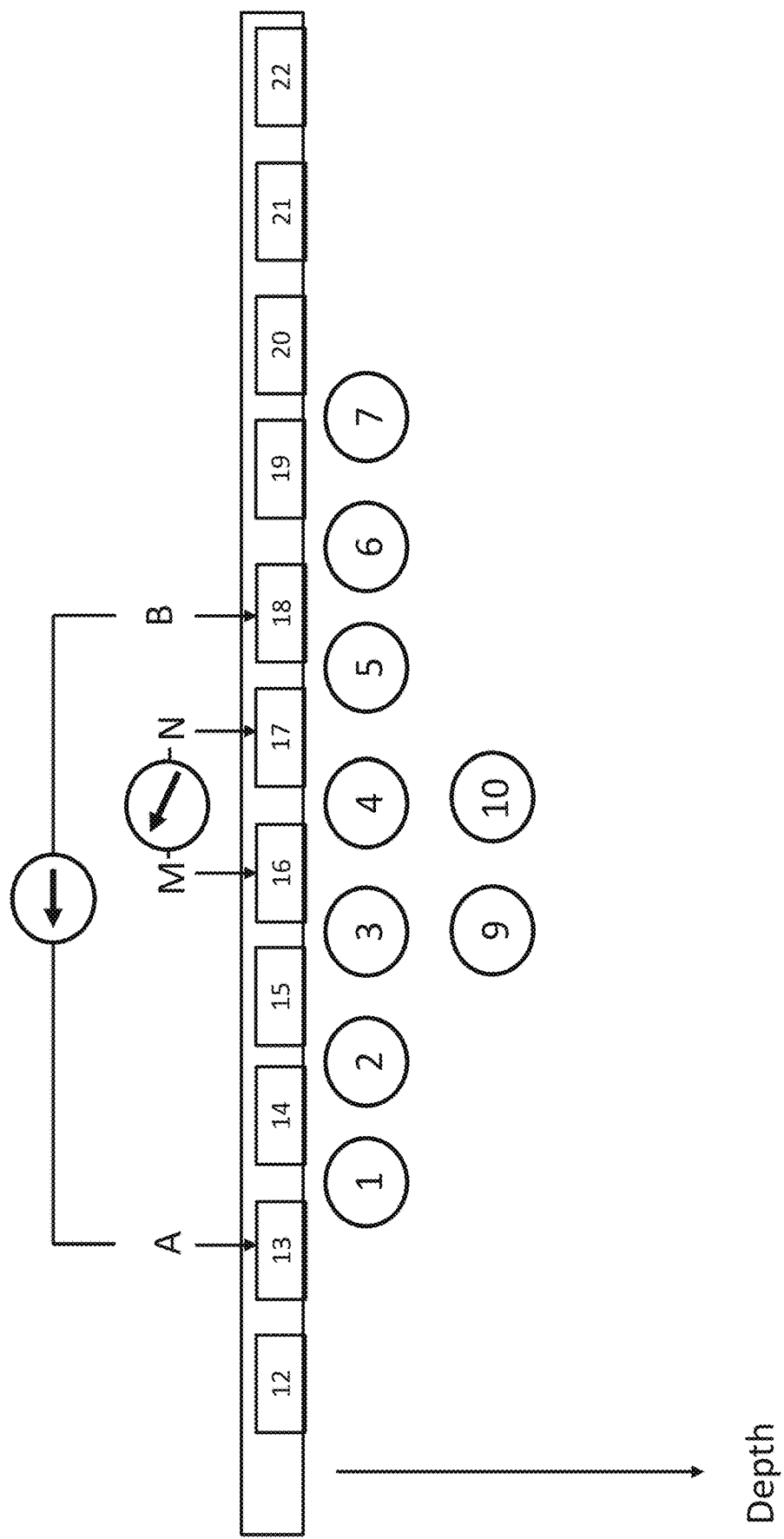
Figure 31:
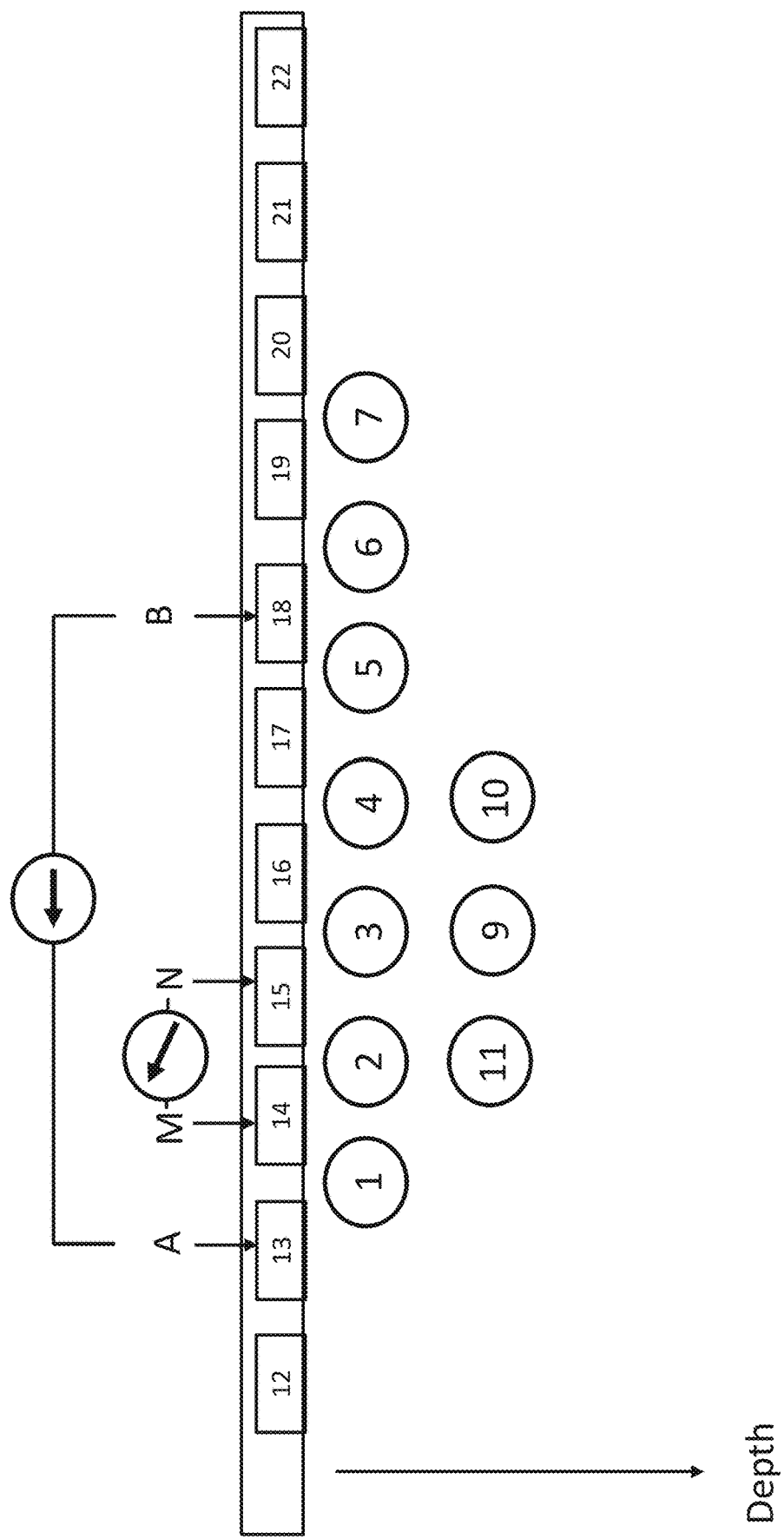

FIG. 29 also depicts data 9, which data is developed using electrodes 13 and 18 as the source and sink electrodes, and electrodes 15 and 16 are utilized as the measurement electrodes. This results in data 9 being developed, which data is correlated to the generic depth. In an exemplary embodiment, data 9 corresponds to the voltage between electrodes 15 and 16. FIG. 30 depicts data 10, which data is developed using electrodes 13 and 18 as the source and sink electrodes, and electrodes 16 and 17 are utilized as the measurement electrodes. This results in data 10 being developed, which data is correlated to the generic depth. In an exemplary embodiment, data 10 corresponds to the voltage between electrodes 16 and 17. FIG. 31 depicts data 11, which is developed using electrodes 14 and 15 as the measurement electrodes and electrodes 13 and 18 as the source and sink.

Figure 32:
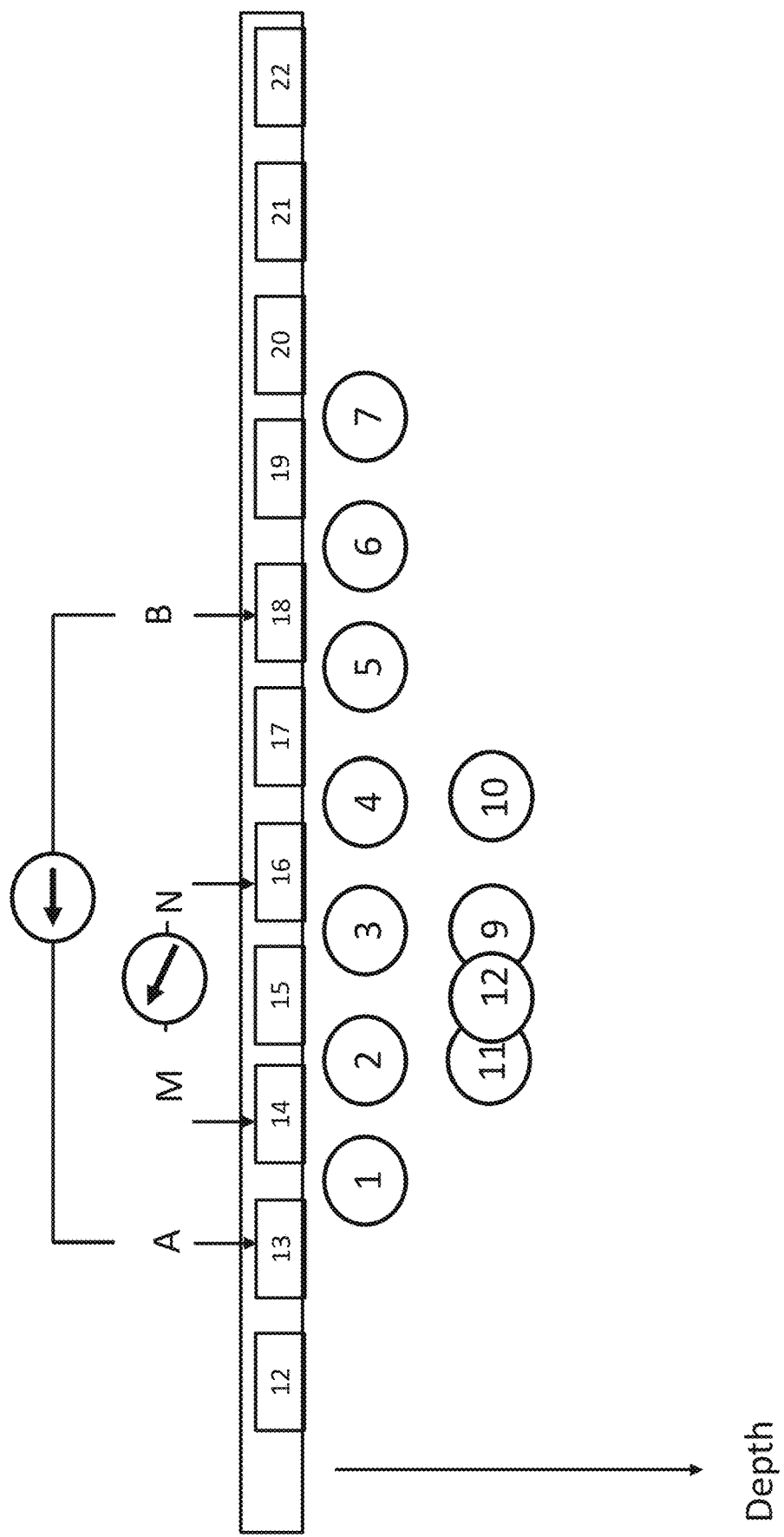

FIG. 32 depicts data 12, which is developed using electrodes 13 and 18 as the source and sink electrodes, and electrodes 14 and 16 as the measurement electrodes.

Variations of the above exemplary embodiments can be executed to obtain various data points having utilitarian value.

Figure 33:
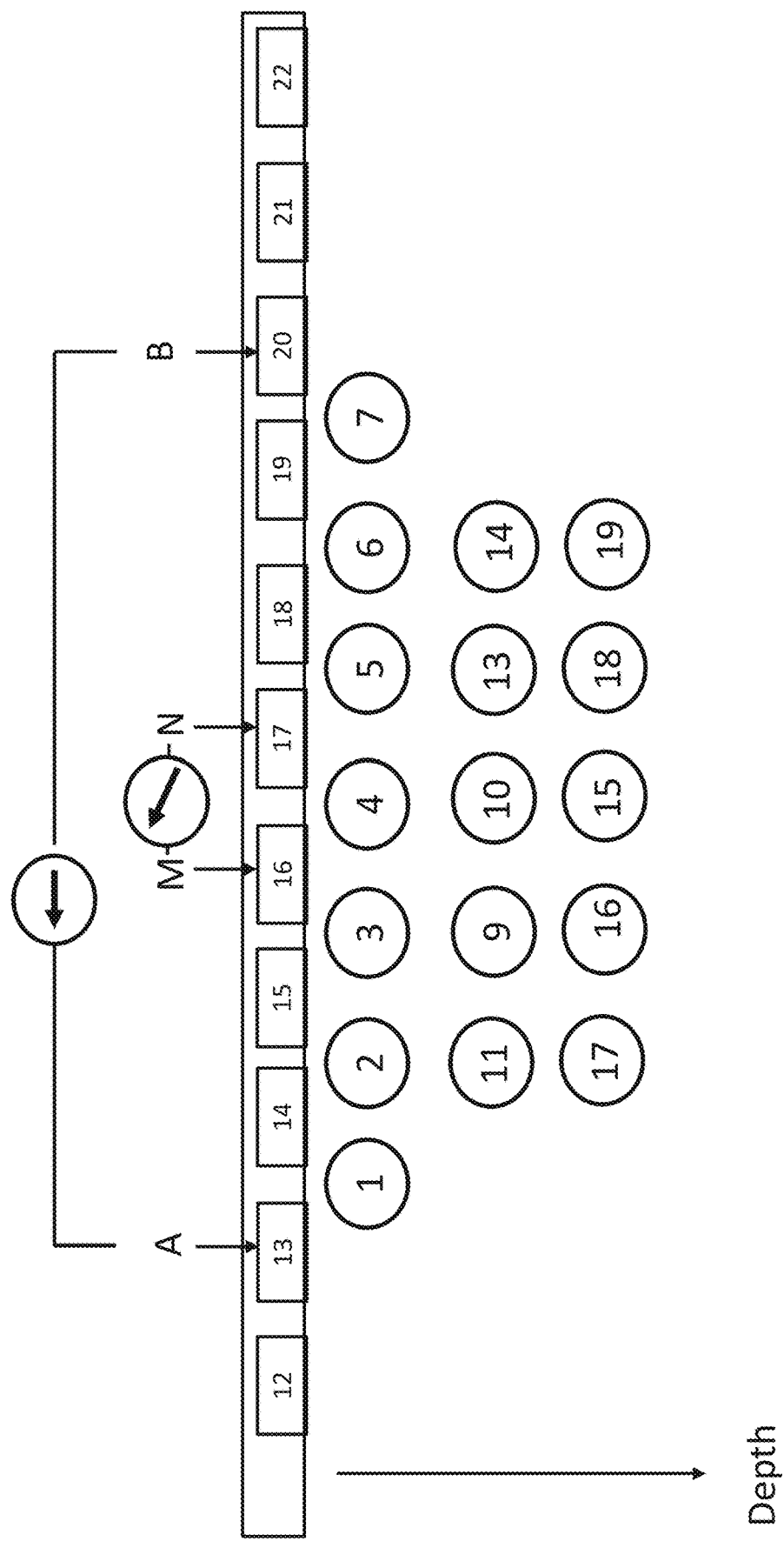

FIG. 33 depicts data 13 and 14, which data was developed utilizing, respectively, electrodes 17 and 18 as measurement electrodes, and electrodes 15 and 20 as the source and sink electrodes, and electrodes 18 and 19 as the measurement electrodes, and electrodes 16 and 21 as the source and sink electrodes. FIG. 33 also depicts data 15, which data was developed using electrodes 13 and 20 as the source and sink, and electrodes 16 and 17 as the measurement electrodes. Using electrodes 13 and 20 as the source and sink electrodes, data 17 is developed using electrodes 14 and 15 as the measurement electrodes, data 16 is developed using electrodes 15 and 16 as the measurement electrodes, data 18 is developed using electrodes 17 and 18 as the measurement electrodes, data 19 is developed using electrodes 18 and 19 as the measurement electrodes, etc.

Consistent with the teachings detailed above, as the distance between the source and sink expands, the further the electrical field will radiate from the electrode array (e.g., the further 50% of the current generated by the electrical field will be located from the electrode array). The further that the electrical field radiates from the electrical array, the more the electrical field will radiate through the relatively highly resistive bone of the cochlea (relative to the resistivity of the perilymph), which will result in different readings for the respective data. For example, where the voltage is measured between electrodes 16 and 17, for a given current, the voltage of data 4 should be lower than the voltage of data 10 and the voltage of data 10 should be lower than the voltage of data 15, etc. Without being bound by theory, at some point (where the distance between the source and sink electrodes has increased by a certain amount), the voltage between electrodes 16 and 17 should noticeably spike, indicating that a substantial amount of the current extends into the bone of the cochlea (modiolus wall, for example), Relative to that which was the case when the source and sink electrodes were closer to each other.

From the above, it is to be understood that in an exemplary embodiment, the various electrodes of the electrode array can be sequentially activated and other electrodes of the electrode array can be utilized as measurement electrodes to obtain electrical characteristics associated therewith resulting from the electrical field that results from the activation electrodes. Because the distance between the source and sink electrodes is known (and because the distance between the measurement electrodes is known), the data from the measurement electrodes can be correlated to determine the distance of the electrode array to the modiolus wall. In an exemplary embodiment, this is done utilizing vertical electrical sounding techniques. That is, a data set can be developed by activating various permutations of the electrodes as source and sinks, and utilizing various permutations of the electrodes as measurement electrodes, and applying vertical electrical sounding techniques, because the distance between the electrodes is known, the distance from the electrode array to bone of the cochlea (modiolus wall, for example), or other structure that has a different resistivity than the perilymph in the cochlea, can be determined.

Figure 34:
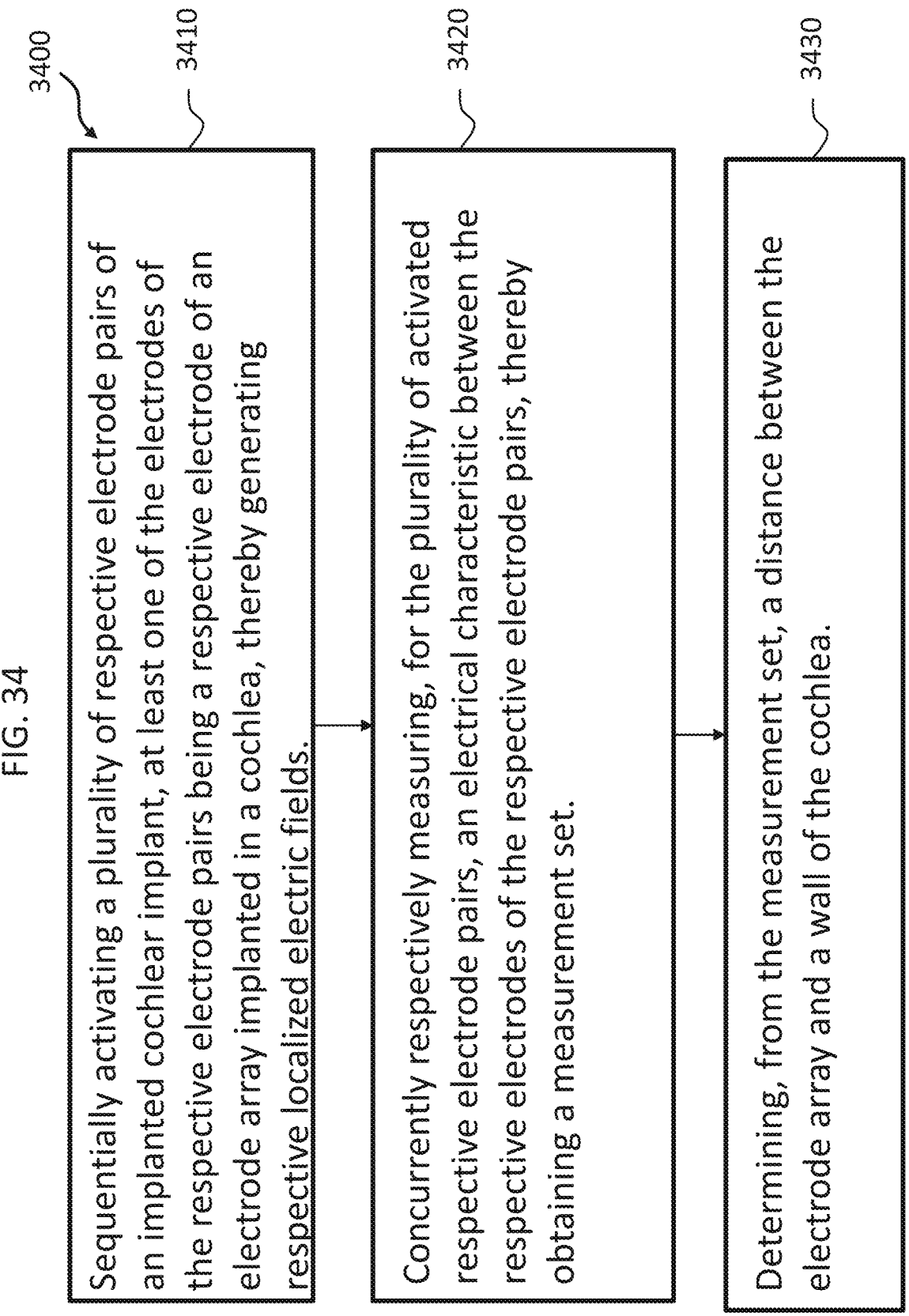
FIGS. 34-44 present flowcharts for exemplary methods.

FIG. 34 depicts an exemplary flowchart for an exemplary method, method 3400, which includes method action 3410, which includes sequentially activating a plurality of respective electrode pairs of an implanted cochlear implant, at least one of the electrodes of the respective electrode pairs being a respective electrode of an electrode array implanted in a cochlea, thereby generating respective localized electric fields. In an exemplary embodiment, this corresponds to utilizing electrodes 12 and 15 as a source and a sink, and then using electrodes 13 and 16 as a source and a sink, and so on.

Method 3400 also includes method action 3420, which includes concurrently respectively measuring, for the plurality of activated respective electrode pairs, an electrical characteristic between the respective electrodes of the respective electrode pairs resulting from the respective localized electric fields, thereby obtaining a measurement set. In an exemplary embodiment, this corresponds to utilizing electrodes 13 and 14 as the measurement electrodes when the electrode pair corresponds to electrodes 12 and 15, and utilizing electrodes 14 and 15 as the measurement electrodes when the electrode pair corresponds to electrodes 13 and 16. From the measurements of the measurement electrodes, a correlated data set is developed.

Method 3400 also includes method action 3430, which includes determining, from the measurement set, a distance between the electrode array and a wall of the cochlea. Consistent with the teachings detailed above, the measurement set can comprise, in some embodiments, respective voltages measured between the respective electrodes of the respective electrode pairs. That said, in other embodiments, other electrical characteristics can be used to establish the measurement set. Combinations of electrical characteristics can be utilized to establish the measurement set. Any electrical characteristic that can enable the teachings detailed herein and/or variations thereof can be utilized in at least some exemplary embodiments.

As will be understood from the above, in some exemplary embodiments of method action 3420, the electrical characteristic includes measuring an electrical characteristic using first and second electrodes of the electrode array, which electrodes are different from the electrodes of the electrode pair. In at least some embodiments, the electrode pairs used to create the measurement set comprises a unique pair of electrodes. In some embodiments, a respective first electrode of each electrode pair is selected from a first set of consecutive electrodes, a respective second electrode of each electrode pair is selected from a second set of consecutive electrodes, and respective third and fourth electrodes are disposed between the respective first and second electrodes, the third and fourth electrodes being utilized to measure the electrical characteristic. In some exemplary embodiments, the respective first and second electrodes are disposed symmetrically about the respective third and fourth electrodes. In some exemplary embodiments, both of the electrodes of the respective electrode pairs are respective electrodes of the electrode array implanted in the cochlea. This as opposed to some embodiments where, for example, one of the electrodes of the pairs is an extra-cochlear electrode (e.g., the so called hardball electrode, etc.).

Figure 35:
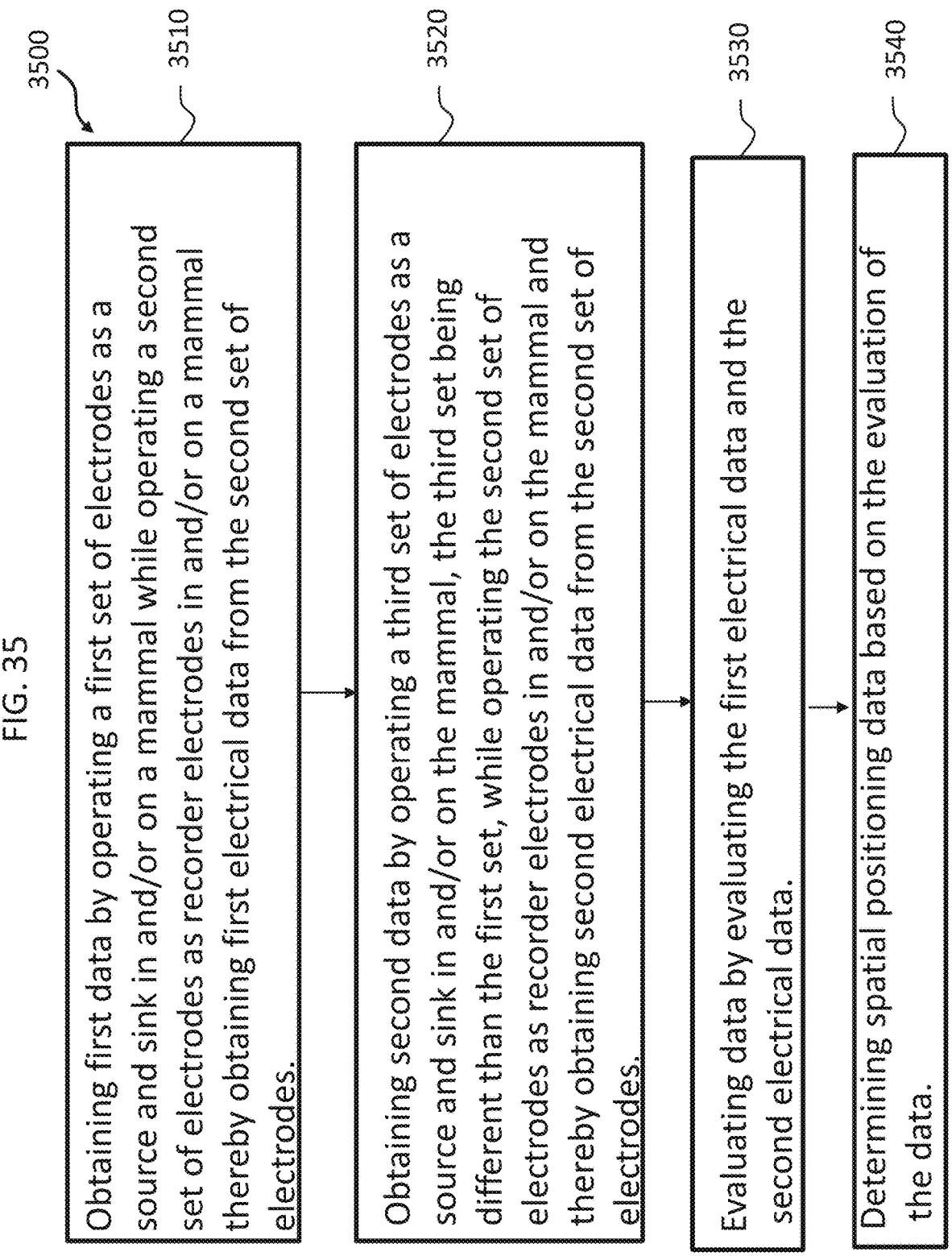

FIG. 35 presents a flowchart for an exemplary method, method 3500, including method action 3510, which includes obtaining first data by operating a first set of electrodes as a source and sink in and/or on a mammal (e.g., electrodes of a cochlear electrode array located in a cochlea) while operating a second set of electrodes as recorder electrodes in and/or on a mammal (again, for example, the cochlear electrode array located in a cochlea) thereby obtaining first electrical data from the second set of electrodes. In an exemplary embodiment, the first electrical data corresponds to voltage measurements at the electrodes of the second set of electrodes. Again, consistent with the teachings detailed herein, any electrical characteristic that can enable the teachings detailed herein can be utilized in some embodiments.

Method 3500 further includes method action 3520, which includes obtaining second data by operating a third set of electrodes as a source and sink in and/or on the mammal, the third set being different than the first set, while operating the second set of electrodes as recorder electrodes in and/or on the mammal and thereby obtaining second electrical data from the second set of electrodes. Method 3500 also includes method action 3530, which includes evaluating data by evaluating the first electrical data and the second electrical data, and method action 3540, which includes determining spatial positioning data based on the evaluation of the data, wherein the spatial positioning data is a distance of one or more of the electrodes of the first set or second set from a structure within the mammal.

In an exemplary embodiment, the first electrical data is a first impedance based data (voltage, current, impedance— any data that is based on impedance) between the electrodes of the second set. The second electrical data is a second impedance based data between the electrodes of the second set. Further, the action of evaluating the first electrical data and the second electrical data includes comparing the first electrical data to the second electrical data, and the action of determining the spatial positioning data includes determining a distance of the second set of electrodes from a gradient. In some exemplary embodiments, the gradient is a resistivity gradient. For example, a gradient established between the perilymph and bone of the cochlea.

It is noted that the gradient can also be established by the membrane that is located between bone of the cochlea and the perilymph, if such is present.

In some embodiments, the electrodes of the first set are located closer to one another than the electrodes of the third set and are between electrodes of the third set.

Figure 36:
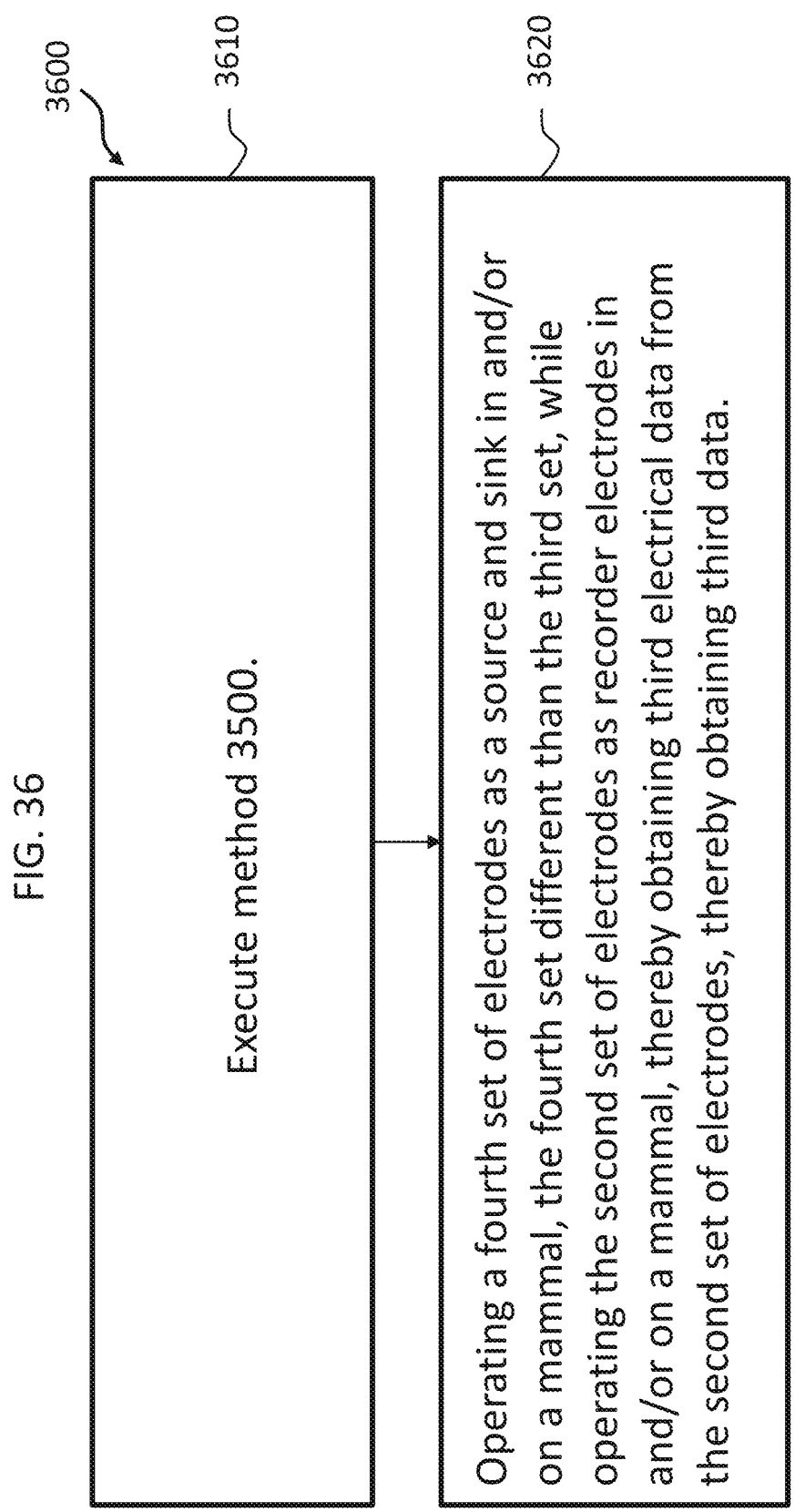

In an exemplary embodiment, there is a method 3600 as represented by the flowchart on FIG. 36, which method includes method action 3610, which includes executing method 3500. Method 3610 also includes method action 3620, which includes obtaining third data by operating a fourth set of electrodes as a source and sink in and/or on the mammal, the fourth set different than the third set, while operating the second set of electrodes as recorder electrodes in and/or on the mammal, thereby obtaining third electrical data from the second set of electrodes. In an exemplary embodiment, the action of evaluating data includes evaluating the third electrical data while also evaluating the second electrical data and the first electrical data, and the electrodes of the first set are located closer to one another than the electrodes of the third set and are between electrodes of the third set, and the electrodes of the third set are located closer to one another and between electrodes of the fourth set.

In some embodiments, the recorder electrodes are part of a cochlear electrode array that is located in a cochlea, as noted above. Also, the determined spatial positioning data is distance data of the recorder electrodes from a modiolus wall of the cochlea. In some embodiments, the determined spatial positioning data is an orientation of the recorder electrodes relative to structure of the cochlea. For example, the orientation can be whether the electrodes face directly at the modiolus wall, or whether the electrodes face away from the modiolus wall. In an exemplary embodiment, the orientation is an approximate angle from a centerline of the electrode to a centerline of the modiolus wall. In an exemplary embodiment, the orientation is an approximate angle that represents the difference from the ideal orientation of the electrodes relative to the modiolus wall and the actual angle.

Figure 37:
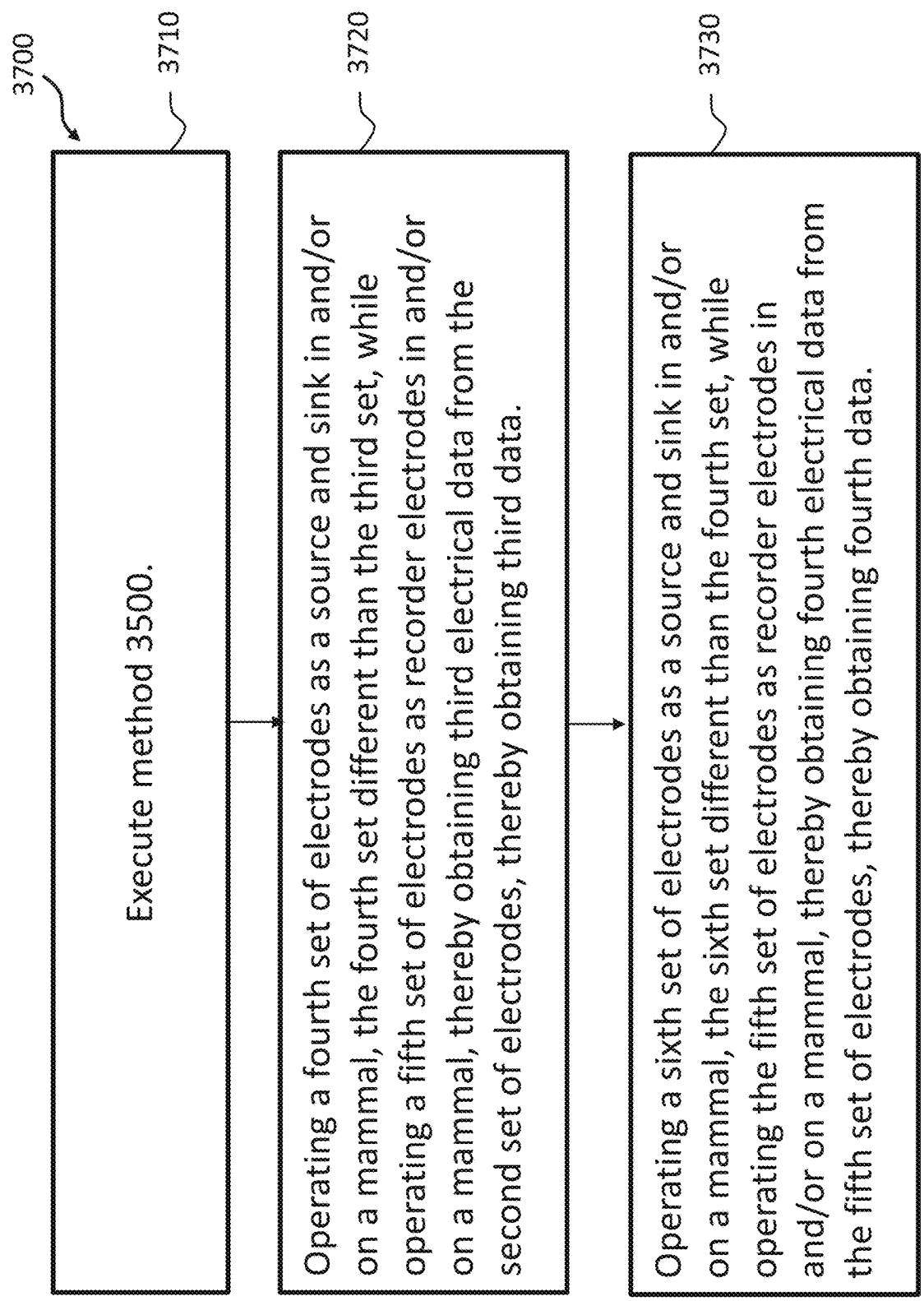

FIG. 37 represents an exemplary flowchart for an exemplary method, method 3700, which includes method action 3710, which includes executing method 3500. Method 3700 further includes method action 3720, which includes, obtaining third data by operating a fourth set of electrodes as a source and sink in and/or on the mammal, the fourth set different than the third set, while operating a fifth set of electrodes as recorder electrodes in and/or on the mammal, thereby obtaining third electrical data from the second set of electrodes. Method 3700 further includes method action 3730, which includes obtaining fourth data by operating a sixth set of electrodes as a source and sink in and/or on a mammal, the sixth set different than the fourth set, while operating the fifth set of electrodes as recorder electrodes in and/or on the mammal, thereby obtaining fourth electrical data from the seventh set of electrodes. In this exemplary method, in an exemplary embodiment, the action of evaluating data includes also evaluating the third electrical data and the fourth electrical data, the electrodes are part of a cochlear electrode array that is located in a cochlea, and the action of determining spatial positioning data based on the evaluation of the data includes determining a distance of the electrodes of the second set from a modiolus wall of the cochlea based on the evaluation of the second and first electrical data and determining a distance of the electrodes of the fifth set from a modiolus wall of the cochlea based on the evaluation of the third electrical data and the fourth electrical data.

Figure 38:
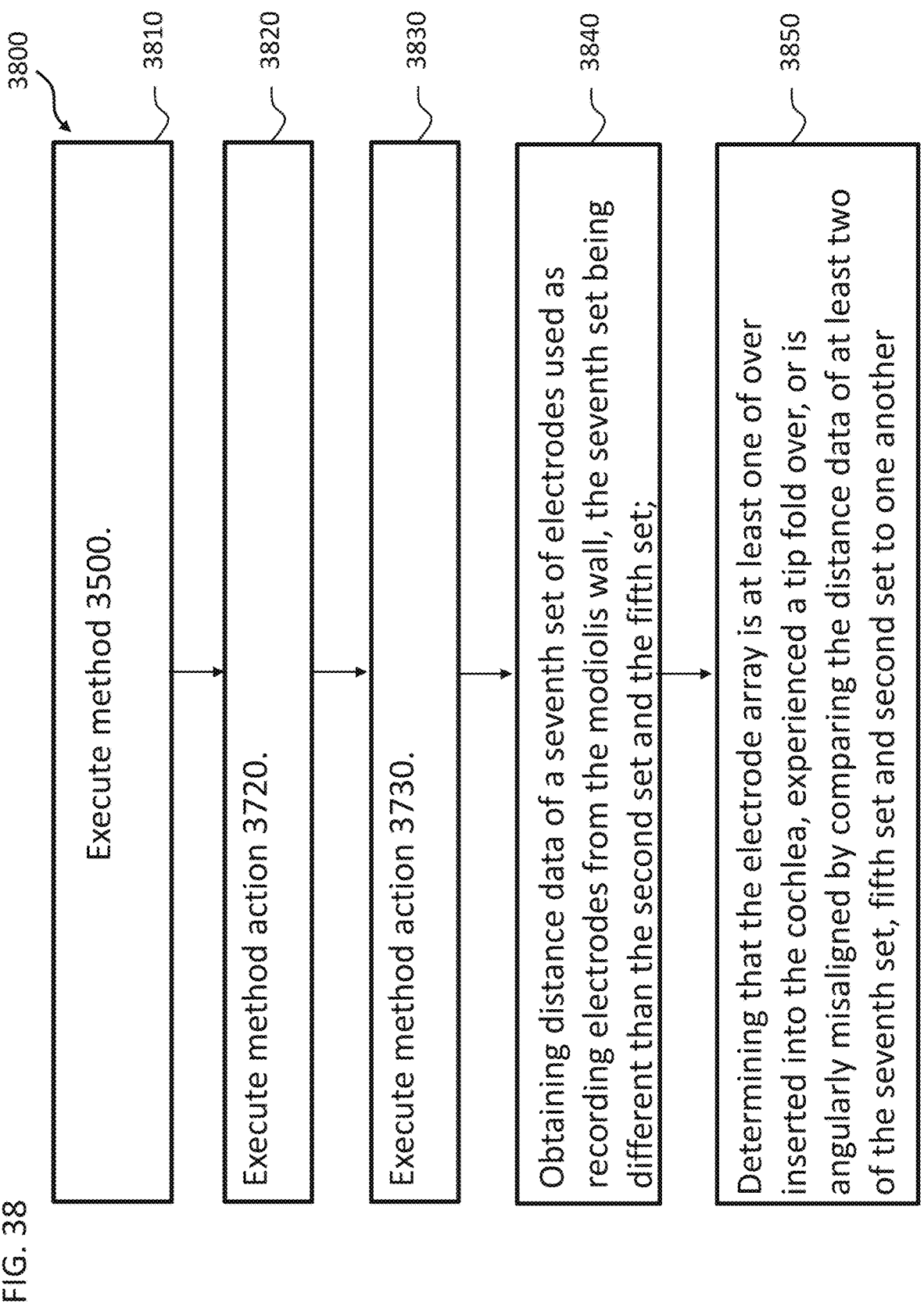

FIG. 38 depicts a flowchart for an exemplary method, method 3800, which includes method action 3810, which includes executing method 3500. Method 3800 also includes method actions 3820 and 3830, which respectively include executing method actions 3720 and 3730. Method 3800 also includes method action 3840, which includes obtaining distance data of a seventh set of electrodes used as recording electrodes from the modiolus wall, the seventh set being different than the second set and the fifth set. Subsequent to this, method 3800 includes method action 3850, which includes determining that the electrode array is at least one of over inserted into the cochlea, has experienced a tip fold over, or is angularly misaligned by comparing the distance data of at least two of the seventh set, fifth set and second set to one another. Some additional details of such features are described below.

Table I below depicts an exemplary regime utilizing a 22 electrode array according to the teachings detailed herein, where each row can correspond to any of the first set of electrodes and second set of electrodes of method action 3510, and where, in an exemplary embodiment, method action 3510 is executed C number of times, and in an exemplary embodiment, each time for a different first set, where C can be 19 times for 22 electrode array, or 27 times for a 30 electrode array, etc. In an exemplary embodiment, C is any integer between 1 and 3 minus the number of electrodes of the array, or any number between 1 and 2 minus the number of electrodes of the array (where, for example, an extra cochlear electrode is used). Any different row from that previously used can corresponds to the third set of electrodes of method action 3520, and method action 3520 can be executed C minus 1 times (to avoid duplication, but in some other embodiments, can be executed C times, as duplication does not prevent method 3500 from being executed—it is just an additional action) or C minus 1 minus the aforementioned minuses.

TABLE I

| Source or Sink Electrode No. (A) | Sink or Source Electrode No. (B) | Measurement electrode No. (M) | Read Electrode No. (N) |
|---|---|---|---|
| 1 | 4 | 2 | 3 |
| 2 | 5 | 3 | 4 |
| 3 | 6 | 4 | 5 |
| 4 | 7 | 5 | 6 |
| 5 | 8 | 6 | 7 |

TABLE I-continued

| Source or Sink Electrode No. (A) | Sink or Source Electrode No. (B) | Measurement electrode No. (M) | Read Electrode No. (N) |
|---|---|---|---|
| 6 | 9 | 7 | 8 |
| 7 | 10 | 8 | 9 |
| 8 | 11 | 9 | 10 |
| 9 | 12 | 10 | 11 |
| 10 | 13 | 11 | 12 |
| 11 | 14 | 12 | 13 |
| 12 | 15 | 13 | 14 |
| 13 | 16 | 14 | 15 |
| 14 | 17 | 15 | 16 |
| 15 | 18 | 16 | 17 |
| 16 | 19 | 17 | 18 |
| 17 | 20 | 18 | 19 |
| 18 | 21 | 19 | 20 |
| 19 | 22 | 20 | 21 |

Table II below depicts an exemplary regime utilizing a 22 electrode array according to the teachings detailed herein, where each row can correspond to any of the first set of electrodes and second set of electrodes of method action 3510 (and the second sets can be the measurement electrodes as listed, or one of the measurement electrodes with the alternate electrode, or both (actually all three—with respect to the first row, the measurement electrodes can be 2 and 3, 2 and 4 and/or 3 and 4 (three sets in total maximum)), and where, in an exemplary embodiment, method action 3510 is executed D number of times (and potentially more to accommodate for the fact that for a given source and sink, there can be various applications of the measurement electrodes, as just noted), and in an exemplary embodiment, each time for a different first set, where D can be 18 times for 22 electrode array, or 26 times for a 30 electrode array, etc. In an exemplary embodiment, D is any integer between 1 and 4 minus the number of electrodes of the array, or any number between 1 and 3 minus the number of electrodes of the array (where, for example, an extra cochlear electrode is used). Any different row from that previously used can corresponds to the third set of electrodes of method action 3520, and method action 3520 can be executed D minus 1 times (to avoid duplication, but in some other embodiments, can be executed D times, as duplication does not prevent method 3500 from being executed—it is just an additional action) or D minus 1 minus the aforementioned minuses.

TABLE II

| Source or Sink Electrode No. (A) | Sink or Source Electrode No. (B) | Measurement electrode No. (M) | Read Electrode No. (N) | Alternate Measurement electrode |
|---|---|---|---|---|
| 1 | 5 | 2 | 3 | 4 |
| 2 | 6 | 3 | 4 | 5 |
| 3 | 7 | 4 | 5 | 6 |
| 4 | 8 | 5 | 6 | 7 |
| 5 | 9 | 6 | 7 | 8 |
| 6 | 10 | 7 | 8 | 9 |
| 7 | 11 | 8 | 9 | 10 |
| 8 | 12 | 9 | 10 | 11 |
| 9 | 13 | 10 | 11 | 12 |
| 10 | 14 | 11 | 12 | 13 |
| 11 | 15 | 12 | 13 | 14 |
| 12 | 16 | 13 | 14 | 15 |
| 13 | 17 | 14 | 15 | 16 |
| 14 | 18 | 15 | 16 | 17 |
| 15 | 19 | 16 | 17 | 18 |
| 16 | 20 | 17 | 18 | 19 |

TABLE II-continued

| Source or Sink Electrode No. (A) | Sink or Source Electrode No. (B) | Measurement electrode No. (M) | Read Electrode No. (N) | Alternate Measurement electrode |
|---|---|---|---|---|
| 17 | 21 | 18 | 19 | 20 |
| 18 | 22 | 19 | 20 | 21 |

Table III below depicts an exemplary regime utilizing a 22 electrode array according to the teachings detailed herein, where each row can corresponds to any of the first set of electrodes and second set of electrodes of method action 3510, and where, in an exemplary embodiment, method action 3510 is executed E number of times (and potentially more to accommodate for the fact that for a given source and sink, there can be various applications of the measurement electrodes, as just noted), and in an exemplary embodiment, each time for a different first set, where E can be 17 times for 22 electrode array, or 25 times for a 30 electrode array, etc. In an exemplary embodiment, E is any integer between 1 and 5 minus the number of electrodes of the array, or any number between 1 and 4 minus the number of electrodes of the array (where, for example, an extra cochlear electrode is used). Any different row from that previously used can correspond to the third set of electrodes of method action 3520, and method action 3520 can be executed E minus 1 times (to avoid duplication, but in some other embodiments, can be executed E times, as duplication does not prevent method 3500 from being executed—it is just an additional action) or E minus 1 minus the aforementioned minuses.

It is noted that the below table indicates that the second set of electrodes of method action 3510 can be any combination of the measurement electrodes. For example, for a source and sink corresponding to electrodes 1 and 6, the measurement electrodes can be 2 and 3, 2 and 4, 2 and 5, 3 and 4, 3 and 5 or 4 and 5.

TABLE III

| Source or Sink Electrode No. (A) | Sink or Source Electrode No. (B) | Measurement electrode No. (M) | Read Electrode No. (N) | First Alternate Measurement electrode | Second Alternate Measurement electrode |
|---|---|---|---|---|---|
| 1 | 6 | 2 | 3 | 4 | 5 |
| 2 | 7 | 3 | 4 | 5 | 6 |
| 3 | 8 | 4 | 5 | 6 | 7 |
| 4 | 9 | 5 | 6 | 7 | 8 |
| 5 | 10 | 6 | 7 | 8 | 9 |
| 6 | 11 | 7 | 8 | 9 | 10 |
| 7 | 12 | 8 | 9 | 10 | 11 |
| 8 | 13 | 9 | 10 | 11 | 12 |
| 9 | 14 | 10 | 11 | 12 | 13 |
| 10 | 15 | 11 | 12 | 13 | 14 |
| 11 | 16 | 12 | 13 | 14 | 15 |
| 12 | 17 | 13 | 14 | 15 | 16 |
| 13 | 18 | 14 | 15 | 16 | 17 |
| 14 | 19 | 15 | 16 | 17 | 18 |
| 15 | 20 | 16 | 17 | 18 | 19 |
| 16 | 21 | 17 | 18 | 19 | 20 |
| 17 | 22 | 18 | 19 | 20 | 21 |

From the above, it can be seen that embodiments include expanding the trend above, one electrode at a time to expand the source and sink distance, while, for each expansion, the measurement electrodes can be varied accordingly to the trend above. Table IV below depicts a genericized version of the tables above.

TABLE IV

| Source or Sink Electrode No. (A) | Sink or Source Electrode No. (B) | Measurement electrode No. (M) | Read Electrode No. (N) | Alternate Measurement electrode(s) |
|---|---|---|---|---|
| 1 | A plus N | A plus 1 | A plus 2 | A + 3 to A + N − 1 |
| 2 | A plus N | 3 | 4 | A + 3 to A + N − 1 |
| 3 | A plus N | 4 | 5 | A + 3 to A + N − 1 |
| 4 | A plus N | 5 | 6 | A + 3 to A + N − 1 |
| 5 | A plus N | 6 | 7 | A + 3 to A + N − 1 |
| 6 | A plus N | 7 | 8 | A + 3 to A + N − 1 |
| 7 | A plus N | 8 | 9 | A + 3 to A + N − 1 |
| 8 | A plus N | 9 | 10 | A + 3 to A + N − 1 |
| 9 | A plus N | 10 | 11 | A + 3 to A + N − 1 |
| 10 | A plus N | 11 | 12 | A + 3 to A + N − 1 |
| 11 | A plus N | 12 | 13 | A + 3 to A + N − 1 |
| 12 | A plus N | 13 | 14 | A + 3 to A + N − 1 |
| 13 | A plus N | 14 | 15 | A + 3 to A + N − 1 |
| 14 | A plus N | 15 | 16 | A + 3 to A + N − 1 |
| 15 | A plus N | 16 | 17 | A + 3 to A + N − 1 |
| 16 | A plus N | 17 | 18 | A + 3 to A + N − 1 |
| 17 | A plus N | 18 | 19 | A + N − 1, A + N − 2 |
| 18 | A plus N | 19 | 20 | A + N − 1 |
| 19 | A plus N | 20 | 21 | N/A |

In the above table, N is the increment for each iteration. For a 22 electrode array, N can be 3, 4, 5, 6, 7, 8, 9, 10, 11, 12, 13, 14, 15, 16, 17, 18, 19, 20 or 21 (as limited by the top end—e.g., when A is electrode 16, N cannot be 20).

It is noted that while the read/measurement electrodes in the above tables are located between the source and sink electrodes, in some embodiments, as noted above, one measurement electrode is between the source and sink electrode, and one is outside/not in between the source and sink. Further, in some embodiments, both measurement electrodes are outside the source and sink (not between the source and sink).

Note also that in some embodiments, more than 2 measurement electrodes can be used for a given activation of a source and sink. Indeed, in some embodiments, for a given source and sink activation, 3, 4, 5, 6, 7, 8, 9, 10, 11, 12, 13, 14, 15, 16, 17, 18, 19 or 20 or more electrodes can be used as the measurement electrodes. For example, in the case where there electrodes 2 and 5 are the source and sink, electrode 3 and 4 and 6 and 7 and 8 and 9 and 10 etc. can simultaneously be the measurement electrodes (e.g., the voltage difference between electrodes 3 and 4, 3 and 6, 3 and 7, 3 and 8, 3 and 9, 3 and 10, 4 and 6, 4 and 7, 4 and 8, 4 and 9, 4 and 10, 6 and 7, 6 and 8, 6 and 9, 6 and 10, 7 and 8, 7 and 9, 7 and 10, 8 and 9, 8 and 10 and 9 and 10 can all potentially be simultaneously read or read in sequence in any order.

From the above, it can be seen that embodiments include expanding the trend above, one electrode at a time to expand the source and sink distance, while, for each expansion, the measurement electrodes can be varied accordingly to the trend above. Table V below depicts a genericized version based on the above.

TABLE V

| Source or Sink Electrode No. (A) | Sink or Source Electrode No. (B) | Measurement electrode No. (M) | Read Electrode No. (N) |
| --- | --- | --- | --- |
| 1 | A plus N | Not A and not A plus N | Not A and not A plus N and not M |
| 2 | A plus N | Not A and not A plus N | Not A and not A plus N and not M |
| 3 | A plus N | Not A and not A plus N | Not A and not A plus N and not M |
| 4 | A plus N | Not A and not A plus N | Not A and not A plus N and not M |
| 5 | A plus N | Not A and not A plus N | Not A and not A plus N and not M |
| 6 | A plus N | Not A and not A plus N | Not A and not A plus N and not M |
| 7 | A plus N | Not A and not A plus N | Not A and not A plus N and not M |
| 8 | A plus N | Not A and not A plus N | Not A and not A plus N and not M |
| 9 | A plus N | Not A and not A plus N | Not A and not A plus N and not M |
| 10 | A plus N | Not A and not A plus N | Not A and not A plus N and not M |
| 11 | A plus N | Not A and not A plus N | Not A and not A plus N and not M |
| 12 | A plus N | Not A and not A plus N | Not A and not A plus N and not M |
| 13 | A plus N | Not A and not A plus N | Not A and not A plus N and not M |
| 14 | A plus N | Not A and not A plus N | Not A and not A plus N and not M |
| 15 | A plus N | Not A and not A plus N | Not A and not A plus N and not M |
| 16 | A plus N | Not A and not A plus N | Not A and not A plus N and not M |
| 17 | A plus N | Not A and not A plus N | Not A and not A plus N and not M |
| 18 | A plus N | Not A and not A plus N | Not A and not A plus N and not M |
| 19 | A plus N | Not A and not A plus N | Not A and not A plus N and not M |

In the above table, the measurement electrodes are only limited as noted.

Also, in some embodiments, an extra-cochlea electrode can be used as the source or the sink electrode (in some embodiments, there is high utility for using the extra-cochlear electrode as the sink) for greater depth sensing. In which case, table V would result in the elimination of one of the electrodes as the source or sink and the inclusion of that electrode as one of the measurement electrodes.

To be clear, methods include any one or more permutations of the above, where data is obtained from the pertinent measurement electrodes. In some embodiments, every permutation is executed with the electrode array. In some embodiments, only some permutations are presented.

Figure 39:
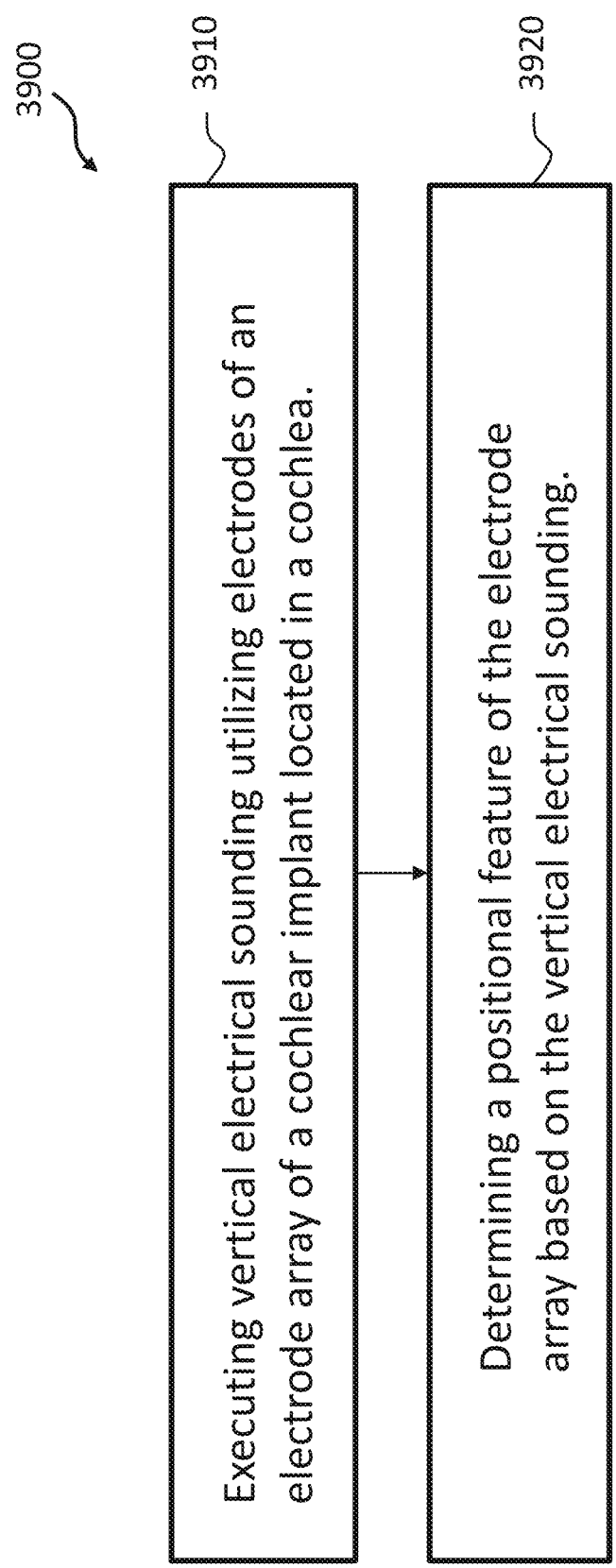

FIG. 39 presents another exemplary flowchart for an exemplary method, method 3900, which includes method action 3910, which includes executing vertical electrical sounding utilizing electrodes of an electrode array of a cochlear implant located in a cochlea. This is executed using any of the method actions, alone or in combination, detailed herein, or variations thereof, or any other technique that will enable vertical electrical sounding utilizing electrodes and electrode array of a cochlear implant located in the cochlea. Method 3900 also includes method action 3920, which includes determining a positional feature of the electrode array based on the vertical electrical sounding. In an exemplary embodiment, the determined positional feature is a distance of the electrode array from a modiolus wall of the cochlea. In an exemplary embodiment, the determined positional feature is a distance of the electrode array from a lateral wall of the cochlea. In an exemplary embodiment, the determined positional feature is respective distances from structure of the cochlea (lateral wall, modiolus wall, etc.) for one or more respective locations of the electrode array. For example, the one or more respective distances can be the respective distances from any one or more of electrodes 1, 2, 3, 4, 5, 6, 7, 8, 9, 10, 11, 12, 13, 14, 15, 16, 17, 18, 19, 20, 21, and/or 22 to the structure, and, if an array with more electrodes are present, for those additional electrodes. For example, these can be distances from locations L9, L10, L11, L12, L13, L14, L15, L16, and L17 in FIG. 5A, and for the other electrodes not shown accordingly. In an exemplary embodiment, the one or more respective distances can be the respective distances from any location in between, including the location on the electrode array in the geometric center (e.g., 50% of the way between) between any group of two or more electrodes 1, 2, 3, 4, 5, 6, 7, 8, 9, 10, 11, 12, 13, 14, 15, 16, 17, 18, 19, 20, 21, and/or 22 to the structure, and, if an array with more electrodes are present, for those additional electrodes. For example, these can be distances from locations L1, L2, L3, L4, L5, L6, L7 and L8 in FIG. 5A, and for other respective locations for the electrodes not shown.

In an exemplary embodiment, relative to distance from the distal tip of the electrode array, the one or more respective distances can be the respective distances from any one or more locations at or about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9. 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0 cm along the array from the tip, depending on the length of the array, of course, or any value or range of values therebetween in 0.01 cm increments, providing that the array enables such.

In an exemplary embodiment of the method action 3920, the determined positional feature is a tip fold over of the electrode array. In an exemplary embodiment, this is determined by determining distances for respective locations along the array from a given structure of the cochlea, and determining that a distance value or values "does not make sense" relative to other distance values other than in a scenario where there is a tip fold over (or that such is a possibility). Any data that results from vertical electrical tomography or any of the other techniques detailed herein that can be utilized to determine or otherwise estimate that a tip fold over has occurred, can be utilized in at least some exemplary embodiments.

In an exemplary embodiment, the determined positional feature of method action 3920 is a puncture of the electrode array through a wall of the cochlea. Again, such a determination can be achieved, in an exemplary embodiment, by evaluating or otherwise determining distances for respective locations along the array from a given structure of the cochlea, and determining that a distance value or values is inconsistent with a properly positioned array, and is otherwise indicative of an array that has punctured a wall of the cochlea. In an exemplary embodiment, the determined positional feature of method action 3920 is in over insertion of the electrode array to the cochlea, while in some embodiments of the method action 3920, the determined positional feature is a longitudinal location of the electrode array within the cochlea. It is noted that the various positional features detailed herein are not mutually exclusive when executing method action 3920. That is, in an exemplary embodiment, the method action 3920 is executed, a number of different positional features can be determined based on a single set of data.

Figure 40:
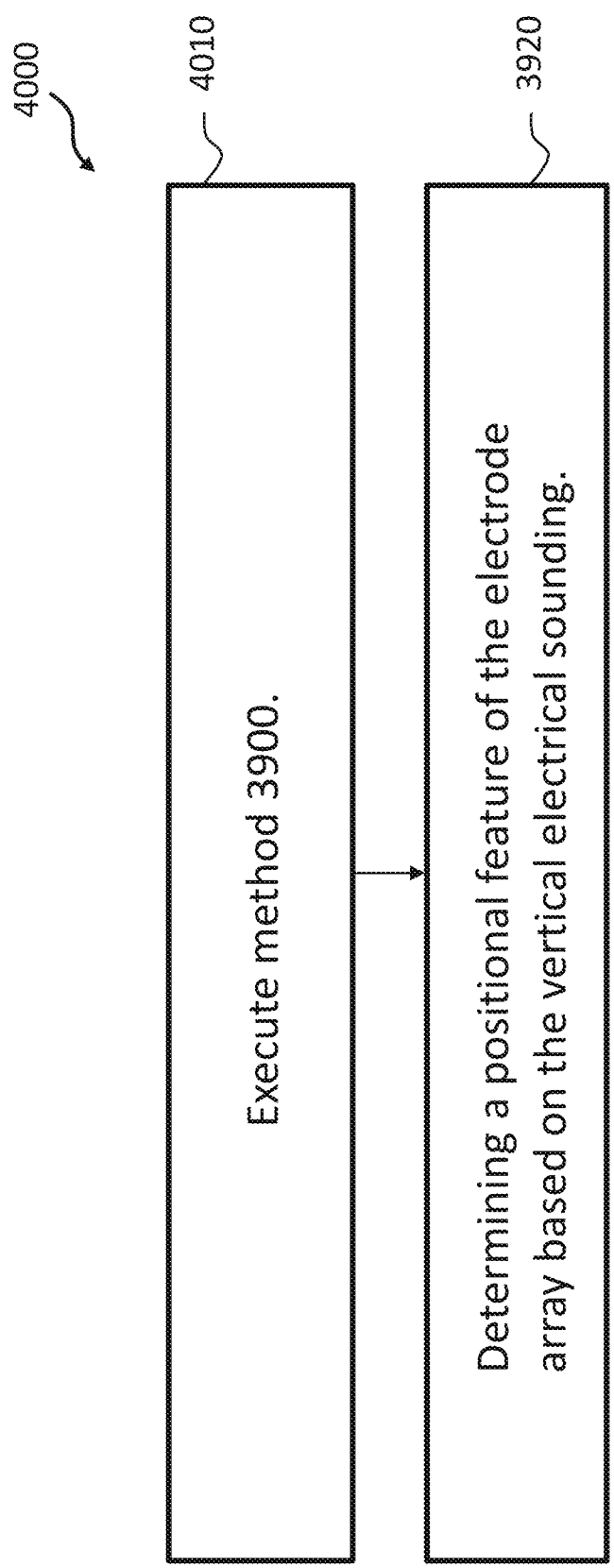

In some exemplary embodiments, there is an exemplary method, such as method 4000 represented by the flow chart on FIG. 40, wherein the method includes method action 4010, which includes executing method 3900, which results in the determined positional feature being a longitudinal location of the electrode array within the cochlea. Method 4000 also includes method action 4020, which includes the action of determining based on the longitudinal location of the electrode array within the cochlea that an electrode array fixation failure has occurred. In an exemplary embodiment, method action 4020 is executed during the surgical process in which the electrode array has been inserted (e.g., subsequent to insertion, during closure of the access incision through the outer skin of the recipient, etc.), while in an exemplary embodiment, method action 4020 is executed after the recipient has left the surgery room. In an exemplary embodiment, method action 4020 is executed after 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 months or 3 or 4 or 5 or 6 or 7 or 8 or 9 or 10 years after implantation and fixture of the electrode array.

In an exemplary embodiment, the determined positional feature is a distance from fibrous tissue that has grown since the array was implanted in the recipient. In this regard, the determined position feature can be executed after 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 months or 3 or 4 or 5 or 6 or 7 or 8 or 9 or 10 years after implantation of the electrode array.

Figure 41:
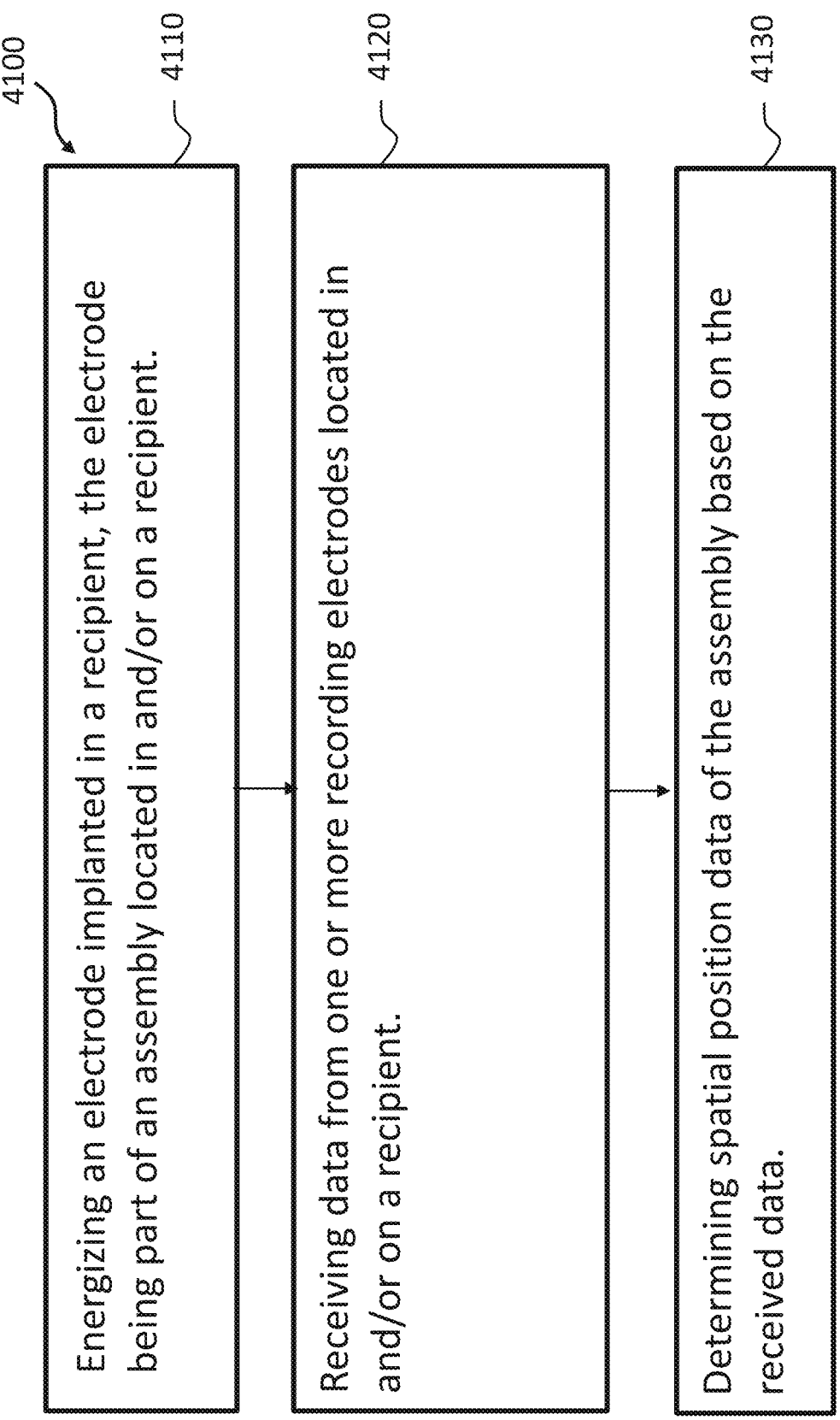

FIG. 41 presents a flowchart for an exemplary method, method 4100, which includes method action 4110, which includes energizing an electrode implanted in a recipient, the electrode being part of an assembly located in and/or on a recipient. In an exemplary embodiment, the assembly is an electrode array of a cochlear implant, and the electrode that is energized is intracochlear electrode array, although as noted above, in embodiments where an extra cochlear electrode array is utilized as the source under the sink, where such is utilized as the source, and extra cochlear electrode array can be energized. Method 4100 also includes method action 4120, which includes receiving data from one or more recording electrodes located in and/or on a recipient. In an exemplary embodiment, this can correspond utilizing the measurement electrodes that are located along the array as noted above. Method 4100 also includes method action 4130, which includes determining spatial position data of the assembly based on the received data. In an exemplary embodiment, the spatial position data can be any of the data detailed herein or variations thereof, such as the distance from the modiolus wall, etc.

As will be understood, in an exemplary embodiment, the actions of energizing, receiving, and determining can be, in some embodiments, actions that are part of a vertical electrical sounding method applied to a mammal.

It is noted that by spatial position data, such does not include mere indicators that an event has occurred (e.g., that the electrode array has moved, etc.). The spatial position data obtained in method action 4130 is data that indicates a position of the array.

In an exemplary embodiment of method action 4130, the spatial position data of the assembly is a distance of the assembly from a wall of tissue of the recipient (e.g., the modiolus wall, etc.). In an exemplary embodiment, the wall of tissue of the recipient is a wall that is a barrier of a cavity in the recipient that normally contains bodily fluid. In an exemplary embodiment, the wall of tissue of the recipient is a modiolus wall of a cochlea, the assembly is an electrode array of a cochlear implant, the electrode is located in a duct of the cochlea, and the spatial position is distance of the electrode array from the modiolus wall relative to the one or more recording electrodes or a location between two or more of the recording electrodes (anywhere between, such as a location 50% of the way between two electrodes). In some exemplary embodiments where the assembly is a cochlear electrode array, method 4100 includes determining, based on the determined spatial position data (e.g., such as the distance from the modiolus wall, or other structure of the cochlea, for one or more locations along the electrode array), that at least one or more of the following has occurred:

(i) a tip fold over;
(ii) a longitudinally local lateral angular position of the electrode array has shifted relative to another longitudinally local position;
(iii) the electrode array has been over inserted into a cochlea of the recipient;
(iv) the electrode array has become unfixed subsequent to full implantation into the recipient; or
(v) the electrode array has migrated during implantation.

Consistent with the teachings detailed herein, in an exemplary embodiment of method 4100 where the assembly is an electrode array assembly, the spatial position data can be a plurality of respective distance of the assembly at respective locations along the array from respective locations of a wall of tissue of the recipient.

Figure 42:
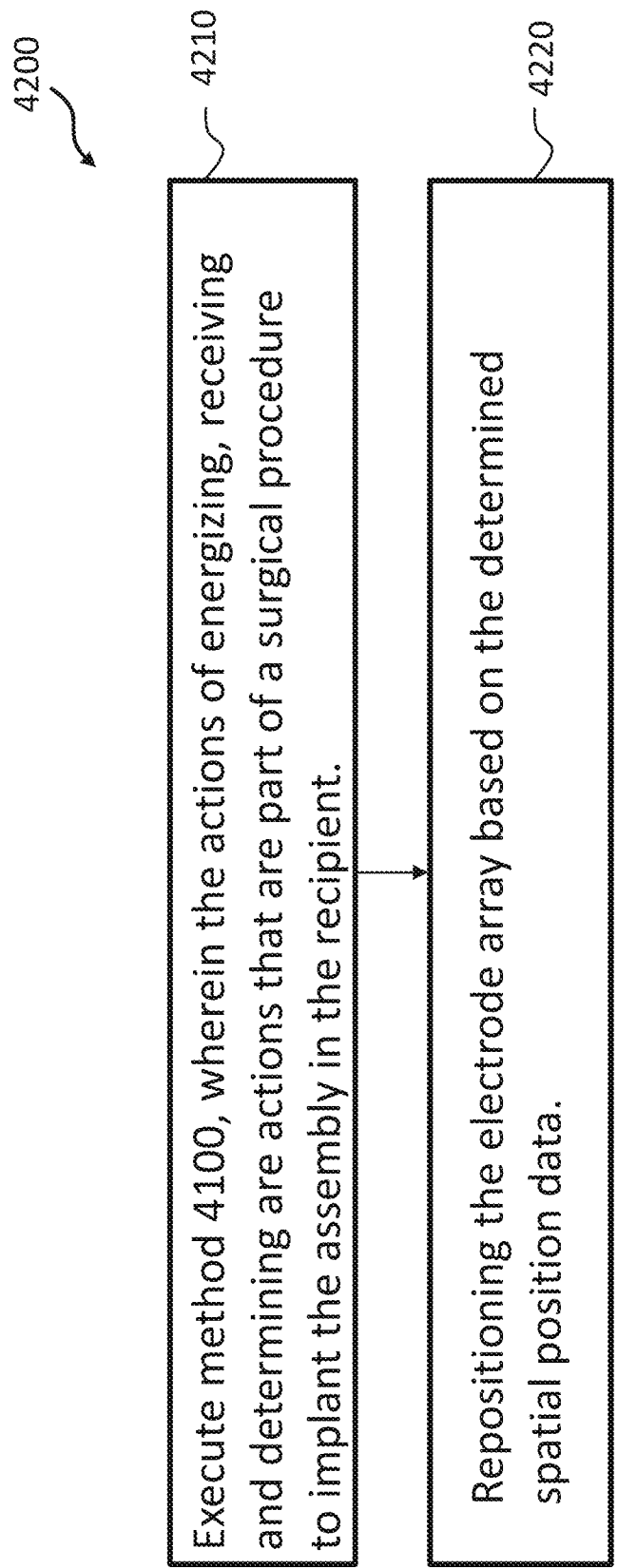

FIG. 42 presents a flowchart for an exemplary method, method 4200, which includes method action 4210, which includes executing method 4100, wherein the actions of energizing, receiving and determining are actions that are part of a surgical procedure to implant the assembly in the recipient. Method 4200 further includes method action 4220, which comprises repositioning the electrode array based on the determined spatial position data. In this regard, in an exemplary embodiment, the spatial positioning data, such as the distance from the modiolus wall, for example, can be evaluated to determine that the electrode array is at a position that is less than utilitarian relative to that which would otherwise be the case if the electrode array was positioned at another location, such as by way of example only and not by way of limitation, at a location where one or more locations along the electrode array are located closer to the modiolus wall. Thus, in an exemplary embodiment, based on the spatial positioning data, when the determination is made that the electrode array should be repositioned, method action 4220 can be executed based on that data.

Figure 43:
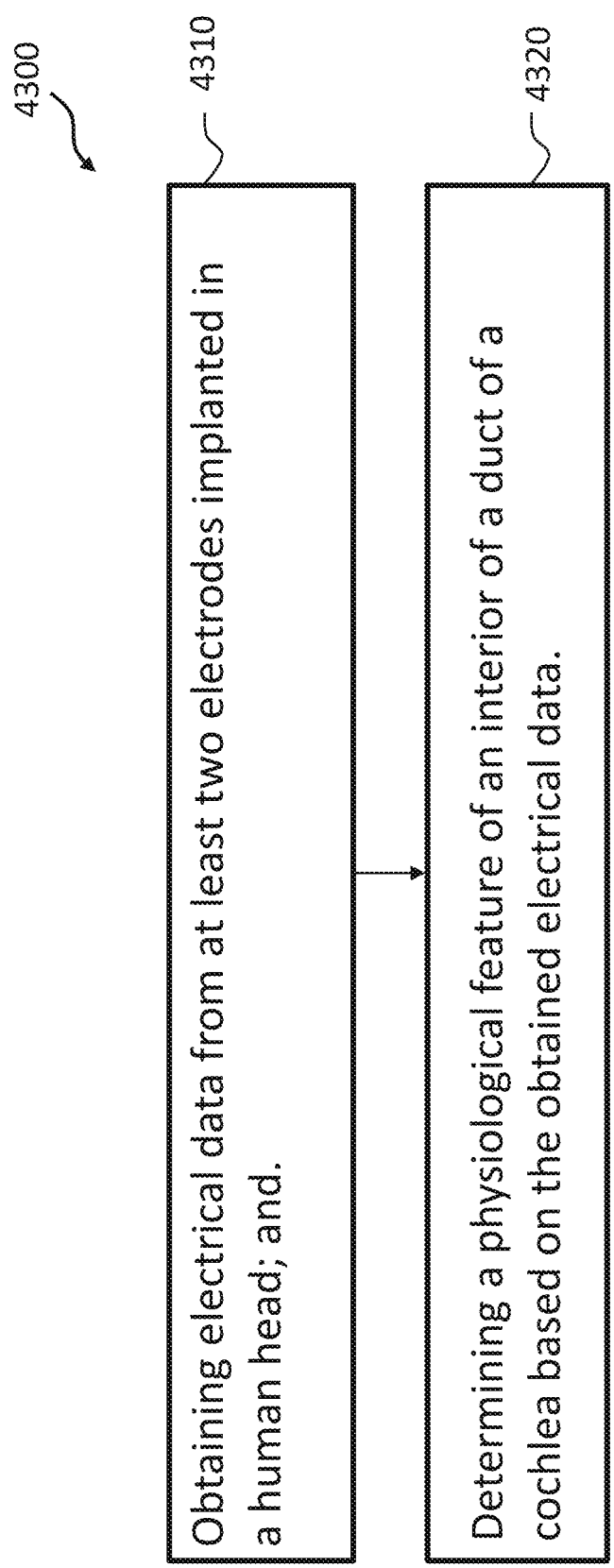

FIG. 43 presents an exemplary flowchart for an exemplary method, method 4300, which includes method action 4310, which includes obtaining electrical data from at least two electrodes implanted in a human head, such as by implementing the teachings detailed herein and/or variations thereof, such as by using a cochlear electrode array. Method 4300 also includes method action 4320, which includes determining a physiological feature of an interior of a duct of a cochlea based on the obtained electrical data. In an exemplary embodiment, the determined physiological feature is the relative absence of perilymph in the duct, while in some other embodiments, the determined physiological feature is the relative absence of fibrous tissue growth due to implantation of the electrode array into the duct of the cochlea (the latter having utilitarian value when method action 4320 is executed after 5, 6, 7, 8, 9, 10, 11, 12, 13, 14, 15, 16, 17, 18, 19, 20, 21, 22, 23, 24, 25, 26, 27, 28, 29, or 30 days or 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 months or 3 or 4 or 5 or 6 or 7 or 8 or 9 or 10 years after implantation of the electrode array). In an exemplary embodiment, the determined physiological feature is the presence of significant fibrous tissue growth due to implantation of the electrode array into the duct of the cochlea (again, which can have utilitarian value when executed after 5, 6, 7, 8, 9, 10, 11, 12, 13, 14, 15, 16, 17, 18, 19, 20, 21, 22, 23, 24, 25, 26, 27, 28, 29 or 30 days or 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 months or 3 or 4 or 5 or 6 or 7 or 8 or 9 or 10 years after implantation of the electrode array).

Figure 44:
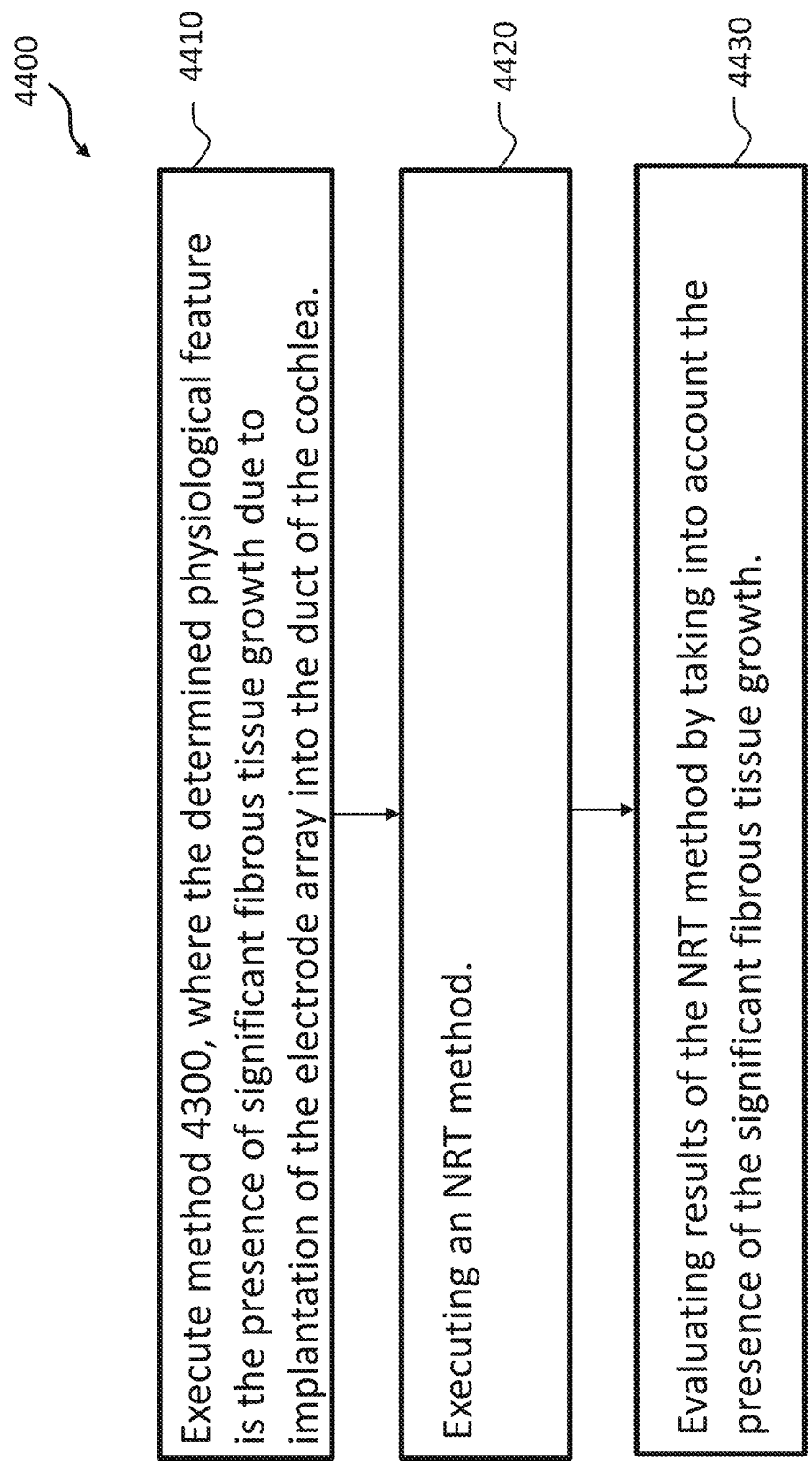

FIG. 44 depicts an exemplary flowchart for an exemplary method. Method 4400, which includes method action 4410, which includes executing method 4300, where the determined physiological feature is the presence of significant fibrous tissue growth due to implantation of the electrode array into the duct of the cochlea. Method 4400 also includes method action 4420, which includes executing NRT (Neural Response Telemetry) method, such as by using the electrodes of a cochlear electrode array implanted in a cochlea. In this regard, in an exemplary embodiment, cochlear implants according to some embodiments are configured to enable the execution of an NRT method. Method 4400 further includes method action 4430, which includes evaluating results of the NRT method by taking into account the presence of the significant fibrous tissue growth. In this regard, in an exemplary embodiment, the presence of significant fibrous tissue growth can skewer otherwise change the results of the NRT method. In an exemplary embodiment, by discounting the results of the NRT method based on the presence of the fibrous tissue growth, more utilitarian value of the NRT method can be obtained. In an exemplary embodiment, the method of method 4400 also includes the action of determining that the fibrous tissue has established a dead patch with respect to taking NRT measurements.

It is noted that sometimes, NRT is referred to in the art as evoked compound action potentials (ECAP).

In an exemplary embodiment, there is a cochlear implant configured to execute one or more of the actions detailed herein, which cochlear implant is configured to communicate the results of such actions to control unit 8310. Corollary to this is that control unit 8310 can be configured to activate the receiver/stimulator of the cochlear implant to execute one or more of the method actions detailed herein, such as the measurements/the collection of the data. In an alternative embodiment, the receiver/stimulator of the cochlear implant can execute such autonomously. The receiver/stimulator of the cochlear implant, can, in some embodiments, be configured to transmit the data based on or otherwise resulting from the execution of one or more of the method actions to the control unit 8310. Control unit 8310 analyzes the data in some embodiments. Indeed, in some embodiments, at least based in part on that data, control unit 8310 can control an automated robot that inserts an electrode array into a cochlea.

In an exemplary embodiment, the cochlear implant can be configured to take NRT/ECAP measurements to obtain the NRT/ECAP data, which cochlear implant is configured to communicate the results of such measurements to control unit 8310. In this regard, the ECAP measurement device/ECAP data collection device can correspond to a receiver/stimulator of a cochlear implant, which has an inductance coil and can be utilized as detailed above, albeit with respect to measuring ECAP or otherwise developing or collecting ECAP data and conveying such measurements to the control unit 8310. Corollary to this is that control unit 8310 can be configured to activate the receiver/stimulator of the cochlear implant to execute the measurements/the collection of the data. In an alternative embodiment, the receiver/stimulator of the cochlear implant can execute such autonomously. The receiver/stimulator of the cochlear implant, can transmit the data based on or otherwise resulting from the execution of NRT/ECAP measurements to the control unit 8310. Control unit 8310 analyzes the data in some embodiments, and, at least based in part on that data, in some embodiments, can control an automated robot that inserts an electrode array into a cochlea.

It is noted that in some exemplary embodiments, the electrode arrays detailed herein are utilized to obtain data analogous to the data obtained via Electrical resistivity tomography (ERT) or electrical resistivity imaging (ERI), and in some embodiments, the electrode array is utilized to execute such. These techniques are traditionally geophysical techniques for imaging sub-surface structures from electrical resistivity measurements made at the surface. Accordingly, where the electrode array of the cochlear implant is used to execute such techniques, such can be used to obtain imaging.

For example, induced polarization, measures the transient response. In some embodiments, the cochlear implant and/or the system of which it is apart, such as the control unit noted above, are configured to execute 1D, 2D and/or 3D Electrical Resistivity Tomography (ERT).

In an exemplary embodiment, the above-noted action of obtaining electrical data from at least two electrodes implanted in a human head includes doing so as part of an ERT/ERI method, and the action of determining a physiological feature of an interior of a duct of a cochlea based on the obtained electrical data results in an image.

Figure 45:
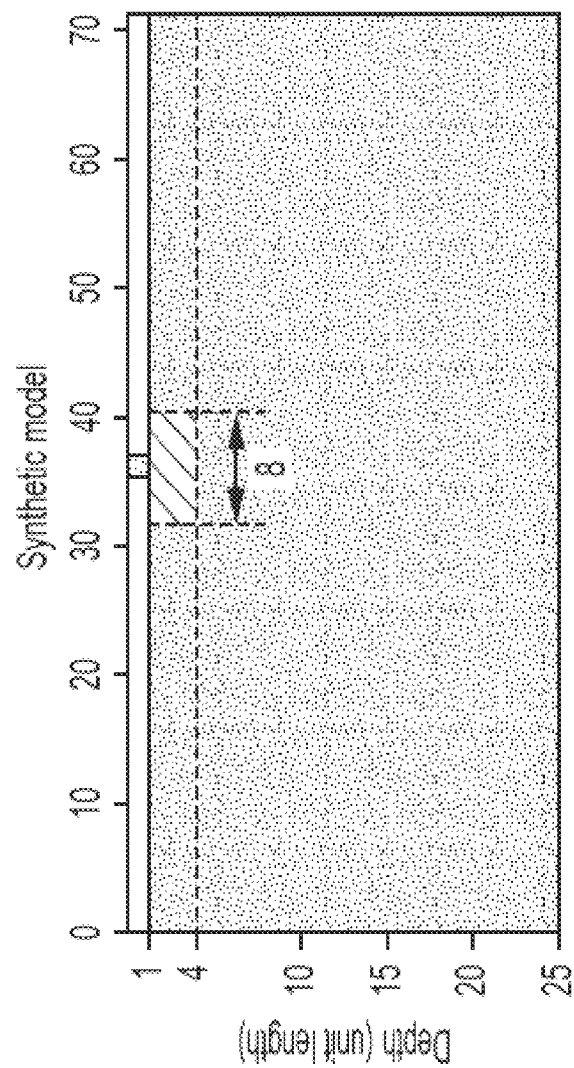
FIGS. 45-47 depict schematics of data resulting from some embodiments.
Figure 46:
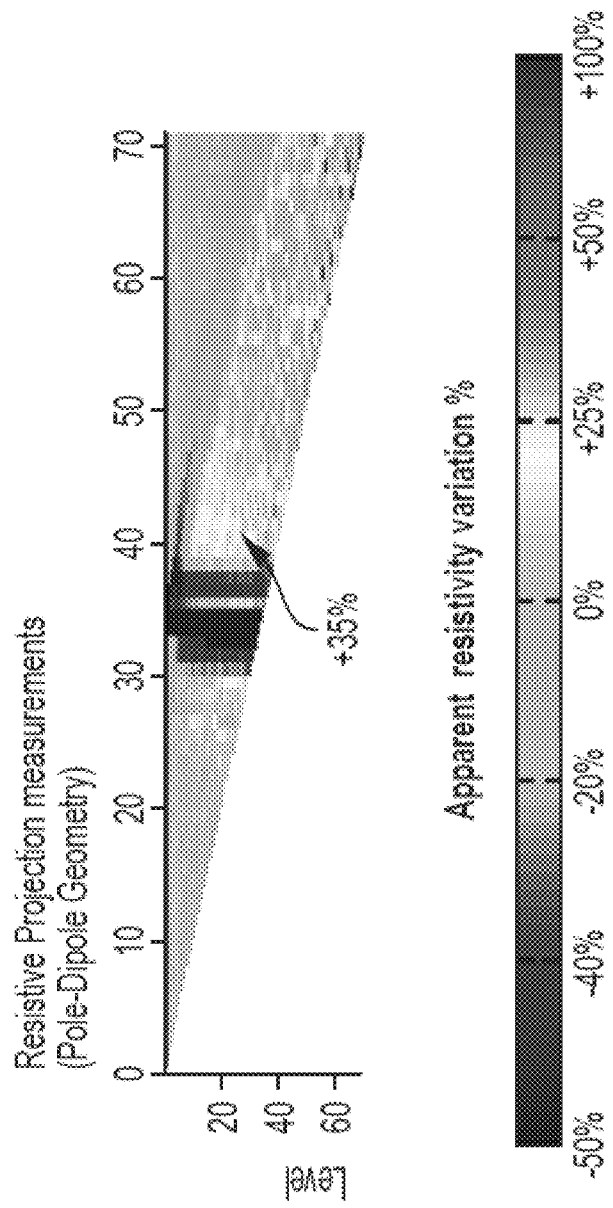
Figure 47:
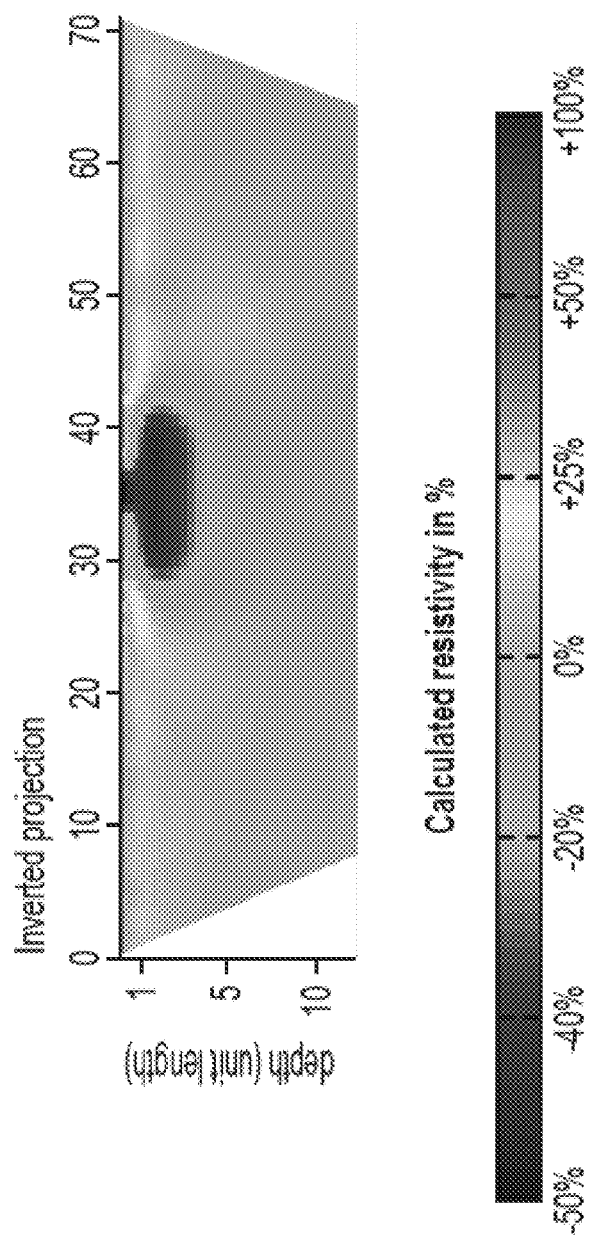

FIG. 45 depicts an image that results from a synthetic model, and FIG. 46 depicts an image that results from resistive projection measurements, and FIG. 47 depicts an image of an inverted projection, where darker colors are lower impedance. In an exemplary embodiment, these images are obtained using ERT/ERI via a cochlear electrode array inserted into a cochlea, to obtain image information associated with the cochlea.

It is noted that any equations and/or theories detailed herein are presented for purposes of explanation and conceptual understanding only. In some embodiments, such equations and theories may be applicable. In other embodiments, such equations and theories may not be applicable, or otherwise may be applicable only with further modifications or variations. By way of example only and not by way of limitation, while some of the equations presented above are for a hemispherical scenario owing to the fact that air acts as an insulator when utilized in the geological regime, such is not the case with respect to utilization of an electrode array that is located in a cochlea that is filled with perilymph.

Still further, below is presented some exemplary teachings that can have utilitarian value with respect to at least some exemplary embodiments. It is noted that the below is for purposes of explaining some embodiments, in other embodiments may not utilize some or all of the following teachings. It is noted that in some exemplary embodiments, there are methods systems and/or apparatuses that use some or all of the following teachings. In this regard, in an exemplary embodiment, there is a method that is executed to obtain various data/results detailed herein utilizing one or more of the following teachings. In an exemplary embodiment, there is an apparatus and/or system that is configured to obtain various data/results detailed herein utilizing one or more of the following teachings. In this regard, in an exemplary embodiment, there is a system and/or apparatus that includes structure to execute some or all of the following teachings. By way of example only and not by way of limitation, in an exemplary embodiment, such structure can be a personal computer or the like that is programmed to achieve such goals, which personal computer is in signal communication with a controller of an electrode array that is implanted in a cochlea or the like. That said, in an alternate embodiment, the personal computer can be configured to receive data obtained by use of the controller of the electrode array, which data can be downloaded or the like or otherwise provided to the computer system (e.g., such as via utilization of a flash drive or the like, which flash drive contains data obtained from the cochlear implant). It is further noted that in at least some exemplary embodiments, computational techniques are utilized to obtain values or estimates for the various data/results detailed herein.

During electrical stimulation of the cochlea, a voltage dipole is generated between the stimulating electrode pair. Assuming a purely resistive system (our spherical chicken in a vacuum) the charge (q) on each electrode, of the dipole, is equal to the applied current.

Figure 48:
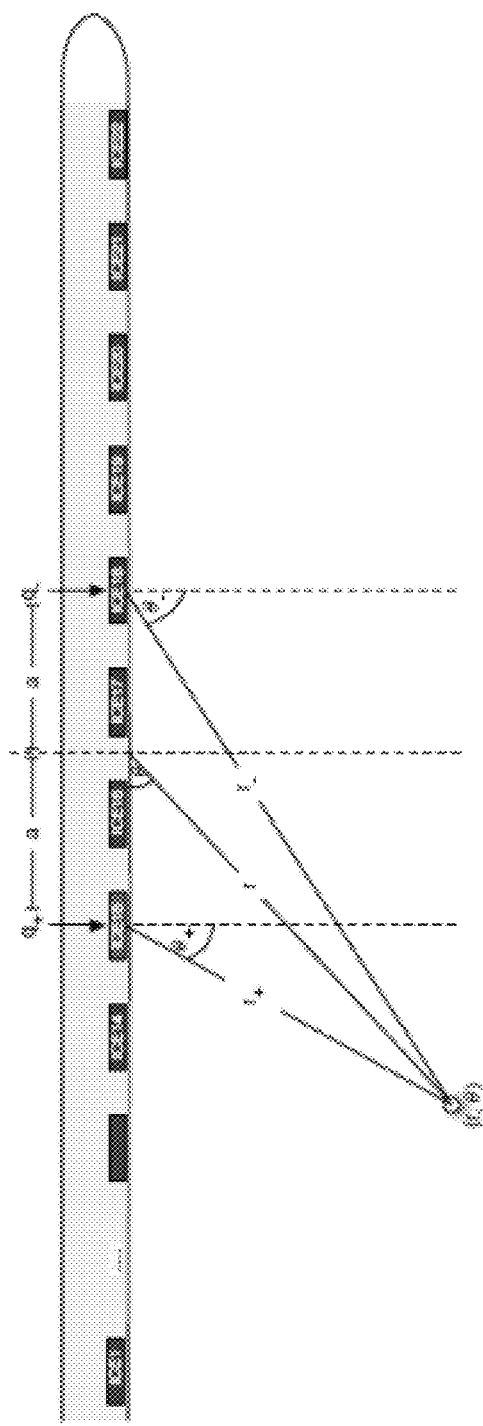
FIGS. 48 and 50 and 51 and 55 present respective schematics associated with an electrode array.

This is seen by way of example in FIG. 48, which depicts a stimulating electrode array.

In a homogeneous medium of admittance (σ) The voltage potential generated by the dipole, at point (r, θ), is determined as the super position of two charge sources, as defined in Equation 1.

$$V_{(r,\theta)} = \frac{1}{4\pi\sigma}\left(\frac{q}{r_+} - \frac{q}{r_-}\right) \quad \text{Equation 1}$$

Voltage due to dipole($r_+ = r^2 + a^2 - 2ra\cos(\theta)$, $r_- = r^2 + a^2 + 2ra\cos(\theta)$)

The differential of the voltage field gives the electric field.

$$E_{(r,\theta)} = \nabla V_{(r,\theta)}$$

Equation 2: Electric field from the voltage gradient

The current density (J) at depth r is determined by the electric field induced in the medium multiplied by the admittance of the medium, Equation 3.

$$J_{(r,\theta)} = \sigma E_{(r,\theta)}$$

Equation 3: Current Density

Thus integrating current density across a region and multiplying it by the area of the region will result in estimate the actual current flowing through a specific region.

Figure 49:
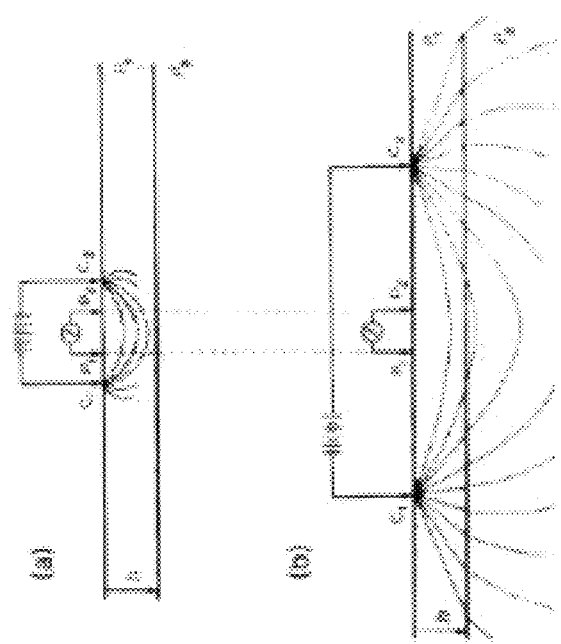
FIG. 49 presents a schematic of a conceptual dipole.

What is clear from these equations is that the amount of current flowing at depth 'r' is inversely proportional to the cube of the depth, i.e. we have a lower sensitivity to deep regions then shallow regions, but also that the sensitivity of the depth is proportional to the spacing of the dipole as shown in FIG. 49.

Indeed, in geophysical applications, which typically only consider only hemispherical voltage gradients because the air is an insulator, the total fraction of the current flowing ($i_f$) shallower then depth z can be approximated by Equation 4. Note that for a completely immersed fully metallic electrode in a homogeneous medium this would be halved, as half the current will be flowing above the electrode also.

$$i_f = \frac{2}{\pi}\tan^{-1}\left(\frac{z}{a}\right) \quad \text{Equation 4}$$

Total fraction of current flowing shallower then depth z. Note a is the separation in FIG. 48.

Applying Equation 4 we observe that at its deepest 50 percent of the current sensitivity lies within the region of z=a, and around 70% of the current is flowing at a depth equal to the electrode separation.

It is not only the stimulating electrodes which determine the sensitivity of the measurement to depth. The sense electrodes "image" a portion of the gradient, and thus have their main sensitivity restricted to the region between the electrodes.

Figure 50:
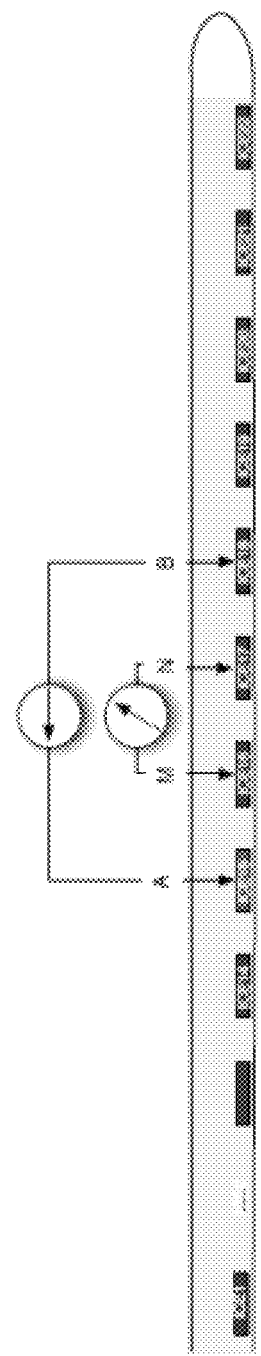

For example; the Kumar four-point impedance method, which involves a BP+3 stimulation and recording between the intermediate two electrodes, shown in FIG. 50 (this matches the wenner/schlumberger array when n=1).

Would only measure the effects of the electric field between electrodes M and N, in addition the cross sectional area is restricted to the region between M and N when calculating impedance. A geometrical factor needs to be calculated to compensate for the area of sensitivity between the recording electrodes.

If we refer to the separation between electrodes by their initial pairs (i.e. |AM| is the distance between electrodes A and M), then using Equation 1, the voltage electrode M ($V_M$) would be defined as Equation 5. The voltage at the second recording electrode would be the same equation substituting N for M.

$$V_M = \frac{I}{4\pi\sigma}\left(\frac{1}{|AM|} - \frac{1}{|MB|}\right) \quad \text{Equation 5}$$

Voltage At electrode M based on dipole AB.

Thus the voltage measured by the recording pair would be as described by Equation 6.

$$V_{MN} = V_M - V_N = \frac{I}{4\pi\sigma}\left[\left(\frac{1}{|AM|} - \frac{1}{|MB|}\right) - \left(\frac{1}{|AN|} - \frac{1}{|NB|}\right)\right] \quad \text{Equation 6}$$

Voltage measured between electrode pair MN

If we set k to equal the following, $$k = 4\pi\left[\left(\frac{1}{|AM|} - \frac{1}{|MB|}\right) - \left(\frac{1}{|AN|} - \frac{1}{|NB|}\right)\right]^{-1}$$

then the whole equation can be re written as Equation 7, which is the standard impedance calculation, with correction factor k for the geometry of the current spread. (Note that if we treat the silicone of the electrode array as an insulator it may make more sense to halve the geometric factor as in the 2D plane current will not flow above the array.)

$$\frac{1}{\sigma} = \rho = \frac{V_{MN}}{I}k \qquad \text{Equation 7}$$

Calculation of impedance ($\rho$) based on voltage and current measurement

Assuming constant electrode spacing the geometric factor k=4π|MN| for the Kumar method, assuming symmetrical conductance either side of the electrode array. If we assume current only flows towards the modiolus then the geometric factor becomes k=2π|MN|.

As the Kumar method is symmetrical the deepest penetration will occur in the center of the array. i.e when $r=r_+=r_-$ in Equation 1. In Cartesian co-ordinates, with the origin at the positive electrode this is x=|AB|/2. Since we are only interested in the horizontal current component we are looking to solve Equation 3, with respect to x.

$$J_x = -\sigma \frac{dV}{dx} = -\frac{I}{2\pi}\frac{d}{dx}\left[\frac{1}{r_+} - \frac{1}{r_-}\right] = \qquad \text{Equation 8}$$

$$-\frac{I}{4\pi}\frac{d}{dx}\left[\frac{1}{\sqrt{x^2+y^2}} - \frac{1}{\sqrt{(x-|AB|)^2+y^2}}\right] =$$

$$-\frac{I}{4\pi}\left[\frac{x}{\sqrt{x^2+y^2}^3} - \frac{x-|AB|}{\sqrt{(x-|AB|)^2+y^2}^3}\right] =$$

$$-\frac{I}{4\pi}\left[\frac{x}{r^3} - \frac{x-|AB|}{r^3}\right] = \frac{I}{4\pi}\frac{|AB|}{r^3}$$

Horizontal Current density in the center of the array ($r_+ = r_- = r$)

Thus the fraction of current ($\delta I$) flowing at depth (y) can be calculated as $J_x dy$, Using our calculated value of $J_x$ from Equation 8 gives Equation 9.

$$\delta I_x = \frac{I}{4\pi}\frac{|AB|}{\sqrt{\left(\frac{|AB|}{2}\right)^2 + y^2}^3} dy \qquad \text{Equation 9}$$

Current ($\delta I$) flowing through of thickness dy.

Thus the total current flowing through segment $I_x$ in the region bounded by $y_1$ and $y_2$ is obtained by integrating $J_x$ dy between y1 and y2 as shown in $$I_x = \int_{y_1}^{y_2} J_x dy = \frac{I}{4\pi}\int_{y_1}^{y_2}\frac{|AB|}{\sqrt{\left(\frac{|AB|}{2}\right)^2 + y^2}^3} dy = \qquad \text{Equation 10}$$

$$\frac{I}{\pi}\left[\tan^{-1}\frac{2y_2}{|AB|} - \tan^{-1}\frac{2y_1}{|AB|}\right]$$

Current flowing through region at $x = AB/2$

If we take the limit as $y_2 \to \infty$, we obtain the total proportion of current flowing below a depth of $y_1$.

$$I_x = \frac{I}{\pi}\left[\frac{\pi}{2} - \tan^{-1}\frac{2y_1}{|AB|}\right] \qquad \text{Equation 11}$$

Proportion of current flowing below depth $y_1$ for the full spherical voltage gradient.

Thus if we have an inhomogeneity at a depth of 1.5 electrode separations, ~10% of the applied current will penetrate to this depth so even if this inhomogeneity had infinite impedance it will increase the measured impedance by no more than ~10% (Sensitivity to depth is doubled if assume current can only propagate in one direction, as per geophysics)

Within a depth of half an electrode separation 75% of the current flow can be accounted for (50% if we use the geophysical assumption).

Note that the depth analysis here holds for the setup shown in FIG. 50, and will change depending on the geometry of the measurement electrodes with respect to the stimulating electrode pair, but fundamentally, the wider the stimulating electrodes are spaced the more sensitive the measurement is to inhomogeneity at depth.

Using this technique widening the stimulating electrode dipole while keeping the measurement pair unchanged. By convention, the depth of investigation is specified as the median current depth. i.e. the depth at which equal current flows above and below in a homogenous medium.

Figure 51:
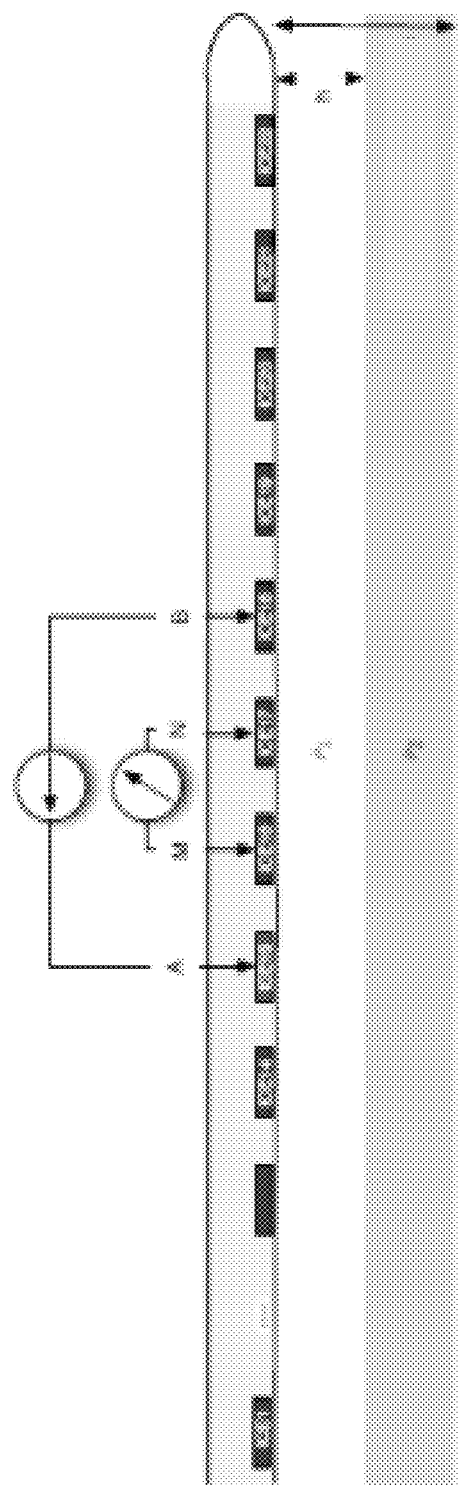

We can model the cochlea as a 2 layer system. i.e. the electrode array is in perilymph with the second layer as otic bone as shown in FIG. 51.

Figure 52:
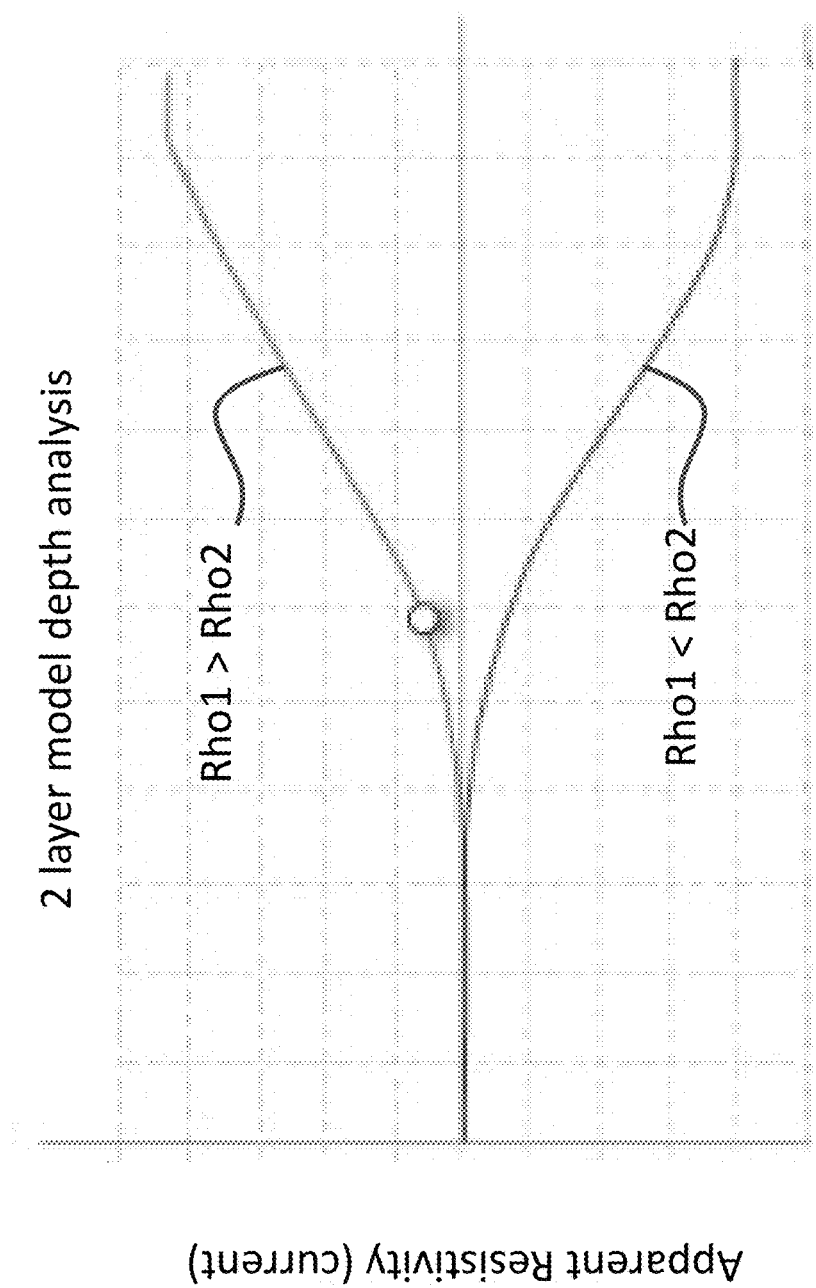
FIG. 52 presents a chart of conceptual data.

If we keep the recording electrode pair constant and widen the stimulating dipole, equivalent to using a schlumberger array, it is possible to plot the measured impedance vs median depth of current as shown in FIG. 52, where the different lines show expected behavior for changes in values of $\rho_1$ and $\rho_2$ with respect to each other. Note that the apparent resistivity values are for illustrative purposes only. Note Additional layers will introduce additional knee points in the impedance graph.

Figure 53:
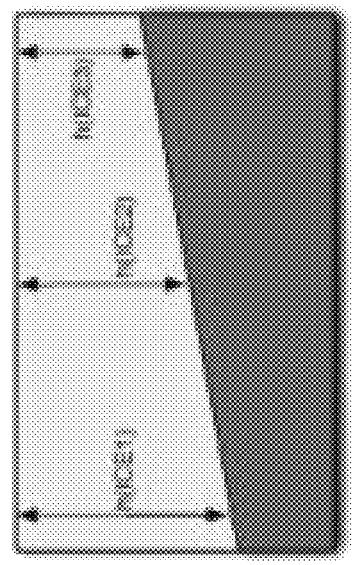
FIG. 53 presents a conceptual schematic of different heights relative to an array.

A number of depth estimates at different electrodes can be combined to produce a depth profile as shown in FIG. 53, which shows a profile of layer "depth" measured at different electrodes.

There are a number of methods for estimating the depth of the inhomogeneity:
1. The knee point, marked with a circle in FIG. 52, sits at the approximate depth of the second layer;
2. Forward modelling, adapting parameters ($\rho_1$, $\rho_2$ and h) to get a matching curve;
3. Mathematical Inversion methods.

Figure 54:
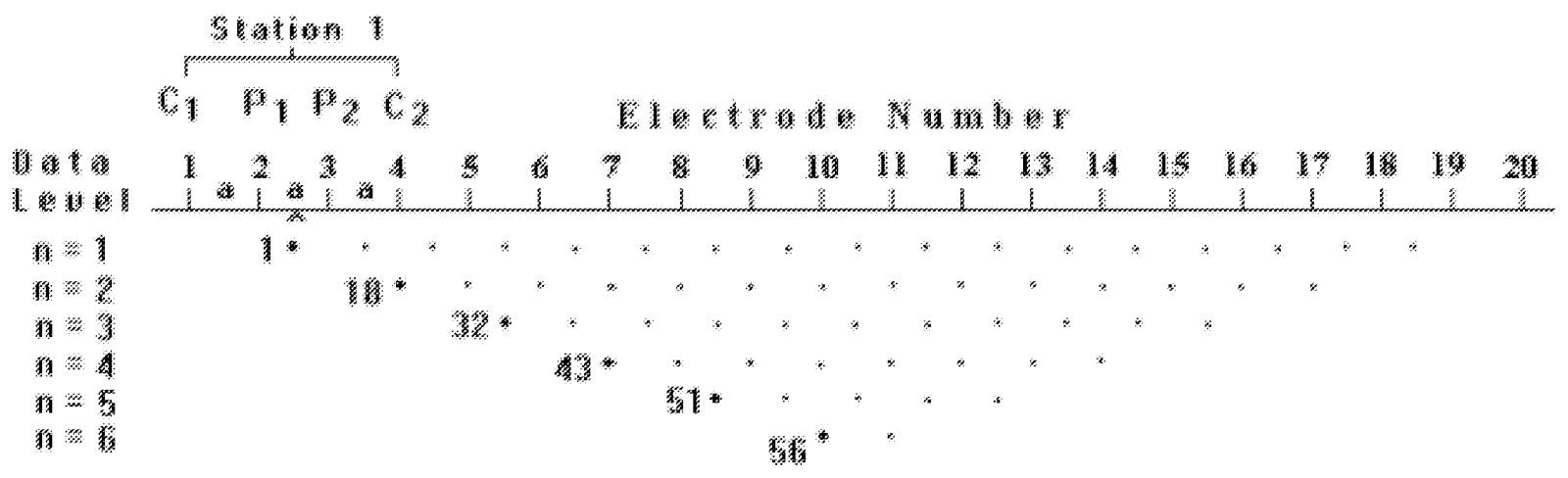

Some embodiments include creating Impedance Sections. In this regard, an alternative method of representing the measured data is to produce an impedance section. Such a section is a mapping of measurement points. Where the x axis of measurement is the center of the recording dipole, and the depth of the measurement is determined as the median current depth of the dipole at the point of measurement, as shown in FIG. 54. Which depicts a pseudo section of a Wenner array.

It is noted that the output becomes effectively a finite element mesh and can be solved as such.

In an exemplary embodiment, generation of pseudo sections (FIG. 46) from a synthetic model (FIG. 45) to calculate inversions FIG. 47 can be executed. Some embodiments include compensating for topography. We can combine these with depth of insertion measurements or a cochlear size measurements/estimation to achieve an approximate topological correction factor.

As the pseudo section is effectively an FEA matrix, we can warp the matrix according to a logarithmical spiral. Even if the size estimation is incorrect, it should be sufficient to achieve good estimates.

Figure 55:
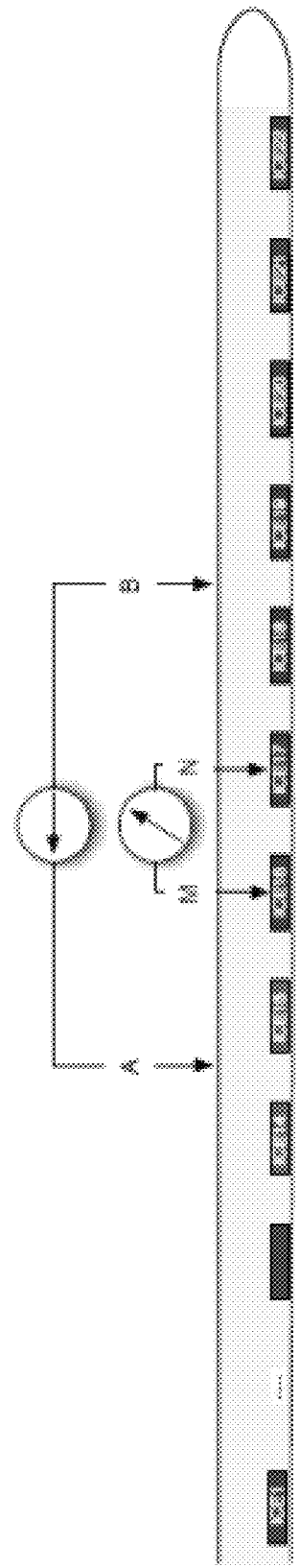

Some embodiments relate to increasing depth resolution. In this regard, note that the actual stimulating electrode position, the math is determined by the separation of the stimulating dipole, so sub electrode depth resolution can be achieved by stimulating using a double electrode array so that the centroid of the dipole is half way between the combined electrodes as shown in FIG. 55.

Note that in a homogeneous medium the centroid of charge will appear halfway between the active electrode pair (ICE14 & ICE15) with the negative charge centroid between (ICE18 & ICE19). Thus we have successfully widened the dipole by less than an electrode spacing. This applies for multipolar stimulation also.

Figure 56:
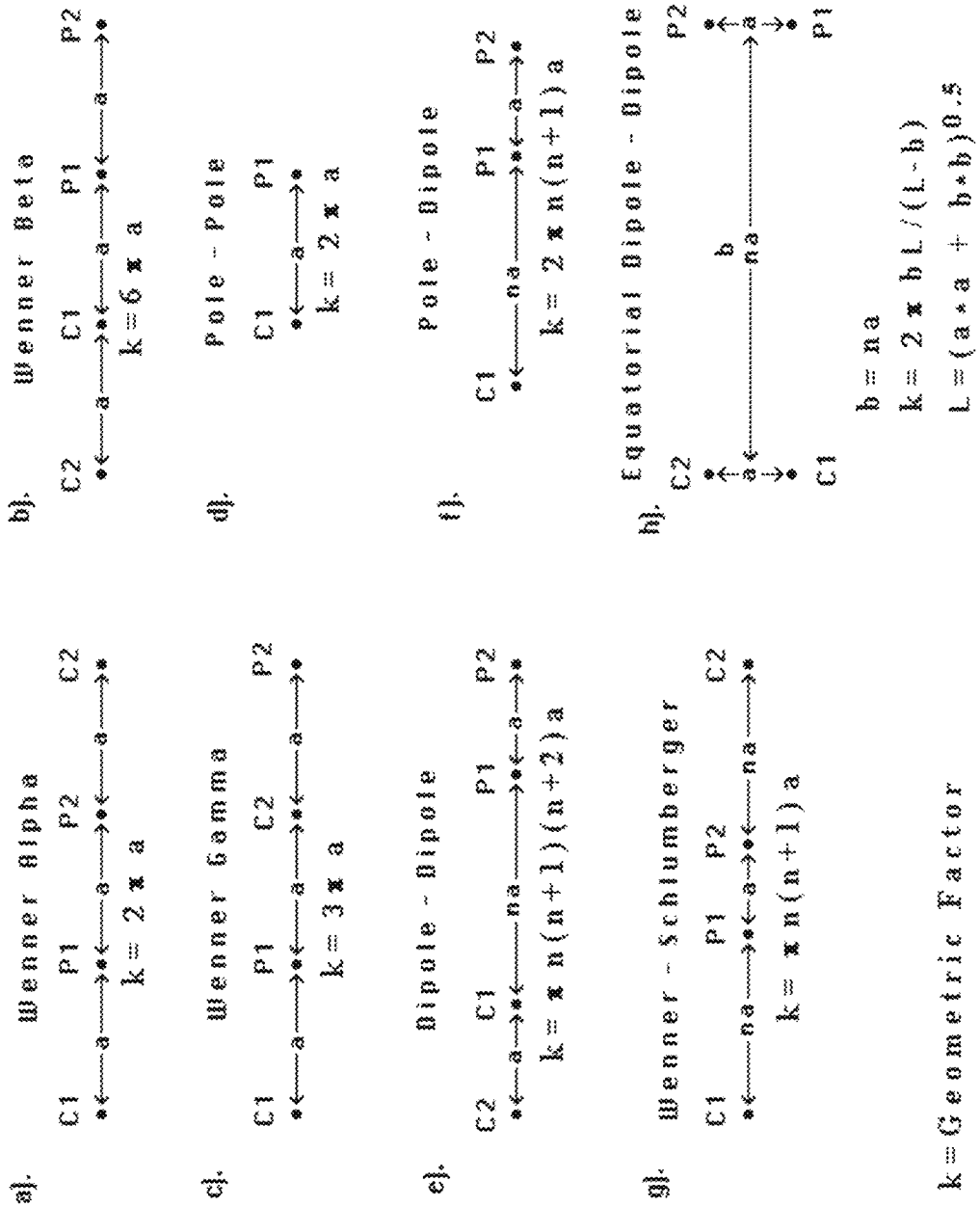
FIG. 56 presents conceptual data in a two dimensional manner.

Some embodiments also address alternative dipole confiigurations. Note that there are a number of different array types, and are listed in FIG. 56, with their geometric factors. They each provide a tradeoff between resolution, depth of penetration and signal strength.

Note that some configurations, such as the pole-dipole, are asymmetrical and will likely require measurements with a reversed setup to mitigate for some of the asymmetry observed in the output.

There are mathematical inversion methods, such as recursive Bessel for stratified layers, as shown in the lecture notes by Richard M. Allen, Introduction to Applied Geophysics Berkley University, such as Tangent Law: The electrical current is bent at a boundary, as represented by way of example in FIG. 57.

Figure 58:
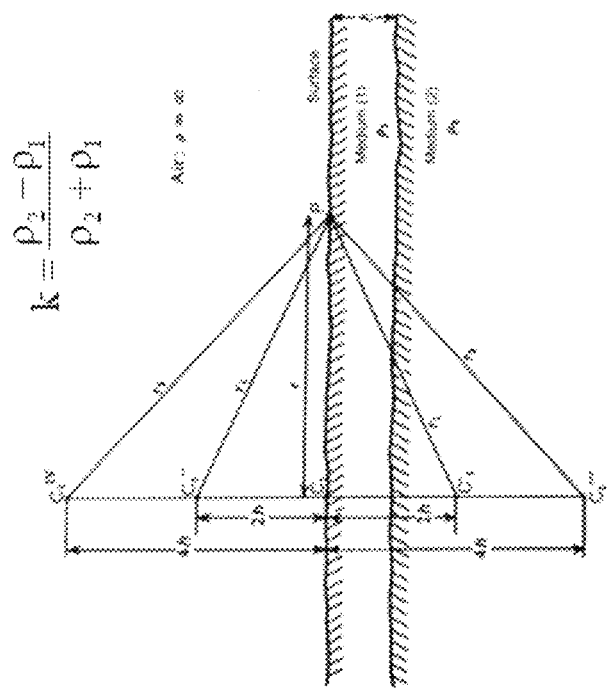

With reference to FIG. 58, one can use for image theory for multiple boundaries, for two layer cases:

$$V_p = \frac{I\rho_1}{2\pi}\left(\frac{1}{r} + \frac{2k}{r_1} + \frac{2k^2}{r_2} + \ldots + \frac{2k^n}{r_n} + \ldots\right) = \frac{I\rho_1}{2\pi}\left(\frac{1}{r} + 2\sum_{n=1}^{\infty}\frac{k^n}{r_n}\right)$$

where $$r_n = \sqrt{r^2 + (2nh)^2}$$

The integral method can be based on:

$$V_p = \frac{I\rho_1}{2\pi}\int_0^{\infty} K(\lambda)J_0(\lambda r)d\lambda$$

J0 is the Bessel function of zero order.
K(λ) given by relationship:

$$K(\lambda) = \frac{T_1(\lambda)}{\rho_1}$$

Figure 59:
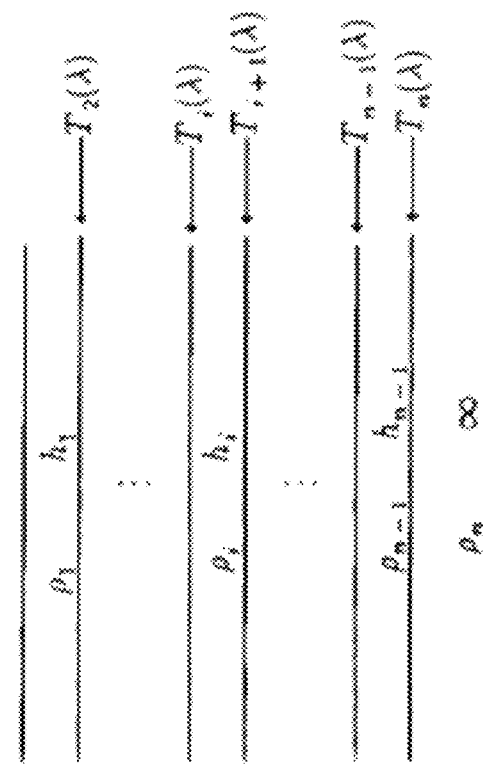
FIGS. 58 and 59 present additional conceptual schematics of a theory of operation.

Ti(Δ) solved for recursively upward from bottom layer to layer 1 using, with reference to FIG. 59:

$$T_i(\lambda) = \frac{[T_{i+1} + \rho_i\tanh(\lambda h_i)]}{[1 + T_{i+1}\tanh(\lambda h_i)/\rho_i]} \text{ where}$$

-continued $$\tanh(\lambda h_i) = \frac{e^{2\lambda h_i} - 1}{e^{2\lambda h_i} + 1} \text{ and}$$

$$T_n(\lambda) = \rho_n$$

Some embodiments include matrix inversion techniques and/or polarization measurements and/or time domain decay techniques. In this regard, Polarisability metric is area under then IPG divided by the peak voltage Vm. Note we can use the trapazoidal rule, provided we can get two measurements on the IPG. This should be good enough.

Figure 60:
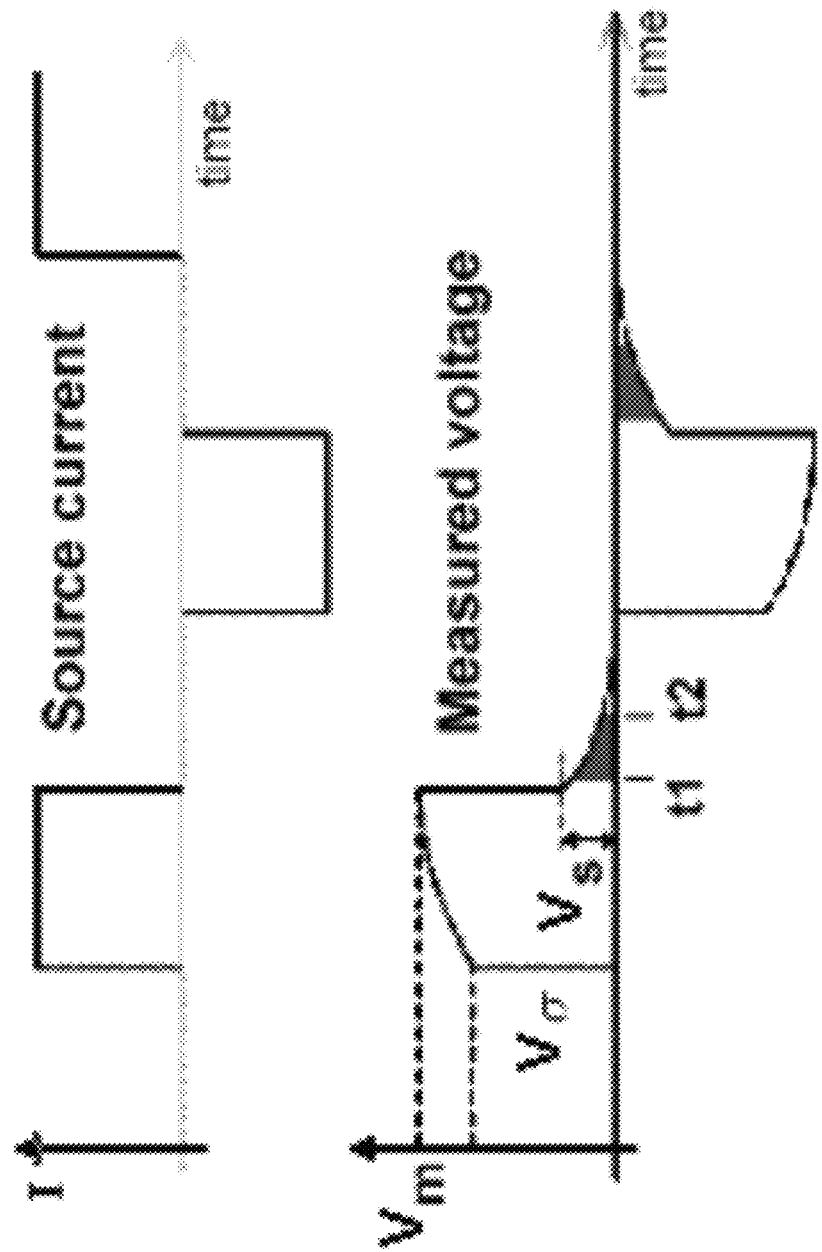
FIG. 60 presents exemplary waveforms.

FIG. 60, presents a graphic illustrating the above.

Some embodiments include spectral induced Polarisation methods. This relies on a high resolution of IPG sampling, i.e. will need to adjust the IPG at each spectral frequency to get multiple sample points on the decay curve. A minimum of 10 are recommended.

$$\rho(\omega) = \rho_0\left[1 - m_0\left(1 - \frac{1}{1 + (j\omega\tau)^\alpha}\right)\right] \quad \text{Equation 12}$$

Cole-Cole model for Complex inpedance, where $\rho_0$=Resistivity
$m_0$=Intrisic Chargeability (First point measured on the decay curve)
$\omega$=Frequency
$\tau$=Decay Time Constant (approx. 90%-10% decay time of IPG)
$\alpha$=parameter controlling frequency dependence (c=1 is simple exponential decay)
Time domain decay curve can be defined by $$m(t) = m_0\sum_{n=0}^{\infty}\frac{(-1)^n\left(\frac{t}{\tau}\right)^{n\alpha}}{\Gamma(1 + n\alpha)} \quad \text{Equation 13}$$

Time domain intrinsic chargeability curve, where

Γ is the Gamma function. The aim is to use forward modelling using Equation 13 to get best fit of the measured decay curve.

In an exemplary embodiment, there is a method, comprising, obtaining electrical data from at least two electrodes implanted in a human head and determining a physiological feature of an interior of a duct of a cochlea based on the obtained electrical data. In an exemplary embodiment of the method as described above and/or below, the determined physiological feature is the relative absence of perilymph in the duct. In an exemplary embodiment of the method as described above and/or below the determined physiological feature is the relative absence of fibrous tissue growth due to implantation of the electrode array into the duct of the cochlea. In an exemplary embodiment of the method as described above and/or below the determined physiological feature is the presence of significant fibrous tissue growth due to implantation of the electrode array into the duct of the cochlea. In an exemplary embodiment of the method as described above and/or below, the method further includes executing an NRT method, and evaluating results of the NRT method by taking into account the presence of the significant fibrous tissue growth. In an exemplary embodiment of the method as described above and/or below, the method further comprises determining that the fibrous tissue has established a dead patch with respect to taking NRT measurements. In an exemplary embodiment of the method as described above and/or below, the the determined physiological feature is a second puncture in a wall of the cochlea in addition to that through which the electrode array entered the cochlea.

In an exemplary embodiment, there is a method, comprising energizing an electrode implanted in a recipient, the electrode being part of an assembly located in and/or on a recipient, receiving data from one or more recording electrodes located in and/or on a recipient, and determining spatial position data of the assembly based on the received data. In an exemplary embodiment of this method, the actions of energizing, receiving and determining are actions that are part of a surgical procedure to implant the assembly in the recipient, the method further comprises repositioning the electrode array based on the determined spatial position data.

Many of the above teachings are found in appendix A and U.S. Provisional Application No. 62/476,295, filed Mar. 24, 2017, entitled ADVANCED ELECTRODE ARRAY LOCATION EVALUATION, which appendix is included in this application in its entirety and the subject matter of that application is included herein in its entirety by incorporation by reference. In an exemplary embodiment, one or more or all of the teachings detailed in appendix A (where any reference to Appendix A herein also refers by reference to U.S. Provisional Application No. 62/476,295, filed Mar. 24, 2017, entitled ADVANCED ELECTRODE ARRAY LOCATION EVALUATION) and one or more or all of the teachings detailed in U.S. Provisional Application No. 62/476,295, filed Mar. 24, 2017, entitled ADVANCED ELECTRODE ARRAY LOCATION EVALUATION, are combined with one or more or all of the teachings found in appendix F, which appendix is included in the application in its entirety. In this regard, in an exemplary embodiment, there is a method that includes executing one or more of the method actions in appendix A along with one or more of the method actions detailed in appendix F. By way of example only and not by way of limitation, in an exemplary embodiment, there is a method that includes inserting an electrode array into a cochlea while executing the depth sounding method actions disclosed in appendix A along with the execution of the ECOG method actions disclosed in appendix F, in a manner where the actions do not interfere with one another, at least not to a degree that eliminates the efficacy of one or more method actions or at least not substantially reduces the efficacy of one or more the method actions. It is also noted that embodiments include a device and/or system as disclosed in appendix A in combination with a device and/or system as disclosed in appendix F, and in some embodiments, there is a single device and/or a single system and/or a compilation of devices and/or systems that have one or more of the functionalities of any device and/or system in appendix A as well as one or more of the functionalities of any device and/or system in appendix F.

Moreover, there is a device and/or system and/or a combination thereof that is configured to execute any one or more of the method actions in appendix A in an automated and/or semi automated manner and that is also configured to execute any one or more of the method actions in appendix F. Corollary to this is that in an exemplary method, there is a method that includes methods corresponding to that which results from the functionality of any one or more of the functionalities disclosed in appendix A in combination with any one or more of the functionalities disclosed in appendix F.

The present application also includes the subject matter disclosed in appendix B and U.S. Provisional Application No. 62/559,782, filed Sep. 18, 2017, entitled ADVANCED ELECTRODE ARRAY INSERTION WITH CONDITIONING, which appendix is included in this application in its entirety and the subject matter of that application is included herein in its entirety by incorporation by reference. In an exemplary embodiment, one or more or all of the teachings detailed in appendix B (where any reference to Appendix B herein also refers by reference to U.S. Provisional Application No. 62/559,782, filed Sep. 18, 2017, entitled ADVANCED ELECTRODE ARRAY INSERTION WITH CONDITIONING) and one or more or all of the teachings detailed in U.S. Provisional Application No. 62/559,782, filed Sep. 18, 2017, entitled ADVANCED ELECTRODE ARRAY INSERTION WITH CONDITIONING, are combined with one or more or all of the teachings found in appendix F, which appendix is included in the application in its entirety.

In this regard, in an exemplary embodiment, there is a method that includes executing one or more of the method actions detailed in appendix B along with one or more of the method actions detailed in appendix F. By way of example only and not by way of limitation, in an exemplary embodiment, there is a method that includes inserting an electrode array into a cochlea while executing the tip fold over identification actions of appendix B along with the execution of the ECOG method actions disclosed in appendix F, in a manner where the actions do not interfere with one another, at least not to a degree that eliminates the efficacy of one or more method actions or at least not substantially reduces the efficacy of one or more the method actions. It is also noted that embodiments include a device and/or system as disclosed in appendix B in combination with a device and/or system as disclosed in appendix F, and in some embodiments, there is a single device and/or a single system and/or a compilation of devices and/or systems that have one or more of the functionalities of any device and/or system in appendix B as well as one or more of the functionalities of any device and/or system in appendix F.

Moreover, there is a device and/or system and/or a combination thereof that is configured to execute any one or more of the method actions in appendix B in an automated and/or semi automated manner and that is also configured to execute any one or more of the method actions in appendix F. Corollary to this is that in an exemplary method, there is a method that includes methods corresponding to that which results from the functionality of any one or more of the functionalities disclosed in appendix B in combination with any one or more of the functionalities disclosed in appendix F.

The present application also includes the subject matter disclosed in appendix C and U.S. Provisional Application No. 62/633,054, filed Feb. 20, 2018, entitled ADVANCED ELECTRODE DATA ANALYSIS, which appendix is included in this application in its entirety and the subject matter of that application is included herein in its entirety by incorporation by reference. In an exemplary embodiment, one or more or all of the teachings detailed in appendix C (where any reference to Appendix C herein also refers by reference to U.S. Provisional Application No. 62/633,054, filed Feb. 20, 2018, entitled ADVANCED ELECTRODE DATA ANALYSIS) and one or more or all of the teachings detailed in U.S. Provisional Application No. 62/633,054, filed Feb. 20, 2018, entitled ADVANCED ELECTRODE DATA ANALYSIS, are combined with one or more or all of the teachings found in appendix F, which appendix is included in the application in its entirety. In this regard, in an exemplary embodiment, there is a method that includes executing one or more of the method actions detailed in appendix C along with one or more of the method actions detailed in appendix F. By way of example only and not by way of limitation, in an exemplary embodiment, there is a method that includes inserting an electrode array into a cochlea while executing the derivative and/or gradient evaluations of appendix C along with the execution of the ECOG method actions disclosed in appendix F, in a manner where the actions do not interfere with one another, at least not to a degree that eliminates the efficacy of one or more method actions or at least not substantially reduces the efficacy of one or more the method actions. It is also noted that embodiments include a device and/or system as disclosed in appendix C in combination with a device and/or system as disclosed in appendix F, and in some embodiments, there is a single device and/or a single system and/or a compilation of devices and/or systems that have one or more of the functionalities of any device and/or system in appendix C as well as one or more of the functionalities of any device and/or system in appendix F.

Moreover, there is a device and/or system and/or a combination thereof that is configured to execute any one or more of the method actions in appendix C in an automated and/or semi automated manner and that is also configured to execute any one or more of the method actions in appendix F. Corollary to this is that in an exemplary method, there is a method that includes methods corresponding to that which results from the functionality of any one or more of the functionalities disclosed in appendix C in combination with any one or more of the functionalities disclosed in appendix F.

The present application also includes the subject matter disclosed in appendix D and U.S. Provisional Application No. 62/642,566, filed Mar. 13, 2018, entitled ELECTRICAL FIELD USAGE IN COCHLEAS, which appendix is included in this application in its entirety and the subject matter of that application is included herein in its entirety by incorporation by reference. In an exemplary embodiment, one or more or all of the teachings detailed in appendix D (where any reference to Appendix D herein also refers by reference to U.S. Provisional Application No. 62/642,566, filed Mar. 13, 2018, entitled ELECTRICAL FIELD USAGE IN COCHLEAS) and one or more or all of the teachings detailed in U.S. Provisional Application No. 62/642,566, filed Mar. 13, 2018, entitled ELECTRICAL FIELD USAGE IN COCHLEAS, are combined with one or more or all of the teachings found in appendix F, which appendix is included in the application in its entirety. In this regard, in an exemplary embodiment, there is a method that includes executing one or more of the method actions detailed in appendix D along with one or more of the method actions detailed in appendix F. By way of example only and not by way of limitation, in an exemplary embodiment, there is a method that includes inserting an electrode array into a cochlea while executing the anatomical identification method(s) of appendix D along with the execution of the ECOG method actions disclosed in appendix F, in a manner where the actions do not interfere with one another, at least not to a degree that eliminates the efficacy of one or more method actions or at least not substantially reduces the efficacy of one or more the method actions. It is also noted that embodiments include a device and/or system as disclosed in appendix D in combination with a device and/or system as disclosed in appendix F, and in some embodiments, there is a single device and/or a single system and/or a compilation of devices and/or systems that have one or more of the functionalities of any device and/or system in appendix D as well as one or more of the functionalities of any device and/or system in appendix F.

Moreover, there is a device and/or system and/or a combination thereof that is configured to execute any one or more of the method actions in appendix D in an automated and/or semi automated manner and that is also configured to execute any one or more of the method actions in appendix F. Corollary to this is that in an exemplary method, there is a method that includes methods corresponding to that which results from the functionality of any one or more of the functionalities disclosed in appendix D in combination with any one or more of the functionalities disclosed in appendix F.

The present application also includes the subject matter disclosed in appendix E and U.S. Provisional Application No. 62/647,896, filed Mar. 26, 2018, entitled ELECTRICAL TECHNIQUES FOR BIOMARKER DETECTION IN A COCHLEA, which appendix is included in this application in its entirety and the subject matter of that application is included herein in its entirety by incorporation by reference. In an exemplary embodiment, one or more or all of the teachings detailed in appendix E (where any reference to Appendix E herein also refers by reference to U.S. Provisional Application No. 62/647,896, filed Mar. 26, 2018, entitled ELECTRICAL TECHNIQUES FOR BIOMARKER DETECTION IN A COCHLEA) and one or more or all of the teachings detailed in U.S. Provisional Application No. 62/647,896, filed Mar. 26, 2018, entitled ELECTRICAL TECHNIQUES FOR BIOMARKER DETECTION IN A COCHLEA, are combined with one or more or all of the teachings found in appendix F, which appendix is included in the application in its entirety. In this regard, in an exemplary embodiment, there is a method that includes executing one or more of the method actions detailed in appendix E along with one or more of the method actions detailed in appendix F. By way of example only and not by way of limitation, in an exemplary embodiment, there is a method that includes inserting an electrode array into a cochlea while executing the blood presence method(s) of appendix E along with the execution of the ECOG method actions disclosed in appendix F, in a manner where the actions do not interfere with one another, at least not to a degree that eliminates the efficacy of one or more method actions or at least not substantially reduces the efficacy of one or more the method actions. It is also noted that embodiments include a device and/or system as disclosed in appendix E in combination with a device and/or system as disclosed in appendix F, and in some embodiments, there is a single device and/or a single system and/or a compilation of devices and/or systems that have one or more of the functionalities of any device and/or system in appendix E as well as one or more of the functionalities of any device and/or system in appendix F.

Moreover, there is a device and/or system and/or a combination thereof that is configured to execute any one or more of the method actions in appendix E in an automated and/or semi automated manner and that is also configured to execute any one or more of the method actions in appendix F. Corollary to this is that in an exemplary method, there is a method that includes methods corresponding to that which results from the functionality of any one or more of the functionalities disclosed in appendix E in combination with any one or more of the functionalities disclosed in appendix F.

In an exemplary embodiment, one or more or all of the teachings disclosed in appendix A and/or B, and/or C and/or D and/or E and/or F are combined with one or more or all of the teachings found in the other of appendix A and/or B and/or C and/or D and/or E and/or F. In this regard, in an exemplary embodiment, there is a method that includes executing one or more of the method actions disclosed in appendix A along with, in one option, one or more of the method actions disclosed in appendix B and/or along with, in another option, one or more of the method actions disclosed in appendix C, and/or along with, in another option, one or more of the method actions disclosed in appendix D and/or along with, in another option, one or more of the method actions disclosed in appendix E and/or along with, in another option, one or more of the method actions disclosed in appendix F.

Also, in an exemplary embodiment, there is a method that includes executing one or more of the method actions disclosed in appendix B, along with, in one option, one or more of the method actions disclosed in appendix A and/or along with, in another option, one or more of the method actions disclosed in appendix C, and/or along with, in another option, one or more of the method actions disclosed in appendix D and/or along with, in another option, one or more of the method actions disclosed in appendix E and/or along with, in another option, one or more of the method actions disclosed in appendix F. Also, in an exemplary embodiment, there is an apparatus and/or a system and/or a combination of either and/or both that is configured to execute at least two or more of the method actions of the just disclosed method.

Also, in an exemplary embodiment, there is a method that includes executing one or more of the method actions disclosed in appendix B along with, in one option, one or more of the method actions disclosed in appendix A and/or along with, in another option, one or more of the method actions disclosed in appendix C, and/or along with, in another option, one or more of the method actions disclosed in appendix D and/or along with, in another option, one or more of the method actions disclosed in appendix E and/or along with, in another option, one or more of the method actions disclosed in appendix F. Also, in an exemplary embodiment, there is an apparatus and/or a system and/or a combination of either and/or both that is configured to execute at least two or more of the method actions of the just disclosed method.

Also, in an exemplary embodiment, there is a method that includes executing one or more of the method actions disclosed in appendix C along with, in one option, one or more of the method actions disclosed in appendix A and/or along with, in another option, one or more of the method actions disclosed in appendix B and/or, and/or along with, in another option, one or more of the method actions disclosed in appendix D and/or along with, in another option, one or more of the method actions disclosed in appendix E and/or along with, in another option, one or more of the method actions disclosed in appendix F. Also, in an exemplary embodiment, there is an apparatus and/or a system and/or a combination of either and/or both that is configured to execute at least two or more of the method actions of the just disclosed method.

Also, in an exemplary embodiment, there is a method that includes executing one or more of the method actions disclosed in appendix D along with, in one option, one or more of the method actions disclosed in appendix A and/or along with, in another option, one or more of the method actions disclosed in appendix B and/or, and/or along with, in another option, one or more of the method actions disclosed in appendix C and/or along with, in another option, one or more of the method actions disclosed in appendix E and/or along with, in another option, one or more of the method actions disclosed in appendix F. Also, in an exemplary embodiment, there is an apparatus and/or a system and/or a combination of either and/or both that is configured to execute at least two or more of the method actions of the just disclosed method.

Also, in an exemplary embodiment, there is a method that includes executing one or more of the method actions disclosed in appendix E along with, in one option, one or more of the method actions disclosed in appendix A and/or along with, in another option, one or more of the method actions disclosed in appendix B and/or, and/or along with, in another option, one or more of the method actions disclosed in appendix C and/or along with, in another option, one or more of the method actions disclosed in appendix D and/or along with, in another option, one or more of the method actions disclosed in appendix F. Also, in an exemplary embodiment, there is an apparatus and/or a system and/or a combination of either and/or both that is configured to execute at least two or more of the method actions of the just disclosed method.

Also, in an exemplary embodiment, there is a method that includes executing one or more of the method actions disclosed in appendix F along with, in one option, one or more of the method actions disclosed in appendix A and/or along with, in another option, one or more of the method actions disclosed in appendix B and/or, and/or along with, in another option, one or more of the method actions disclosed in appendix C and/or along with, in another option, one or more of the method actions disclosed in appendix D and/or along with, in another option, one or more of the method actions disclosed in appendix E. Also, in an exemplary embodiment, there is an apparatus and/or a system and/or a combination of either and/or both that is configured to execute at least two or more of the method actions of the just disclosed method. (By way of example, there can be a method that has an action of appendix F, an action of Appendix A, an action of Appendix B, an action of appendix C, an action of Appendix D and an action of Appendix E. By way of example, there can be a method that has two actions of appendix F, an action of Appendix A, an action of Appendix C, an action of Appendix D and an action of Appendix E. By way of example, there can be a method that has one action of appendix F, an action of Appendix A, two actions of Appendix B, an action of Appendix D and no action of appendix E.)

Also, in an exemplary embodiment, there is an apparatus and/or a system and/or a combination of either and/or both that is configured to have the functionality of an apparatus and/or system disclosed in appendix A along with, in one option, one or more of the functionalities of an apparatus and/or system disclosed in appendix B and/or along with, in another option, one or more of the functionalities of an apparatus and/or system disclosed in appendix C, and/or along with, in another option, one or more of the functionalities of an apparatus and/or system disclosed in appendix D and/or along with, in another option, one or more of the functionalities of an apparatus and/or system disclosed in appendix E and/or along with, in another option, one or more of the functionalities of an apparatus and/or system disclosed in appendix F. Also, in an exemplary embodiment, there is a method that includes using the device(s) and/or system(s) and/or executing a method associated with the functionalities of the just disclosed device(s) and/or system(s).

Also, in an exemplary embodiment, there is an apparatus and/or a system and/or a combination of either and/or both that is configured to have the functionality of an apparatus and/or system disclosed in appendix B and/or along with, in one option, one or more of the functionalities of an apparatus and/or system disclosed in appendix A and/or along with, in another option, one or more of the functionalities of an apparatus and/or system disclosed in appendix C, and/or along with, in another option, one or more of the functionalities of an apparatus and/or system disclosed in appendix D and/or along with, in another option, one or more of the functionalities of an apparatus and/or system disclosed in appendix E and/or along with, in another option, one or more of the functionalities of an apparatus and/or system disclosed in appendix F. Also, in an exemplary embodiment, there is a method that includes using the device(s) and/or system(s) and/or executing a method associated with the functionalities of the just disclosed device(s) and/or system(s).

Also, in an exemplary embodiment, there is an apparatus and/or a system and/or a combination of either and/or both that is configured to have the functionality of an apparatus and/or system disclosed in appendix C along with, in one option, one or more of the functionalities of an apparatus and/or system disclosed in appendix A and/or along with, in another option, one or more of the functionalities of an apparatus and/or system disclosed in appendix B, and/or along with, in another option, one or more of the functionalities of an apparatus and/or system disclosed in appendix D and/or along with, in another option, one or more of the functionalities of an apparatus and/or system disclosed in appendix E and/or along with, in another option, one or more of the functionalities of an apparatus and/or system disclosed in appendix F. Also, in an exemplary embodiment, there is a method that includes using the device(s) and/or system(s) and/or executing a method associated with the functionalities of the just disclosed device(s) and/or system(s).

Also, in an exemplary embodiment, there is an apparatus and/or a system and/or a combination of either and/or both that is configured to have the functionality of an apparatus and/or system disclosed in appendix D along with, in one option, one or more of the functionalities of an apparatus and/or system disclosed in appendix A and/or along with, in another option, one or more of the functionalities of an apparatus and/or system disclosed in appendix B, and/or along with, in another option, one or more of the functionalities of an apparatus and/or system disclosed in appendix C and/or along with, in another option, one or more of the functionalities of an apparatus and/or system disclosed in appendix E and/or along with, in another option, one or more of the functionalities of an apparatus and/or system disclosed in appendix F. Also, in an exemplary embodiment, there is a method that includes using the device(s) and/or system(s) and/or executing a method associated with the functionalities of the just disclosed device(s) and/or system(s).

Also, in an exemplary embodiment, there is an apparatus and/or a system and/or a combination of either and/or both that is configured to have the functionality of an apparatus and/or system disclosed in appendix E along with, in one option, one or more of the functionalities of an apparatus and/or system disclosed in appendix A and/or along with, in another option, one or more of the functionalities of an apparatus and/or system disclosed in appendix B, and/or along with, in another option, one or more of the functionalities of an apparatus and/or system disclosed in appendix C and/or along with, in another option, one or more of the functionalities of an apparatus and/or system disclosed in appendix D and/or along with, in another option, one or more of the functionalities of an apparatus and/or system disclosed in appendix F. Also, in an exemplary embodiment, there is a method that includes using the device(s) and/or system(s) and/or executing a method associated with the functionalities of the just disclosed device(s) and/or system(s).

To be clear, there are various respective embodiments which respectively include any one or more of the respective teachings in appendix A/U.S. Provisional Application No. 62/476,295, filed Mar. 24, 2017, entitled ADVANCED ELECTRODE ARRAY LOCATION EVALUATION, appendix B/U.S. Provisional Application No. 62/559,782, filed Sep. 18, 2017, entitled ADVANCED ELECTRODE ARRAY INSERTION WITH CONDITIONING, appendix C/U.S. Provisional Application No. 62/633,054, filed Feb. 20, 2018, entitled ADVANCED ELECTRODE DATA ANALYSIS, appendix D/U.S. Provisional Application No. 62/642,566, filed Mar. 13, 2018, entitled ELECTRICAL FIELD USAGE IN COCHLEAS, appendix E/U.S. Provisional Application No. 62/647,896, filed Mar. 26, 2018, entitled ELECTRICAL TECHNIQUES FOR BIOMARKER DETECTION IN A COCHLEA and/or appendix F can be combined, providing that the art enables such.

In view of the above, it is to be understood that in some exemplary embodiments, there are methods that utilize voltage and/or impedance measurements in a variety of manners to achieve a variety of goals/outcomes. With respect to appendices A-E, which are generally directed towards the utilization of voltage and/or impedance measurements utilizing so-called four point impedance measurements, it can be seen that different measurements can be applied utilizing an electrode array as it is being inserted into the cochlea and/or after it is inserted to do various things, such as, for example, to determine a positional feature of the electrode array based on the vertical electrical sounding, determine spatial derivatives of electrical properties between electrodes of the electrode array; identify changes between voltage measurements at read electrodes between different temporal locations, detect a voltage change across the plurality of electrodes based on a monitored relative magnitude that is representative of a voltage change at a reference electrode, identify a presence of an asymmetry in the voltage measurements, focus readings from read electrodes of the electrode array at a same location within the cochlea relative to other locations within the cochlea while the electrode array is moving, determine a location, density and temporal feature of the impedance change, identify tip fold over, identify scala dislocation, determine a distance from modiolus of the array, identify a phenomenon that exists in the recipient, determine that the electrode array has reached a specific location in the cochlea, identify the presence or absence of blood in the cochlea, and/or determine, based on the telemetry, that a physical characteristic associated with the electrode array that is strictly local to the electrode array existed and/or exists. Combined with appendix F, embodiments can include one or more of the above actions interleaved with neural response measurements while the electrode array is being moved. All of these embodiments, in some embodiments, can be combined with the conditioning of information in the received telemetry and perform the analysis based on the conditioned information.

By way of example only and not by way of limitation, in an exemplary embodiment, there is a method that includes inserting an electrode array into a cochlea while executing the blood presence method(s) of appendix E along with the execution of the ECOG method actions disclosed in appendix F, in a manner where the actions do not interfere with one another, at least not to a degree that eliminates the efficacy of one or more method actions or at least not substantially reduces the efficacy of one or more the method actions. It is also noted that embodiments include a device and/or system as disclosed in appendix E in combination with a device and/or system as disclosed in appendix F, and in some embodiments, there is a single device and/or a single system and/or a compilation of devices and/or systems that have one or more of the functionalities of any device and/or system in appendix E as well as one or more of the functionalities of any device and/or system in appendix F.

Moreover, there is a device and/or system and/or a combination thereof that is configured to execute any one or more of the method actions in appendix E in an automated and/or semi automated manner and that is also configured to execute any one or more of the method actions in appendix F. Corollary to this is that in an exemplary method, there is a method that includes methods corresponding to that which results from the functionality of any one or more of the functionalities disclosed in appendix E in combination with any one or more of the functionalities disclosed in appendix F.

Thus, in an exemplary embodiment, there is a method, comprising, starting at temporal location 1 and ending at temporal location 2, wherein temporal location 1 can correspond to any of the times between the first entry of the electrode array into the cochlea to a time where the surgeon determines that the electrode array is fully inserted into the cochlea, or any time. There between, or in some other embodiments, time periods that begin before and end after the aforementioned temporal locations, inserting a cochlear implant electrode array into a cochlea. However, in this exemplary embodiment, the temporal location 1 is the location where the first electrode enters the cochlea and temporal location 2 is where the last electrode enters the cochlea. The method further includes at least at various times between location 1 and location 2, measuring voltages between various electrodes of the electrode array. This can be done according to any of the teachings of appendices A, B, C, D and/or E in some embodiments. The method further includes analyzing some and/or all of the measured voltages, and determining whether or not the electrode array was inserted and/or is being inserted in a manner that results in a predetermined placement. By way of example only and not by way of limitation, the predetermined placement can be perimodiolar placement (sometimes referred to as a modiolous wall hugging placement), a mid scalla placement, and/or a lateral wall placement. In an exemplary embodiment, the placement can correspond to an insertion depth of the electrode array into the cochlea, etc.

In an exemplary embodiment of this method, the determining action is executed between temporal location 1 and temporal location 2 and/or after temporal location 2.

In some embodiments, the action of determining whether or not the electrode array was inserted and/or is being inserted in a manner that results in a predetermined placement is an action of determining that the electrode array is being inserted in a manner that will not result in a predetermined placement, and the action of determining is executed before temporal location 2 and/or after temporal location 2. In an exemplary embodiment, the patient is made without imaging, and/or is made based solely on the measurements obtained from the electrode array.

In an exemplary embodiment, the action of determining whether or not the electrode array was inserted and/or is being inserted in a manner that results in a predetermined placement is executed automatically by a surgical instrument, such as by way of example only and not by way of limitation, any of the devices and/or systems disclosed in Appendix A, B, C, D and/or E. in an exemplary embodiment, the surgical instrument provides an indication, such as an automatic indication, of the determination to a surgeon or other healthcare professional that the electrode array was or was not or is or is no being inserted in a manner that results in the predetermined placement.

It is noted that in at least some exemplary embodiments, the various determinations and/or analyses are executed in real time and/or in close temporal proximity to the insertion of the electrode array, such during insertion of the electrode array and/or within one, two, three, four, five, six, seven, eight, nine or ten minutes of full insertion. In an exemplary embodiment, the method can further include obtaining data indicative of a type of electrode array being inserted into the cochlea, wherein the action of analyzing the measured voltages during temporal location 1 and temporal location 2 includes comparing the measured voltages to predetermined values corresponding to what the voltage measurements should be for the type of electrode array.

It is noted that the following focuses on "type of array," but it is noted that embodiments instead and/or in addition to this can correspond to the type of insertion. That is, any disclosure herein of a type of array also corresponds to a disclosure of the type of insertion for that electrode array, and vice versa.

In an exemplary embodiment, there is a method detailed herein, wherein the method further includes obtaining data indicative of a type of electrode array and/o data indicative of the type of insertion that should be executed for the electrode array (modiolous, mid-scala or lateral wall) being inserted into the cochlea, wherein the action of analyzing the measured voltages during temporal location 1 and temporal location 2 includes evaluating the voltage measurements to determine a distance from a wall of a cochlea, and the action of determining whether or not the electrode array was inserted and/or is being inserted in a manner that results in the predetermined placement includes comparing the determined distance to that which should correspond to the type of electrode array. In an exemplary embodiment, there is the action of obtaining data indicative of a type of electrode array being inserted into the cochlea, wherein the action of determining whether or not the electrode array was inserted and/or is being inserted in a manner that results in a predetermined placement is executed automatically by a surgical instrument (e.g., any of those disclosed in any of the appendices), wherein the surgical instrument is configured to control a flow of current to various electrodes of the electrode array and to measure voltages at various electrodes of the electrode array according to a plurality of possible regimes (any of the current flow regimes and/or any of the measurement regimes disclosed in any of the appendices herein), and the method further comprises providing the surgical instrument with the data indicative of the type of electrode array (or type of insertion), using the surgical instrument, automatically applying between temporal location 1 and 2, a subset of the possible regimes (i.e., applying some but not all of the possible regimes to which the surgical instrument is configured to apply—note that this is not merely capable of applying, but constitutes a number of regimes that are programmed into the controller at that time were only some of the regimes are utilized), thereby measuring the voltage, wherein the surgical instrument determines the subset (automatically) to be applied based on the provided data indicative of the type of the electrode array. That said, in an exemplary embodiment, a healthcare professional determines the routine. In an exemplary embodiment, healthcare professional can input the type of insertion and/or the type of array into the surgical instrument, and the surgical instrument can identify various routines that will be utilized based on that input In an exemplary embodiment, the subset of the possible regimes is a subset of voltage measurements that reveal data related to the type of electrode array begin inserted (and/or the type of insertion), and the non-used regimes include measurements of voltages that that reveal data unrelated to, or at least less related to (relative to the data related to the type) the type of electrode array (and/or type of insertion) being inserted and related to other types of electrode arrays not being inserted. By way of example only and not by way of limitation, in an exemplary embodiment, data unrelated to or less related to a lateral wall array may include data indicative of a distance from the modiolous wall, and data unrelated to or less related to a modiolous array may include determining whether or not there is blood in the cochlea.

In an exemplary embodiment, the method includes obtaining data indicative of a type of electrode array being inserted into the cochlea, wherein the action of determining whether or not the electrode array was inserted and/or is being inserted in a manner that results in a predetermined placement is executed automatically by a surgical instrument, the surgical instrument is configured to analyze the voltage measurements according to a plurality of possible regimes, and the method further comprises providing the surgical instrument with the data indicative of the type of electrode array (or type of insertion) and using the surgical instrument, automatically applying between temporal location 1 and 2, a subset of the possible regimes, thereby analyzing the voltages, wherein the surgical instrument determines the subset to be applied based on the provided data indicative of the type of the electrode array.

In an exemplary embodiment, there is a system, such as any of the systems detailed in any of the appendices, as modified according to the following, where the system includes a cochlear implant sub-system including an electrode array and a control sub-system, wherein the system is configured to (i) operate electrodes of the electrode array as a source and a sink (and/or in accordance to any of the teachings in any of the appendices); (ii) operate electrodes of the electrode array as read electrodes (and/or in accordance with any of the teachings in any of the appendices); and (iii) enable communication between the control sub-system and the cochlear implant sub-system.

In an exemplary embodiment, the control sub-system is configured to analyze signals from the cochlear implant sub-system, and adapt at least one of an analysis routine or the operation of the electrodes of the electrode array based on the analysis. This as opposed to a system that operates the same way irrespective of the analysis of the signals and/or irrespective of the signals received from the electrode array.

In an exemplary embodiment of the systems detailed herein, the analysis routine includes selecting data to analyze relative to other data from read electrodes, and the action of adapting the analysis routine includes selecting the data to analyze instead of the other data. By way of example only and not by way of limitation, in an exemplary embodiment, data from some electrodes can be analyzed and data from other electrodes are not analyzed.

In an exemplary embodiment, the control sub-system is configured to analyze signals from the cochlear implant sub-system during a first temporal period and the control sub-system is configured to adapt at least one of the analysis routine or the operation of the electrodes based on the analysis during the first temporal period so that at least one of the analysis routine or the operation the electrodes is different during a second temporal period later than the first temporal period. In an exemplary embodiment, with respect to the operation of the electrodes, the magnitude of the current and/or the frequency is applied given electrodes can be varied. In an exemplary embodiment, the current can be applied to some electrodes and not applied to other electrodes, etc.

In an exemplary embodiment, the control sub-system is configured to analyze signals from the cochlear implant sub-system during a first temporal period and identify one or more possible position scenarios relating to the electrode array from a group of scenarios relating to the electrode array (any of the scenarios detailed in any of the appendices), and the control sub-system is configured to adapt at least one of the analysis routine or the operation of the electrodes based on the identified one or more possible position scenarios so that at least one of the analysis routine or the operation of the electrodes is different during a second temporal period later than the first temporal period (e.g., the first temporal period can be the initial insertion time of the electrode array, and the second temporal period can be a leader insertion time period of the electrode array), and the control sub-system is configured such that if one or more possible position scenarios was different from that identified, the control sub-system would adapt at least one of the analysis routine or the operation of the electrodes based on the identified one or more possible position scenarios in a different manner and there still would be a difference during the second temporal period relative to the first temporal period (that is, the adaption can be different for different position scenarios, and there would be adaption in these instances—the ideas that the system will adapt to focus on certain features at the expense of other features in view of the given scenario, whereas during the first period of time, other features are focused upon because the scenario is not known).

In an exemplary embodiment, the control sub-system is configured to analyze signals from the cochlear implant sub-system during a first temporal period and the control sub-system is configured, based on the analysis during the first temporal period, to adapt at least one of an analysis routine or the operation of the electrodes of the electrode array so as to focus an analysis of signals received during a second temporal period after the first time period on some aspects of cochlear implant electrode array insertion rather than other aspects of such (e.g., dislocation instead of blood, wall distance instead of fold over, —any of the aspects of appendices—etc.), wherein the first temporal period and the second temporal period both elapse during array insertion into the cochlea.

In an exemplary embodiment, the control sub-system is configured to execute one or more of the method actions respectively detailed in two or more of Appendix A, Appendix B, Appendix C, D, E or F, and the action of adapting results in the control-sub system executing one or more of the method actions detailed in Appendix A, B, C, D, E or F but at least not one other method action that the control sub-system is configured to execute (again, the sub-system could execute it—it is programmed/configured to do so, but it does not do so).

In an exemplary embodiment, the control sub-system is configured to execute one or more of the method actions respectively detailed in two or more of Appendix A, B, C, D, E or F, and the action of adapting results in the control-sub system executing one or more of the method actions detailed in Appendix A, B, C, D, E or F but no other method actions that the control sub-system is configured to execute.

It is noted that the control subsystem can be part of the cochlear implant, and in other embodiments, the control subsystem can be a separate component.

In an exemplary embodiment, the control sub-system is configured to analyze signals from the cochlear implant sub-system during a first temporal period, the control sub-system is configured to, based on the analysis during the first temporal period, to identify an electrode array insertion scenario from amongst a plurality of insertion scenarios, the control sub-system is configured to, based on the identified electrode array insertion scenario, adapt at least one of an analysis routine or the operation of the electrodes of the electrode array based on the identified scenario so that some analysis and/or operation of the electrodes is executed and other analysis and/or operation of the electrodes is not executed, wherein the control sub-system is configured to execute both the executed analysis/operation and the non-executed analysis operation. In an exemplary embodiment, the control sub-system is configured to condition data based on the received signals and use the conditioned data as part of the analysis of the signals.

In an exemplary embodiment, the control sub-system is configured to execute one or more of the method actions respectively detailed in two or more of Appendix A, Appendix B, Appendix C, D, E or F (and there is a method of executing one or more of the things it is configured to execute), and the action of adapting results in the control-sub system executing one or more of the method actions detailed in Appendix A, B, C, D, E or F but at least not one other method action that the control sub-system is configured to execute that the sub-system previously executed.

In an exemplary embodiment, there is a system, comprising a control unit configured to receive telemetry from an implantable system of a cochlear implant electrode array and analyze the telemetry (which can be any system disclosed in any of the appendices as modified accordingly) wherein the telemetry includes data based on electrical phenomenon associated with the electrode array, and the control unit is configured to execute one or more of the method actions respectively detailed in two or more of Appendix A, B, C, D, E or F. In an exemplary embodiment the system is configured to receive input from a healthcare professional that automatically enables the execution of the one or more of the method actions respectively detailed in two or more of Appendix A, B, C, D, E or F but at least not one other method action and/or no other method action that the control sub-system is configured to execute. In an exemplary embodiment, the system is configured to receive input that automatically enables the execution of the one or more of the method actions respectively detailed in two or more of Appendix A, B, C, D, E or F, but at least not one other method action and/or no other method action that the control sub-system is configured to execute.

The system can be configured to receive input that at least partially overrides the lack of enablement of at least one of the other method actions so that such is enabled. By way of example only and not by way of limitation, the system can be configured to receive input from a healthcare professional or the like such that the lack of enablement is overridden, and the method actions are again executed. Note also that in an exemplary embodiment, the system can be configured to automatically do this based on the collection of data that would indicate such has utilitarian value. By way of example only and not by way of limitation, in a scenario where some of the method actions are disabled, which disabling can be a result of, for example, an analysis of the data indicating that those method actions are not utilitarian, later data can indicate that the method actions would again be utilitarian, and thus the system would reenable those method actions.

In an exemplary embodiment, the system is configured to identify 2 or more, 3 or more, 4 more, 5 or more or all 6 of:
tip fold over;
scala dislocation;
distance from modiolus of the array;
phenomenon that exists in the recipient;
that the electrode array has reached a specific location in the cochlea; and
blood in the cochlea.

In an exemplary embodiment, the system is configured to perform at least 2 or more, or at least 3 or more or at least 4 more or at least 5 or more or at least 6 or more or at least 7 or more or at least 8 or more or at least 9 or more or all of the following:
determine a positional feature of the electrode array based on the vertical electrical sounding;
condition information in the received telemetry and perform the analysis based on the conditioned information;
determine, based on the telemetry, that a physical characteristic associated with the electrode array that is strictly local to the electrode array existed and/or exists;
determine spatial derivatives of electrical properties between electrodes of the electrode array;
identify changes between voltage measurements at read electrodes between different temporal locations;
detecting a voltage change across the plurality of electrodes based on a monitored relative magnitude that is representative of a voltage change at a reference electrode;
identify a presence of an asymmetry in the voltage measurements;
focus readings from read electrodes of the electrode array at a same location within the cochlea relative to other locations within the cochlea while the electrode array is moving;
interleave neural response measurements with impedance measurements between electrodes of the cochlear implant electrode array while the electrode array is being moved; and
determine a location, density and temporal feature of the impedance change.

In an exemplary embodiment, the system is configured to perform at least 2 or more, or at least 3 or more or at least 4 more or at least 5 or more or at least 6 or more or at least 7 or more or at least 8 or more or at least 9 or more or 10 or more or 11 or more or 12 or more or 13 or more or 14 or more or 15 or more or 16 or more or 17 or more or 18 or more or 19 or more or 20 or more or 21 or more or 22 or more or 23 or more or 24 more or 25 or more or 26 or more or 27 or more or 28 or more or 29 or more or 30 or more of any action or functionality disclosed in any of the appendices or throughout any of the appendices herein (all can come from one appendix, all can come from separate appendices, etc.)

In an exemplary embodiment, there is a method that includes executing at least 2 or more, or at least 3 or more or at least 4 more or at least 5 or more or at least 6 or more or at least 7 or more or at least 8 or more or at least 9 or more or 10 or more or 11 or more or 12 or more or 13 or more or 14 or more or 15 or more or 16 or more or 17 or more or 18 or more or 19 or more or 20 or more or 21 or more or 22 or more or 23 or more or 24 more or 25 or more or 26 or more or 27 or more or 28 or more or 29 or more or 30 or more of any action disclosed in any of the appendices or throughout any of the appendices herein (all can come from one appendix, all can come from separate appendices, etc.).

In view the above, it can be seen that in at least some exemplary embodiments, there are methods that include executing the method actions of the various appendices in a single method, such as during insertion of the electrode array or during the operation that is the insertion of the electrode array (the latter which would include after the electrode array is fully inserted, which would include the scenario where based on the measurements for the analysis of the measurements, the electrode array would have to be repositioned—fully inserted means that the surgeon has inserted the electrode array as far as he or she would insert the electrode array—scenarios exist where after full insertion, based on data, the surgeon may withdraw the electrode array a little bit—that would be after the electrode array is fully inserted, but still during the surgery). The idea is that in at least some exemplary embodiments, there is utility to executing some of the aspects of the difference appendices during the same method. For example, there can be utilitarian value with respect to analyzing data for blood in the cochlea as well as analyzing the data for dislocation as well as analyzing the data to determine that the electrode array should not be inserted any further and/or for determining the possibility that the electrode array is contacting the basilar membrane. It is also to be understood that in at least some exemplary embodiments, these methods actions can be executed during some parts of the operation and not others electrode array insertion process but not other parts based on data and/or the results of the analysis and/or based on statistically significant data, such as the likelihood that there will be trauma in the cochlea is reduced after the electrode array reaches a certain location within the cochlea, and thus it is less utilitarian to continue to attempt to identify such.

In view of the above, it can also be seen that there are systems and/or devices that are configured to execute various method actions of the appendices and/or have the functionality of the various devices and/or systems of the appendices, and that during a cochlear implant operation, such as during electrode array insertion, some functionalities will be used and some functionalities will not be used, depending on the circumstances, while other functionalities will be used and other functionalities will not be used depending on other circumstances.

Appendix F details various ECOG methods and various methods to determine whether or not the array is in contact with the basilar membrane. In this regard, embodiments include methods where, during insertion of the electrode array, one or more of the method actions detailed in appendix F is executed along with one or more of the method actions detailed in any of the other appendices. In this regard, in an exemplary embodiment, there is an exemplary method, comprising inserting a cochlear implant electrode array into a cochlea, and executing neural response measurements (e.g., those of Appendix F, or NRT using stimulation from the electrode array to evoke a neural response) and executing impedance measurements with the electrode array during the insertion (as opposed to after insertion). In an exemplary embodiment the action of executing the neural response measurements and the action of executing impedance measurements includes segregating the respective measurements into respective temporal periods. In this regard, in an exemplary embodiment, the impedance measurements, or, more specifically, the current generated by the electrodes for the impedance measurements, can interrupt the measurements for the ECOG and/or the NRT, and/or vice versa. In an exemplary embodiment, one can skew the other and/or the other can skew the one. Accordingly, in an exemplary embodiment, the neural response measurements and the impedance measurements are separated in a temporal manner so as to avoid any skewing that effectively skews the results.

In an exemplary embodiment, there is a method that includes the action of determining an insertion location of the electrode array and adjusting a timing of neural response measurements and/or impedance measurements based on the location of the electrode array. In this regard, in an exemplary embodiment, there can be utilitarian value with respect to executing one or more of the method actions associated with appendices A-E when the electrode array is not proximate the stop zone detailed in Appendix F. Thus, if the electrode array is not proximate the stop zone, the neural response measurements may not be taken in some embodiments, or in other embodiments, the neural response measurements will not be taken as frequently relative to that which would be the case if the electrode array was proximate/approaching the stop zone. Conversely, in an exemplary embodiment, there can be utilitarian value with respect to executing one or more of the method actions associated with appendix F when the electrode array is approaching the stop zone, at least in a manner that is temporally more frequent relative to that which is the case when the electrode array is further away from the stop zone. In this regard, the impedance measurements may be taken less frequently relative to that which is the case when the electrode array is away from the stop zone. Is also noted that in an exemplary embodiment, such as where the tip of the electrode array is approaching the basal turn, in exemplary embodiment, the impedance measurements may be taken more frequently than at other locations and/or the neural response measurements may be taken at a frequency less than that which would be the case at the other locations.

In view of the above, it can be seen that in at least some exemplary embodiments, the methods include actively managing the different types of measurements so as to optimize or otherwise focus on obtaining certain information relative to obtaining other information based on the conditions associated with the electrode array at a given time.

In an exemplary embodiment, the action of executing the neural response measurements and the action of executing impedance measurements includes executing such in respective temporal periods that do not overlap. In an exemplary embodiment, the action of executing the neural response measurements and the action of executing impedance measurements includes executing such in respective temporal periods that are temporally separated by periods of no measurements. These periods can be based on a given time period and/or can be based on a number of electrodes inserted into the cochlea since the last action and/or the distance that the electrode array has been inserted since the last action, etc.

In an exemplary embodiment, there is the action of determining an insertion location of the electrode array, and concentrating the execution of the neural response measurements over the impedance measurements and vis-a-versa based on the location of the electrode array. In an exemplary embodiment, there is a method that includes determining an insertion location of the electrode array and at least one of:

increasing a temporal average execution of the neural response measurements and decreasing a temporal average execution impedance measurements based on the location of the electrode array; or decreasing a temporal average execution of the neural response measurements and increasing a temporal average execution impedance measurements based on the location of the electrode array.

In an exemplary embodiment, there is a method as detailed herein further comprising an action of determining an insertion location of the electrode array, and concentrating the execution of the neural response measurements over the impedance and executing the neural response measurements and/or not executing the impedance measurements while the electrode array is being extended into a third portion of the cochlea beyond the first portion.

In an exemplary embodiment, there is the action of determining an insertion location of the electrode array, and concentrating the execution of the neural response measurements over the impedance measurements and vis-a-versa based on the location of the electrode array. In an exemplary embodiment, there is a method as detailed herein further comprising:

determining an insertion location of the electrode array;

executing the neural response measurements and/or not executing the impedance measurements while the electrode array is being extended into a first portion of the cochlea; and halting the neural response measurements and/or executing the impedance measurements while the electrode array is being extended into a second portion of the cochlea further into the cochlea than the first portion.

In an exemplary embodiment, the method(s) further include:

determining an insertion location of the electrode array;

executing the neural response measurements a first number of times within a first temporal period while the electrode array is being extended into a first portion of the cochlea such that there is an average per second of measurements for the first period; and executing the neural response measurements a second number of times within a second temporal period while the electrode array is being extended into a second portion of the cochlea further into the cochlea than the first portion such that there is an average per second of measurements for the second period, wherein the average for the first period is greater than or less than the average for the second period.

In an exemplary embodiment, the method(s) further include:

determining an insertion location of the electrode array;

determining an insertion location of the electrode array;

executing the impedance measurements a first number of times within a first temporal period while the electrode array is being extended into a first portion of the cochlea such that there is an average per second of measurements for the first period;

executing the impedance measurements a second number of times within a second temporal period while the electrode array is being extended into a second portion of the cochlea further into the cochlea than the first portion such that there is an average per second of measurements for the second period, wherein the average for the first period is greater than or less than the average for the second period.

In an exemplary embodiment, the method(s) further include:

determining an insertion location of the electrode array;

determining that the array is a modilous array or non-modiolous array;

determining an insertion location of the electrode array; and adjusting a timing of neural response measurements and/or impedance measurements based on the location of the electrode array and based on the determined type of array.

In an exemplary embodiment, the method(s) further include:

determining an insertion location of the electrode array;

determining that the array is a modilous array or non-modiolous array;

determining an insertion location of the electrode array; and concentrating the execution of the neural response measurements over the impedance measurements and vis-a-versa based on the location of the electrode array and based on the determined type of the array.

In an exemplary embodiment, the method(s) further include:

determining an insertion location of the electrode array;

determining that the array is a modilous array or non-modiolous array;

determining an insertion location of the electrode array; and concentrating the execution of the neural response measurements over the impedance measurements and vis-a-versa based on the location of the electrode array and based on the determined type of the array.

In an exemplary embodiment, there is an exemplary method, comprising inserting a cochlear implant electrode array into a cochlea, and executing neural response measurements (e.g., those of Appendix F, or NRT using stimulation from the electrode array to evoke a neural response) and executing impedance measurements with the electrode array prior to full insertion into the cochlea.

In an exemplary embodiment, the neural response measurements are acoustically-evoked inner ear potential measurements.

In an exemplary embodiment, the methods detailed herein further comprise determining a location of the electrode array based on the acoustically-evoked inner ear potentials and determining a spatial property of the electrode array, such as location, based on the impedance measurements. In an exemplary embodiment, the neural response measurements are acoustically-evoked inner ear potential measurements, and the method(s) further comprise evaluating the measurements for an array insertion stop condition while inserting the array based on the acoustically-evoked inner ear potential, and evaluating the measurements for an array insertion stop condition while inserting the array based on based on the impedance measurements.

In an exemplary embodiment, the neural response measurements are acoustically-evoked inner ear potential measurements, and the method further comprises evaluating the measurements for an array insertion stop condition while inserting the array based on the acoustically-evoked inner ear potentials and evaluating the measurements for any one or more of an array condition detailed in Appendix A, B, C, D, E or F.

In an exemplary embodiment, method as detailed herein can include the action of repeatedly determining locations of the electrode array during insertion as the electrode array is advanced into the cochlea and switching from neural response measurements to impedance measurements and/or vis-a-versa based on the determined locations. In some embodiments, the methods include repeatedly determining locations of the electrode array during insertion as the electrode array is advanced into the cochlea and switching from neural response measurements to impedance measurements and/or vis-a-versa based on the determined locations. In an exemplary embodiment, the methods include repeatedly determining locations of the electrode array during insertion as the electrode array is advanced into the cochlea, relying on the neural response measurements to identify a location of the electrode array and/or to halt an insertion of the electrode array based on a feature of the cochlea that exists only in the presence of stimulus that evokes the neural response and/or based on the electrode array contacting the basilar membrane, relying on the impedance measurements to identify a location of the electrode array and/or to halt an insertion of the electrode and/or identify a spatial feature of the array based on a feature of the cochlea that exists irrespective of the presence or absence of the stimulus that evokes the neural response.

In an exemplary embodiment, the methods can include repeatedly determining locations of the electrode array during insertion as the electrode array is advanced into the cochlea, applying the impedance measurements while limiting or suspending the neural response measurements when an apical tip of the array is determined to be at the basil turn or proximate an anatomical structure in the cochlea present in a statistically significant percentage of humans; and applying the neural response measurements while limiting or suspending the impedance measurements when the apical tip of the array is determined to be away from the basil turn or away from the anatomical structure.

In an exemplary embodiment, the methods can include identifying, during insertion, that a situation of interest related to the electrode array exists, which did not exist prior to the insertion, determining that the situation of interest is based on measurements from the neural response measurements or the impedance measurements and/or determining that the situation of interest can be better analyzed by the neural response measurements or the impedance measurements, and limiting measurements for a first period of time after the determination(s) to one of neural response measurements or impedance measurements based on the determination(s).

In an exemplary embodiment, the methods can include identifying, during insertion, that the situation of interest no longer exists and/or a second situation of interest related to the electrode array exists, which did not exist prior to the insertion, second determining that the second situation of interest, if present, is based on measurements from the neural response measurements or the impedance measurements and/or second determining that the situation of interest can be better analyzed by the neural response measurements or the impedance measurements and/or determining that in the absence of the situation of interest, it is less useful than was the case during the first period of time to limit the measurements, and that for a second period of time after the second determination(s), lifting the limitation.

In an exemplary embodiment, there is a method that includes executing real time measurements of voltages at electrodes of an electrode array as the electrode array is moving within a cochlea during insertion of the electrode array therein, analyzing during insertion, some but not all of the measurements to identify one or more first occurrences from a group of first occurrences, and analyzing after insertion, at least some of the measurements not analyzed during the insertion to identify one or more second occurrences from a group of second occurrences.

In an exemplary embodiment of this exemplary method, this method can have utilitarian value with respect to limiting the analysis to things that are more important or otherwise critical during the insertion phase, which can be accomplished within 15, 20, 25, 30 seconds, 45 seconds, 60, 75, 90, 100, 120, 130, 140, 150, 180 seconds, or within 4 or 5 or 6 or 7 or 8 or 9 or 10 minutes (e.g., for initial entry to the cochlea to full insertion), depending on the embodiment. Thus, processing power of the surgical instruments/systems/ devices can be concentrated, during insertion, on the areas where immediate feedback/real-time feedback will provide or otherwise can provide utilitarian instruction to the surgeon or other healthcare professional during the insertion process, thus increasing the likelihood that the resulting analysis or otherwise resulting data captured is utilitarian to the surgeon or healthcare professional because the system is not bogged down or otherwise addressing other areas that are not of a concern. After this, secondary analyses are executed one the data when there is more time to execute these analyses. It is noted that this embodiment of this method can be applicable to a scenario where analyses require more processing power or otherwise analyses where in-depth analysis is executed during the insertion process occurs (so as to get specific results/accurate results that are critical or otherwise utilitarian to evaluating the insertion process), at the expense of other analyses, as well as scenarios where there is only so much data that can be processed at any one time, even under a streamlined processing scenario, as well as scenarios where the analysis can be executed during the insertion process, but the feedback would result in overload to the surgeon or other healthcare professional.

It is also noted that another variation of this method could be such that processing power of the surgical instruments/ systems/devices and/or the focus of measurements at some electrodes but not others and/or focus of current supply to some electrodes but not others can be concentrated, during insertion, on the areas where immediate feedback/real-time feedback will provide or otherwise can provide utilitarian instruction to the surgeon or other healthcare professional during the insertion process, thus increasing the likelihood that the resulting analysis or otherwise resulting data captured is utilitarian to the surgeon or healthcare professional because the system is not bogged down or otherwise addressing other areas that are not of a concern.

In an exemplary embodiment of the above method, the first group and the second group of occurrences overlap one another, and the second group has more occurrences than the first group. It is briefly noted that the occurrences can be occurrences related to the electrode array, such as electrode array tip fold over, electrode array scala puncture, etc. is also noted that the occurrences can be occurrences related to phenomenon inside the cochlea, such as blood in the cochlea. In an exemplary embodiment, the occurrence can be the scenario where the electrode array approaches or otherwise is located within a certain distance of a wall of the cochlea. In an exemplary embodiment, the occurrence can be the approach meant of the electrode array to a physical feature of the cochlea, such as a construction. An occurrence can correspond to any of the occurrences in appendix A, B, C, D, E or F. in some embodiments, an occurrence can correspond to any of the features or things that are identified or otherwise result from the analysis of any of the analysis executed in any of the appendices A, B, C, D, E or F.

In an exemplary embodiment, the action of analyzing after insertion includes a verification of an insertion of the electrode array into to the cochlea. In an exemplary embodiment, the action of analyzing during insertion is a triage exercise relative to the analyzing after insertion.

In an exemplary embodiment, there is an extra action of taking additional measurements after full insertion of the electrode array into the cochlea, wherein the action of analyzing after insertion, at least some of the measurements not analyzed during the insertion to identify one or more second occurrences from a group of second occurrences includes analyzing at least some of the measurements taken after full insertion. Again, this is consistent with the embodiment detailed above where electric current and/or measurements are limited to certain electrodes and not applied to others on purpose so as to if you will, conserve resources during the insertion process and otherwise focus the measurements at areas where there is more utilitarian value during insertion. After the full insertion, when the electrode is stationary, and thus there is more time, a larger battery of tests are executed, and, by way of example, a larger number of measurements applied to a larger number of electrodes can be applied and/or a larger number of currents can be applied to a larger number of electrodes.

In an exemplary embodiment, the action of analyzing during insertion is executed to at least in part identify a potential of damage to the array or to the cochlea that is statistically more likely to cause damage to the cochlea relative to other insertion scenarios, and the action of analyzing after insertion is executed to at least in part evaluate placement of the electrode array for long term usage. In an exemplary embodiment, the action of analyzing during insertion is executed to at least in part identify an insertion stop condition, and the action of analyzing after insertion is executed to at least in part evaluate placement of the electrode array for long term usage.

In an exemplary embodiment, there is a system, comprising a cochlear implant sub-system including an electrode array, and a control sub-system, wherein the system is configured to:
  operate electrodes of the electrode array as a source and a sink;
  operate electrodes of the electrode array as read electrodes; and
  enable communication between the control sub-system and the cochlear implant sub-system.

In an exemplary embodiment, of this system, the control sub-system is configured to:
  obtaining data indicative of a type of electrode array being inserted into the cochlea (and/or the type of insertion);
  execute two or more analysis regimes to analyze the signals from the cochlear implant sub-system;
  implement one or more analysis regimes of the two or more analysis regimes to analyses the signals from the cochlear implant sub-system as opposed to one or more other analysis regimes of the analysis regimes based on the data indicative of a type of electrode array (and/or type of insertion); and
  analyze signals from the cochlear implant sub-system based on the implemented analysis regime.

In an exemplary embodiment, the analysis regimes can be any of those in Appendix A, B, C, D, E or F. In an exemplary embodiment, the system identifies the pertinent analysis regime(s) for the given type and apply such as opposed to applying all possible analysis regimes for which the system is programmed and/or as opposed to applying analysis regimes that are applicable or more applicable to other types.

In an exemplary embodiment, a first regime analyzes the signals for data indicative of blood in the cochlea, a second regime analyzes the signals for data indicative of tip fold over, and the system is configured to automatically use the first regime and not use the second regime if the input indicative of the type of electrode array indicates that the type is a non-perimodiolar array, and the system is configured to automatically use the second regime and not use the first regime if the input indicative of the type of electrode array indicates that the type is a perimodiolar array. In an exemplary embodiment, a first regime analyzes the signals for data indicative of blood in the cochlea, a second regime analyzes the signals for data indicative of tip fold over, the system is configured to automatically use the first regime and not use the second regime if the input indicative of the type of electrode array indicates that the type is a lateral wall array and/or a mid-scala array, and the system is configured to automatically use the second regime and not use the first regime if the input indicative of the type of electrode array indicates that the type is a non-lateral wall array and/or a non-mid-scala array.

In an exemplary embodiment, a first regime analyzes the signals for data indicative of a sub-optimal insertion for a first type of array, a second regime analyzes the signals for data indicative of a sub-optimal insertion for a second type of array different from the first type of array, and the system is configured to automatically use the first regime and not use the second regime if the input indicative of the type of electrode array indicates that the type is the first type, and the system is configured to automatically use the second regime and not use the first regime if the input indicative of the type of electrode array indicates that the type is a second type.

In an exemplary embodiment, there is a first regime that analyzes the signals for data indicative of a distance of the array from a wall of the cochlea, there is a a second regime analyzes the signals for data indicative of scala dislocation. The system is configured to obtain information indicative of a depth of the electrode array during insertion of the electrode array into the cochlea and determine that the electrode array is fully inserted into the cochlea based on the obtained depth information, and the system is configured to automatically use the second regime if the input indicative of the type of electrode array indicates that the type is a non-perimodiolar array until a determination is made that the electrode array is inserted a certain depth into the cochlea and then automatically use the first regime or another regime (and in some embodiment, stop using the second regime), and the system is configure to automatically not use the first regime if the input indicative of the type of electrode array indicates that the type is a perimodiolar array until a determination is made that the electrode array is fully inserted into the cochlea and then automatically use the first regime.

In an exemplary embodiment, the system is configured to automatically switch between implemented analysis regimes based on input indicative of a depth of insertion of the electrode array. In an exemplary embodiment, the system is configured to automatically switch between implemented analysis regimes based on the analysis of the signals.

In an exemplary embodiment, some regimes are focused on identifying a buckling electrode. In this regard, in an exemplary embodiment, there is a regime that seeks to identify such, such as those described in appendix B, and this regime is implemented with respect to a perimodiolar array insertion. In an exemplary embodiment, some regimes are focused on determining a location where there remains to be residual hearing. In an exemplary embodiment, a regime can correspond to such, such as implementing an ECOG measurement, and in an exemplary embodiment, if the type is a lateral wall array insertion and/or a mid-scala insertion, the system will implement ECOG measurements, and may not do so if the array insertion is a perimodiolar insertion. Note also that in some instances, preoperative imaging may be executed in some instances but not others, depending on the type of array. In an exemplary embodiment, the regime can attempt to identify dislocation and/or basilar membrane contact, and this regime can be implemented in the case of a lateral wall array and/or a mid-scala array, but not in the case of a perimodiolar insertion. In some embodiments, the regime can be a basilar membrane contact regime, and this regime can be implemented in all instances.

In an exemplary embodiment, the systems can identify whether or not the electrode array is being inserted too quickly, can identify a trajectory of the insertion of the electrode array, and/or whether or not the electrode array is hitting something, and/or whether or not there is blood present in the cochlea. In some embodiments, any one or more of these can be implemented. In an exemplary embodiment, the system can be configured to identify the occurrence of any of these scenarios (or identify the trajectory), and based on empirical and/or statistical data, determine whether or not the insertion of the electrode array could be problematic, and provide a warning or otherwise provide an indication to the surgeon or other healthcare professional. In an exemplary embodiment, the analysis can include an evaluation between the data known for a given electrode array type and/or insertion type, and take this into account with respect to the evaluation of the data. Indeed, in an exemplary embodiment, such can reduce the likelihood of so-called false positives. By way of example, an indication that there exists blood in the cochlea might be discounted if the electrode array as a perimodiolar array. An indication that there has been dislocation might be discounted if the electrode array as a lateral wall array.

In an exemplary embodiment, the systems can identify a bad insertion based on the speed of which the electrode array is being inserted (e.g., too quickly), a trajectory of the insertion of the electrode array (also more easily if the type of array is known/type of insertion), if the electrode array is hitting something, and/or if there is blood present in the cochlea.

In an exemplary embodiment, systems and/or methods disclosed herein may be such that the following is more of a focus than other phenomenon: tip fold over (during early or mid-part of the insertion, at least and/or as the array approaches the basal turn), blood (when the tip of the array is about the middle part or the electrode 8, 9, 10, or 11 final position (relative to the cochlea after final insertion) dislocation, basilar membrane (for lateral wall, but for mid to later part of the insertion), increase in the ECOG voltage/plateau, etc. in this regard, the aforementioned phenomenon are things that can be a focus on during insertion, at least at the times and or situations identified, more so than other phenomenon. In an exemplary embodiment, the devices and/or systems in our methods limit themselves to looking at only one or more of these phenomenon, at least during the times indicated.

In an exemplary embodiment, there is the action of determining positional feature of the electrode array based on the vertical electrical sounding. In an exemplary embodiment, this is executed for a perimodiolar array, and in some instances, only after insertion, and can be executed for a lateral wall but only sometimes/limited times during insertion, to make sure the array is not twisted. In an exemplary embodiment, the conditioning of information in the received telemetry and perform the analysis based on the conditioned information; determine, based on the telemetry, that a physical characteristic associated with the electrode array that is strictly local to the electrode array existed and/or exists is executed for all types of arrays and/or for all types of insertions. Also, for all arrays, the determination of spatial derivatives of electrical properties between electrodes of the electrode array. For all arrays, but more so for lateral wall, t teachings detailed herein are executed to identify changes between voltage measurements at read electrodes between different temporal locations. In some embodiments, there is the action of detecting a voltage change across the plurality of electrodes based on a monitored relative magnitude that is representative of a voltage change at a reference electrode, for all arrays. Also, in some embodiments, for all arrays, there is the action of identifying a presence of an asymmetry in the voltage measurements.

Some embodiments limit the focusing of readings from read electrodes of the electrode array at a same location within the cochlea relative to other locations within the cochlea while the electrode array is moving to lateral wall arrays.

Some embodiments utilize, for all arrays, the interleaving of neural response measurements with impedance measurements between electrodes of the cochlear implant electrode array while the electrode array is being moved. That said, in some embodiments, this is limited to only the lateral wall arrays.

In some embodiments, there is a determination at a location of density and temporal features of the impedance changes but only for lateral wall arrays. In some embodiments, tip fold over analysis is executed only for perimodiolar arrays.

In some embodiments, scala dislocation is executed only for lateral wall arrays. In some embodiments, the distance from the modiolous of the array is executed only for perimodiolar arrays, while in other embodiments, it is executed for all types of arrays and/or for perimodiolar and or mid scala arrays. Evaluations of data to identify phenomenon that exists in the recipient are executed for all arrays in some embodiments. Also, evaluations that indicate that the electrode array has reached a specific location in the cochlea are executed for all arrays in at least some exemplary embodiments. Conversely, evaluations of whether or not there exists blood in the cochlea can be executed in a manner limited only to lateral wall and/or midscale arrays.

It is noted that the above examples are just that: examples embodiments include methods and/or systems and/or devices where various analyses and/or phenomenon to be detected and/or types of measurements are limited to insertions of one type of electrode arrays were two types of electrode arrays but not all three types of electrode arrays. Accordingly, embodiments include disclosures in any of the appendices herein that are limited to only one type of electrode array versus other types of electrode arrays/types of insertions (e.g., limited to perimodiolar, perimodiolar and mid scala, mid-scala, mid-scala and lateral wall, or lateral wall). Thus, the methods can be so limited and/or the systems and/or devices can be so limited such that the systems and/or devices do not execute a given analysis and/or a given action and/or a given functionality even though such a program to to do so or otherwise configured to do so because of the type of insertion and/or the type of electrode array.

In an exemplary embodiment, the teachings detailed herein (where anytime that phrase is used herein, such includes everything, including the appendices) are utilized for diagnostic feedback based on the Electrode Specific Guidance—known trajectory combined with other metrics which strengthen the evidence for a diagnosis. By way of example, in a scenario whether is an identification of tip-foldover, the wide bipolar VT measure flags a possible tip-foldover. Conversely, the profile and evolution of the modiolar distance measure of the entire array does not match the expected behavior. Thus, the indication of a tip fold over can be discounted in some embodiments, and thus there is a method of doing so based on the aforementioned scenario Also by way of example, in a scenario where the ECoG plummets during the insertion of the array, and where the modiolar distance measure indicates the apical electrode is hugging the modiolus however the mid-array electrodes are bowing outwards. This would then suggest the contact with the basilar membrane is at the mid-array not the apical electrode, and thus there is a method for determining rather wise deciding that the contact with the basilar membrane is at the mid-array.

Consistent with Appendix E, it is noted that in an exemplary embodiment includes a method of inserting an electrode array into a cochlea and while the electrode array is being pushed into the cochlea, a tone or sound or otherwise acoustic stimulation is applied as part of an ECoG method. This sound can be continuous or semicontinuous during the insertion process. In an exemplary embodiment, the sound is used to stimulate the tissue and evoke the neural response for the amount of time that is at least 10, 15, 20, 25, 30, 35, 40, 45, 50, 55, 60, 65, 70, 75, 80, 85, 90, 95 or 100% of the time between the first electrode entering the cochlea until the last electrode enters the cochlea and/or the electrode array is fully inserted into the cochlea/until the electrode array reaches a location that corresponds to the furthest the electrode array is ever inserted into the cochlea. In an exemplary embodiment, the impedance measurements are taken while the aforementioned sound is stimulating the tissue/evoking the neural responses. In an exemplary embodiment, the ECoG measurements are taken while the aforementioned sound the stimulating the tissue/evoking mineral responses. Again, in an exemplary embodiment, the method of inserting the electrode array into the cochlea is executed while the sound is being played and otherwise evoking the neural responses, and during this time, the electrodes are being used to take the impedance measurements and/or the ECoG measurements. Accordingly, in an exemplary embodiment, there is a method that includes executing a portion of an ECoG method in general, and specifically, executing the acoustic stimulus to evoke the neural response, and while this neural response is occurring, taking the impedance measurements to execute one or more or all of the actions associated with the impedance measurements detailed herein (again, which includes any of the disclosures of Appendix A, B, C, D, E or F).

It is briefly noted that any disclosure herein of the taking of impedance measurements also corresponds to a disclosure of an embodiment of utilizing those impedance measurements according to any of the teachings detailed herein, providing that the art enables such.

In view of the above, an exemplary embodiment includes a method where, while the sound is applied, the ECOG measurements are interleaved with the impedance measurements.

Note also that while in some embodiments, the sound is constantly played, in other embodiments, the sound is played for only those portions of the insertion where it is more likely than not that the ECOG measurements will be utilitarian. For example, the sound could be begun to be played at a location somewhere before the do not exceed location such that there is very little likelihood that the electrode array will reach that location while the sound is not played. This will results, in some embodiments, to the sound being played during times where the ECOG measurements are not needed or otherwise less valuable than at other areas.

In an exemplary embodiment, the methods herein and the systems herein are such that the electrodes that are energized for the impedance measurements are not used as measurement electrodes for the ECOG measurements. In an exemplary embodiment, an exemplary method includes executing both ECOG measurements and impedance measurements during insertion, where the most distal electrode is not used as a source or sink. In an exemplary embodiment, an exemplary method includes executing both ECOG measurements and impedance measurements during insertion of the electrode array, where the second and or third and/or fourth most distal electrodes are never utilized as a source and/or a sink electrode. In an exemplary embodiment of this embodiment, the most distal electrode is used as a source and/or a sink.

An exemplary embodiment includes utilizing electrodes that are utilized as a source and/or a sink during impedance measurements as measurement electrodes for the ECOG measurements, except that the time period between the utilization of such as a source and/or a sink and the utilization as a measurement electrode is such that any polarization or otherwise charge buildup is reduced relative to that which would be the case if the electrodes were used as a source and a sink and a measurement electrode in a shorter time period.

Any disclosure of any method action detailed herein corresponds to a disclosure of a device and/or a system for executing that method action. Any disclosure of any method of making an apparatus detailed herein corresponds to a resulting apparatus made by that method. Any functionality of any apparatus detailed herein corresponds to a method having a method action associated with that functionality. Any disclosure of any apparatus and/or system detailed herein corresponds to a method of utilizing that apparatus and/or system. Any feature of any embodiment detailed herein (again, which includes the above and the appendices) can be combined with any other feature of any other embodiment detailed herein providing that the art enables such, unless such is otherwise noted. Any embodiment or teaching disclosed herein can be explicitly excluded in some embodiments, providing that the art enables such unless otherwise noted. Any embodiment detailed herein can be explicitly excluded from combination with any feature of any other embodiment detailed herein providing that the art enables such, unless such is otherwise noted.

Embodiments include one or more of the teachings of Appendix A, B, C, D, E and/or F. It is noted that some embodiments are such that any reference to Appendix B herein includes a reference to Appendix as an alternative, unless otherwise noted.

While various embodiments of the present invention have been described above, it should be understood that they have been presented by way of example only, and not limitation. It will be apparent to persons skilled in the relevant art that various changes in form and detail can be made therein without departing from the scope of the invention.

What is claimed is:

1. A method, comprising:
obtaining first data by:
operating a first set of electrodes as a source and sink in and/or on a mammal while operating a second set of electrodes as recorder electrodes in and/or on a mammal thereby obtaining first electrical data from the second set of electrodes;

obtaining second data by:
operating a third set of electrodes as a source and sink in and/or on the mammal, the third set being different than the first set and including two electrodes that are further from each other than respective electrodes of the first set, while operating the second set of electrodes as recorder electrodes in and/or on a mammal and thereby obtaining second electrical data from the second set of electrodes;

evaluating data by identifying an electrical property of the second data that is substantially deviant from that of the first data and/or other data relating to other set(s) of electrodes having distances of respective electrodes closer than that of the two electrodes of the third set, and based at least in part on a distance of electrodes of the third set determined based on the evaluation of the data, determining spatial positioning data of the electrodes of the second set.

2. The method of claim 1, wherein:
the first electrical data is a first impedance based data between the electrodes of the second set;
the second electrical data is a second impedance based data between the electrodes of the second set.

3. The method of claim 1, wherein:
the recorder electrodes are part of a cochlear electrode array that is located in a cochlea; and
the determined spatial positioning data is distance data of the recorder electrodes from a modiolus wall of the cochlea.

4. The method of claim 1, wherein:
the recorder electrodes are part of a cochlear electrode array that is located in a cochlea; and
the determined spatial positioning data is an orientation of the recorder electrodes relative to structure of the cochlea.

5. The method of claim 1, wherein:
the recorder electrodes are part of a cochlear electrode array that is located in a cochlea; and
the method further comprises evaluating the determined spatial positioning data to determine that an electrode array fixation failure has occurred.

6. The method of claim 1, wherein:
the recorder electrodes are part of a cochlear electrode array that is located in a cochlea;
the method further comprises determining based on the longitudinal location of the electrode array within the cochlea that an electrode array migration has occurred.

7. The method of claim 1, further comprising:
obtaining third data by:
operating a fourth set of electrodes as a source and sink in and/or on the mammal, while operating the second set of electrodes as recorder electrodes in and/or on the mammal, thereby obtaining third electrical data from the second set of electrodes, wherein
the action of evaluating data includes evaluating the third electrical data while also evaluating the second electrical data and the first electrical data, the electrodes of the first set are located closer to one another than the electrodes of the third set and between electrodes of the third set, and the electrodes of the third set are located closer to one another than the electrodes of the fourth set and between electrodes of the fourth set and the first set, the third set and the fourth set are sequentially operated in that order and the respective electrodes of the first set, the second set, the third set and the fourth set are all different from each other and the electrodes of the second set are between the electrodes of the first set.

8. The method of claim 1, wherein:
at least one of the electrodes of the first set of the electrodes is located in a cochlea, the electrodes are part of a cochlear implant, and collectively six electrodes make up the total of a group comprising the first set, second set and third set.

9. A method, comprising:
obtaining first data by:
operating a first set of electrodes as a source and sink in and/or on a mammal while operating a second set of electrodes as recorder electrodes in and/or on a mammal thereby obtaining first electrical data from the second set of electrodes;

obtaining second data by:
operating a third set of electrodes as a source and sink in and/or on the mammal, the third set being different than the first set, while operating the second set of electrodes as recorder electrodes in and/or on a mammal and thereby obtaining second electrical data from the second set of electrodes;

evaluating data by evaluating the first electrical data and the second electrical data; and determining spatial positioning data based on the evaluation of the data, wherein
respective first electrodes of the first and third sets are selected from a first group of electrodes,
respective second electrodes of the first and third sets are selected from a second group of electrodes, and
at least one of:
the electrodes of the second set are disposed between the respective first and second electrodes;
the electrodes of the second set are all disposed on one side of the electrodes of the first set;
the electrodes of the second set are closer together than a closest distance of electrodes of the first set; or
the electrodes of the first set are unevenly arrayed relative to the electrodes of the second set.

10. The method of claim 9, further comprising obtaining third data by:
operating a fourth set of electrodes as a source and sink in and/or on the mammal, the fourth set different than the third set, while operating a fifth set of electrodes as recorder electrodes in and/or on the mammal, thereby obtaining third electrical data from the second set of electrodes, obtaining fourth data by:
operating a sixth set of electrodes as a source and sink in and/or on the mammal, the sixth set different than the fourth set, while operating the fifth set of electrodes as recorder electrodes in and/or on the mammal, thereby obtaining fourth electrical data from the fifth set of electrodes, wherein
the action of evaluating data includes also evaluating the third electrical data and the fourth electrical data,
the electrodes of the sets of the electrodes are part of a cochlear electrode array that is located in a cochlea, and
the action of determining spatial positioning data based on the evaluation of the data includes determining a distance of the electrodes of the second set from a modiolus wall of the cochlea based on the evaluation of the second and first electrical data and determining a distance of the electrodes of the fifth set from a modiolus wall of the cochlea based on the evaluation of the third electrical data and the fourth electrical data.

11. The method of claim 10, further comprising:
obtaining distance data of a seventh set of electrodes used as recording electrodes from the modiolus wall, the seventh set being different than the second set and the fifth set; and
determining that the electrode array is at least one of over inserted into the cochlea, experienced a tip fold over, or is angularly misaligned by comparing the distance data of at least two of the seventh set, fifth set and second set to one another.

12. The method of claim 9, wherein:
all of the electrodes of the first set, second set and third set are part of a cochlear electrode array that is located in a cochlea.

13. The method of claim 9, wherein the method further comprises
determining, based on the determined spatial position data, that one or more of the following has occurred:
(i) a longitudinally local lateral angular position of the electrode array has shifted relative to another longitudinally local position;
(ii) the electrode array has been over inserted into a cochlea of the recipient;
(iii) the electrode array has become unfixed subsequent to full implantation into the recipient; or
(iv) the electrode array has migrated during implantation.

14. The method of claim 9, wherein:
the first electrical data is a first impedance based data between the electrodes of the second set;
the second electrical data is a second impedance based data between the electrodes of the second set, the second impedance data being spiked relative to the first impedance data;
the action of evaluating the first electrical data and the second electrical data includes comparing the first electrical data to the second electrical data and identifying the spike; and
the spike is caused by a substantially larger amount of current flowing between the electrodes of the third set flowing through bone of the cochlea than the amount of current flowing between the electrodes of the first set flowing through bone of the cochlea.

15. The method of claim 9, wherein:
the electrodes of the second set are disposed between the respective first and second electrodes.

16. The method of claim 9, wherein:
the electrodes of the second set are all disposed on one side of the electrodes of the first set.

17. The method of claim 9, wherein:
the electrodes of the second set are closer together than a closest distance of electrodes of the first set.

18. The method of claim 9, wherein:
the electrodes of the first set are unevenly arrayed relative to the electrodes of the second set.

19. A method, comprising:
obtaining first data by:
operating a first set of electrodes as a source and sink in and/or on a mammal while operating a second set of electrodes as recorder electrodes in and/or on a mammal thereby obtaining first electrical data from the second set of electrodes;
obtaining second data by:
operating a third set of electrodes as a source and sink in and/or on the mammal, the third set being different than the first set, while operating the second set of electrodes as recorder electrodes in and/or on a mammal and thereby obtaining second electrical data from the second set of electrodes;
evaluating data by evaluating the first electrical data and the second electrical data; and
determining spatial positioning data based on the evaluation of the data, wherein
the recorder electrodes are part of a cochlear electrode array that is located in a cochlea; and
the method further comprises evaluating the determined spatial positioning data and determining that at least one of the electrode array has punctured through a wall of the cochlea or that over insertion of the electrode array into the cochlea has occurred based on the determined spatial positioning data.

20. The method of claim 19, further comprising:
obtaining third data by:
operating a fourth set of electrodes as a source and sink in and/or on the mammal, the fourth set different than the third set, while operating the second set of electrodes as recorder electrodes in and/or on the mammal, thereby obtaining third electrical data from the second set of electrodes, wherein
the action of evaluating data includes evaluating the third electrical data while also evaluating the second electrical data and the first electrical data, and
the electrodes of the first set are located closer to one another than the electrodes of the third set and between electrodes of the third set, and the electrodes of the third set are located closer to one another than the electrodes of the fourth set and between electrodes of the fourth set.

21. The method of claim 19, wherein:
the method further comprises evaluating the determined spatial positioning data and determining that over insertion of the electrode array into the cochlea has occurred based on the determined spatial positioning data.

22. The method of claim 19, wherein:
the method further comprises evaluating the determined spatial positioning data and determining that the electrode array has punctured through a wall of the cochlea or based on the determined spatial positioning data.

23. A method, comprising:
obtaining first data by:
operating a first set of electrodes as a source and sink in and/or on a mammal while operating a second set of electrodes as recorder electrodes in and/or on a mammal thereby obtaining first electrical data from the second set of electrodes;
obtaining second data by:
operating a third set of electrodes as a source and sink in and/or on the mammal, the third set being different than the first set and including two electrodes that are further from each other than respective electrodes of the first set, while operating the second set of electrodes as recorder electrodes in and/or on a mammal and thereby obtaining second electrical data from the second set of electrodes;
operating a fourth set of electrodes as a source and sink in and/or on the mammal, the fourth set of electrodes being different than the third set and the first set and including two electrodes that are further from each other than respective electrodes of the third set, while operating the second set of electrodes as recorder electrodes in and/or on the mammal, thereby obtaining third electrical data from the second set of electrodes;

evaluating data by identifying an electrical property of the fourth data that is substantially deviant from that of the first data and the third data, and based at least in part on a distance of electrodes of the fourth set determined based on the evaluation of the data, determining spatial positioning data of the electrodes of the second set.

24. The method of claim 23, further comprising:

determining a distance of the second set of electrodes from a modiolus wall of the cochlea based on the determined spatial positioning data of the electrodes of the second set.

* * * * *